US012686718B2

(12) United States Patent
Queva et al.

(10) Patent No.: US 12,686,718 B2
(45) Date of Patent: Jul. 21, 2026

(54) TARGETED BINDING AGENTS AGAINST B7-H1

(71) Applicant: MEDIMMUNE LIMITED, Cambridge (GB)

(72) Inventors: Christophe Queva, Bainbridge Island, WA (US); Michelle Morrow, Cambridge (GB); Scott Hammond, Olney, MD (US); Marat Alimzhanov, Wellesley, MA (US); John Babcook, Burnaby (CA); Ian Foltz, Burnaby (CA); Jaspal Singh Kang, Surrey (CA); Laura Sekirov, Burnaby (CA); Melanie Boyle, Cambridge (GB); Matthieu Chodorge, Cambridge (GB); Ross A. Stewart, Cambridge (GB); Kathleen Ann Mulgrew, Gaithersburg, MD (US)

( * ) Notice: Subject to any disclaimer, the term of this patent is extended or adjusted under 35 U.S.C. 154(b) by 203 days.

(21) Appl. No.: 18/051,773

(22) Filed: Nov. 1, 2022

(65) Prior Publication Data

US 2023/0235062 A1     Jul. 27, 2023

Related U.S. Application Data

(63) Continuation of application No. 16/519,614, filed on Jul. 23, 2019, now Pat. No. 11,518,809, which is a continuation of application No. 15/333,683, filed on Oct. 25, 2016, now Pat. No. 10,400,039, which is a continuation of application No. 14/271,108, filed on May 6, 2014, now Pat. No. 9,493,565, which is a continuation of application No. 13/511,538, filed as application No. PCT/US2010/058007 on Nov. 24, 2010, now Pat. No. 8,779,108.

(60) Provisional application No. 61/264,061, filed on Nov. 24, 2009.

(51) Int. Cl.
*C07K 16/28*        (2006.01)
*A61K 39/00*        (2006.01)

(52) U.S. Cl.
CPC .... *C07K 16/2827* (2013.01); *A61K 2039/505* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/567* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,217,149 B2 | 7/2012 | Irving et al. | |
| 8,779,108 B2 | 7/2014 | Queva et al. | |
| 9,493,565 B2 * | 11/2016 | Queva ..................... | A61P 31/12 |
| 10,092,645 B2 * | 10/2018 | Stewart ............. | A61K 39/3955 |
| 10,400,039 B2 | 9/2019 | Queva et al. | |
| 11,518,809 B2 * | 12/2022 | Queva ..................... | A61P 31/14 |
| 2005/0022688 A1 | 2/2005 | Asada | |
| 2006/0024607 A1 | 2/2006 | Tanaka et al. | |
| 2009/0005594 A1 | 1/2009 | Chen et al. | |

FOREIGN PATENT DOCUMENTS

| | | |
|---|---|---|
| EP | 1537878 A1 | 6/2008 |
| EP | 2172219 A1 | 4/2010 |
| WO | 2006/133396 A1 | 12/2006 |
| WO | 2007/149032 A1 | 12/2007 |
| WO | 2009/089149 A1 | 7/2009 |
| WO | 2010/077634 A1 | 7/2010 |

OTHER PUBLICATIONS

Blank, C., et al., "Blockade of PD-LI (B7-HI) augments human tumor-specific T cell responses in vitro," Int. J. Cancer, 119(2): 317-327 (2006).
Li, N., et al., "Potent Systemic Antitumor Immunity Induced by Vaccination with Chemotactic-Prostate Tumor Associated Antigen Gene-Modified Tumor Cell and Blockade ofB7-HI," Journal of Clinical Immunology, 27(1): 117-130 (2006).
Parekh, V., et al., "PD-1/PD-L Blockade Prevents Anergy Induction and Enhances the Anti-Tumor Activities of Glycolipid-Activated Invariant NKT Cells," The Journal of Immunology, 182(5):2816-2826 (2009).
Zhang, L., et al., "PD-1/PD-LI interactions inhibit antitumor immune responses in a murine acute myeloid leukemia model," Blood, 114(8): 1545-1552 (2009).
Li, Betty et al., "Anti-Programmed Death-1 Synergizes with Granu-locyte Macrophage Colony-Stimulating Factor-Secreting Tumor Cell Immunotherapy Providing Therapeutic Benefit to Mice with Established Tumors", Clinical Cancer Research 15(5): 1623-1634 (2009).
Lin, Yin-wel David et al., "The PD-1/PD-LI complex resembles the antigen-binding Fv domains of antibodies and T cell receptors", PNAS, 105(8): 3011-3016 (2008).
Nomi, Takeo et al., "Clinical Significance and Therapeutic Potential of the Programmed Death-1 Ligand/Programmed Death-1 Pathway in Human Pancreatic Cancer," 13(7): 2151-2157 (2007).
Strome, Scott E. et al., "B7-HI Blockade Auguments Adoptive T-Cell Immunotherapy for Squamous Cell Carcinoma," Cancer Research, 63: 6501-6505 (2003).
Butte, Manish J., et al., "Progreammed Death-1 Ligand 1 Interacts Specifically with the B7-1 Costimulatorv Molecule to Inhibit T Cell Responses," Immunity 27: 111-122 (2007).

(Continued)

*Primary Examiner* — Ilia I Ouspenski

(74) *Attorney, Agent, or Firm* — MCDONNELL BOEHNEN HULBERT & BERGHOFF LLP

(57) ABSTRACT

Human monoclonal antibodies directed against B7-H1 and uses of these antibodies in diagnostics and for the treatment of diseases associated with the activity and/or expression of B7-H1 are disclosed. Additionally, hybridomas or other cell lines expressing such antibodies are disclosed.

10 Claims, 15 Drawing Sheets

Specification includes a Sequence Listing.

(56)          References Cited

OTHER PUBLICATIONS

Azuma, T., et al., "B7-HI is a ubiquitous antiapoptotic receptor on cancer cells," Blood 111(7): 3635-3643) 2008.

Hohsaka, T., et al., "Incorporation of non-natural amino acids into proteins," Curr. Opin. Chem. Biol., 6: 809-815 (2009).

DeGraaf, A., et al., "Nonatrual Amino Acids for Site-Specific Protein Conugation," Bioconjugate Chemistry, 20: 1281-1295 (2009).

Yan, G., et al., "Genome sequencing and comparison of two nonhuman primate animal models, the cynomolgus and Chinese rhesus macaques," Nature Biotechnology 29(11): 1019-1023 (2011).

International Search Report mailed Feb. 11, 2011, in connection with corresponding International Application No. PCT/US2010/058007.

\* cited by examiner

Fig. 8A/B/C
Control Groups
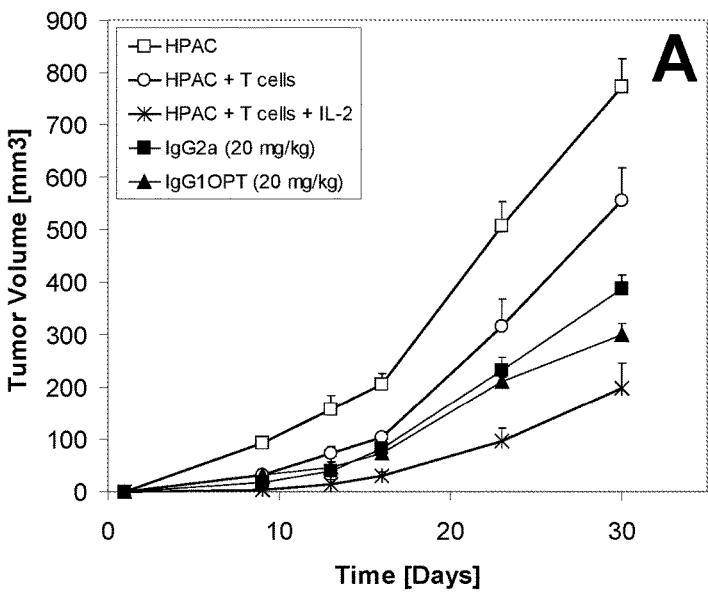
Anti-B7-H1 Abs
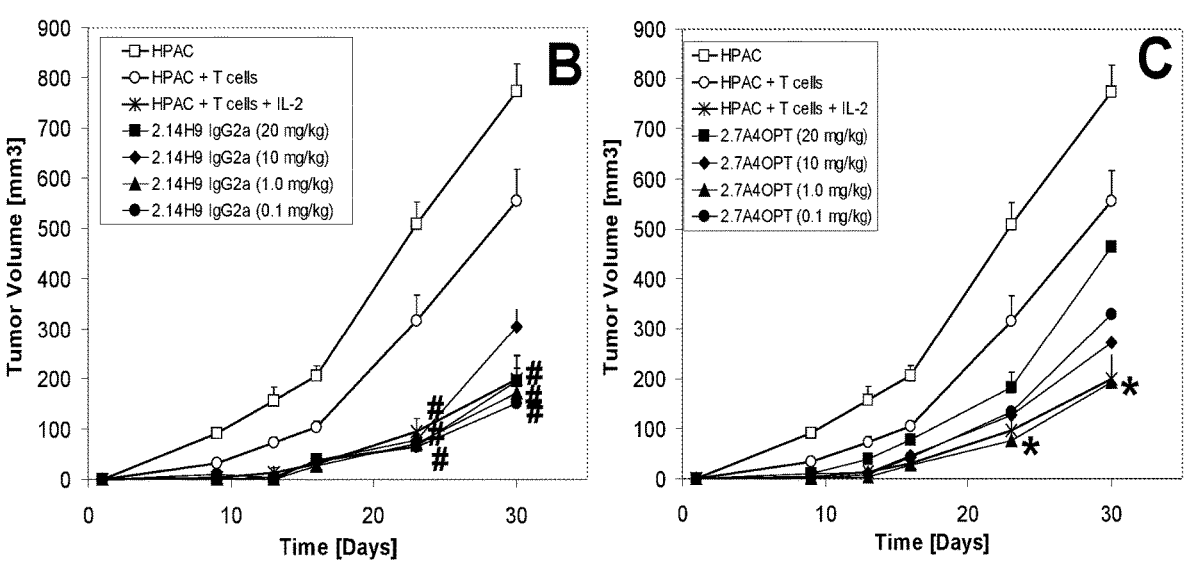

Fig. 9A/B/C
Control Groups
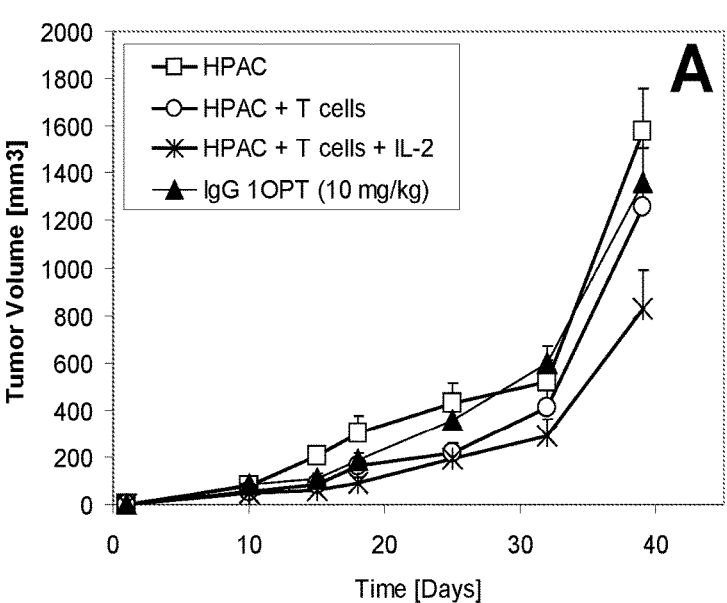
Anti-B7-H1 Abs
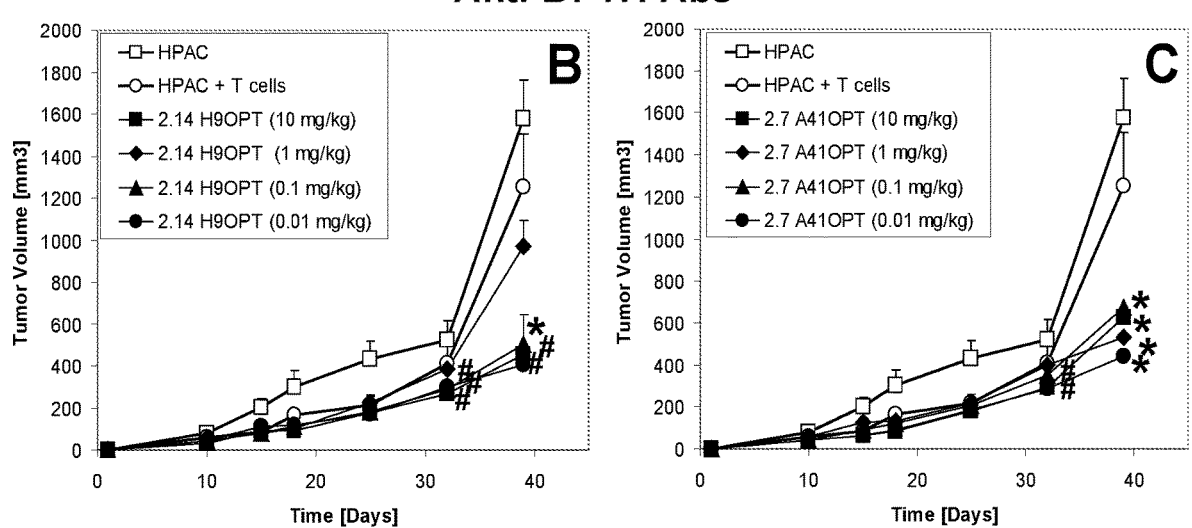

Fig. 10A/B
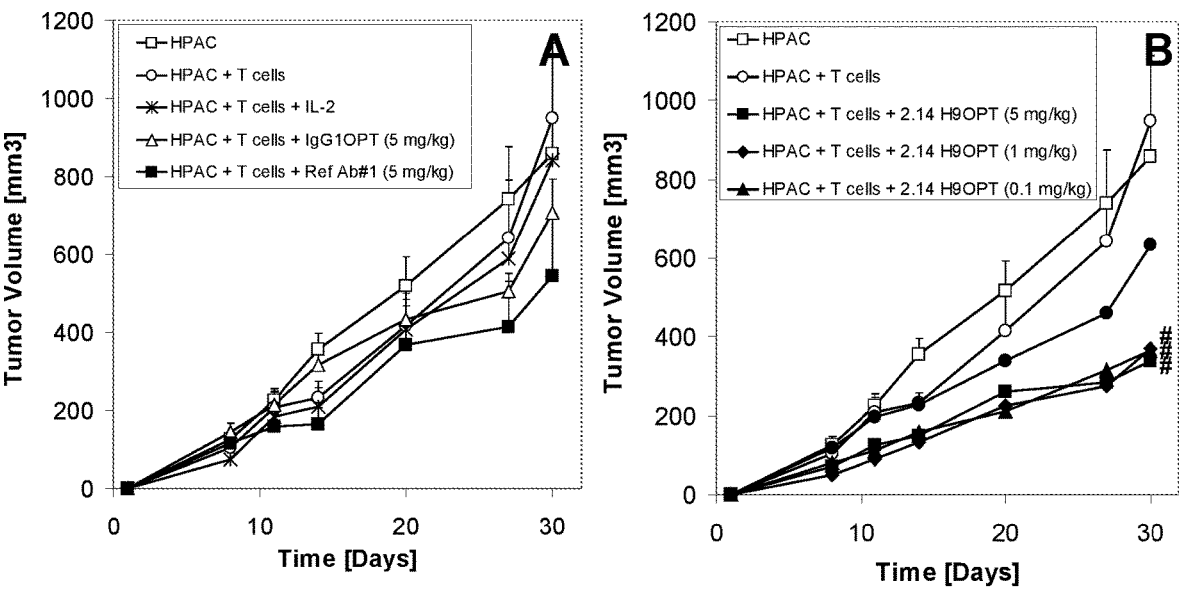

Fig. 12A/B/C/D
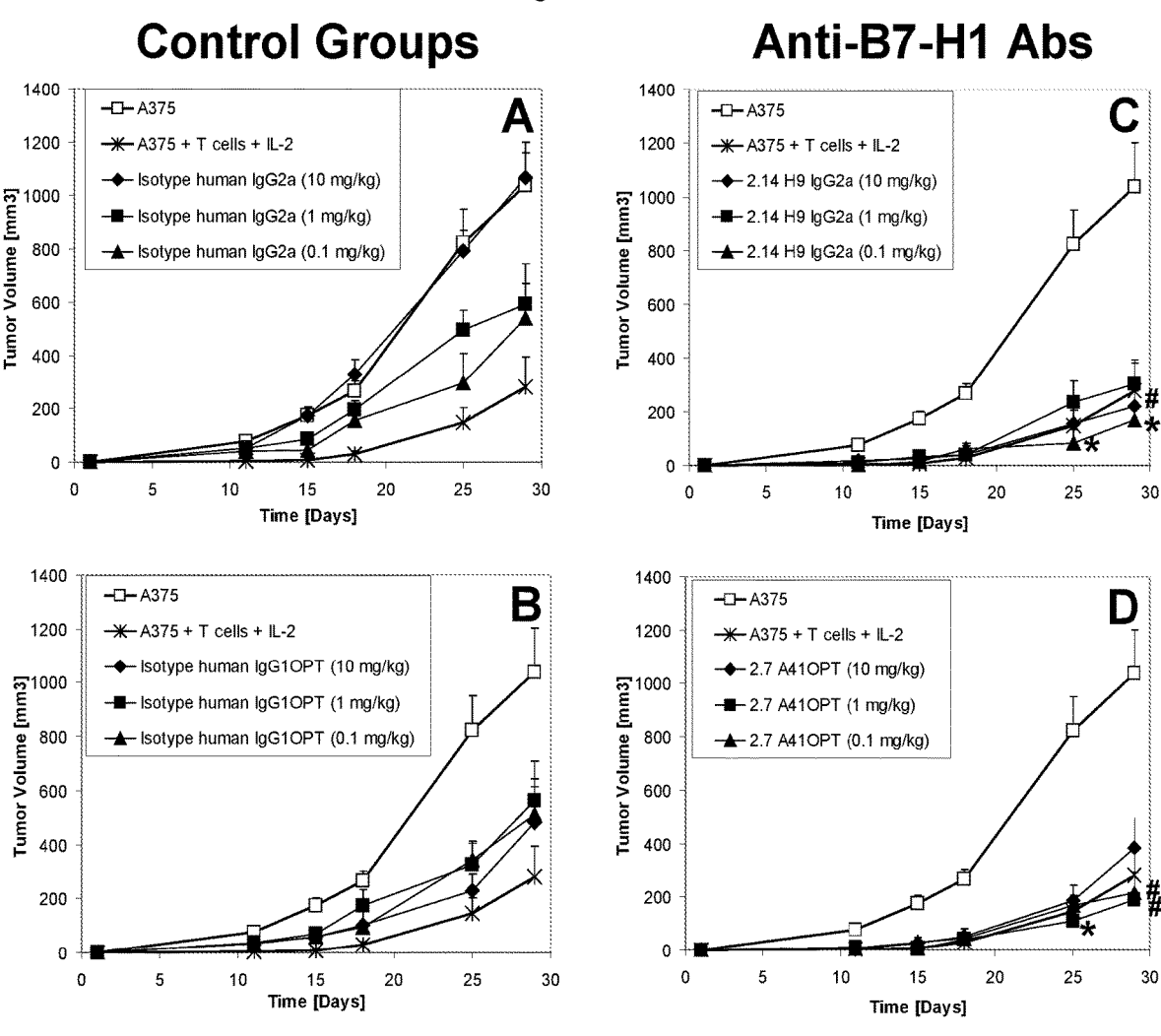

Fig. 13A/B
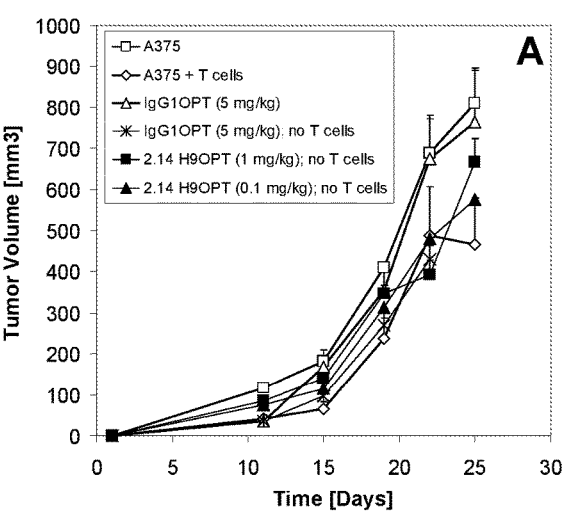
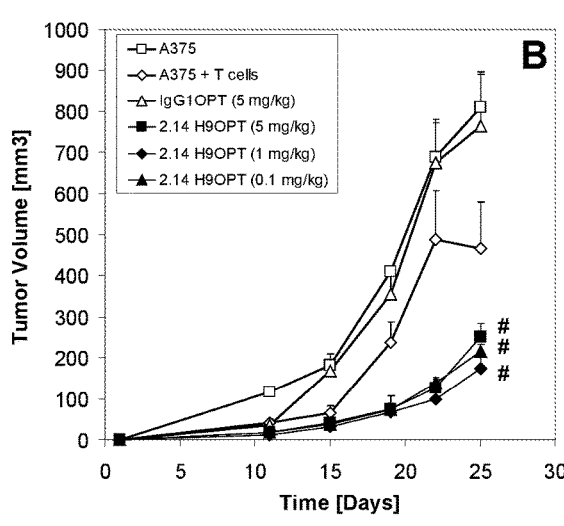

Fig. 14A/B
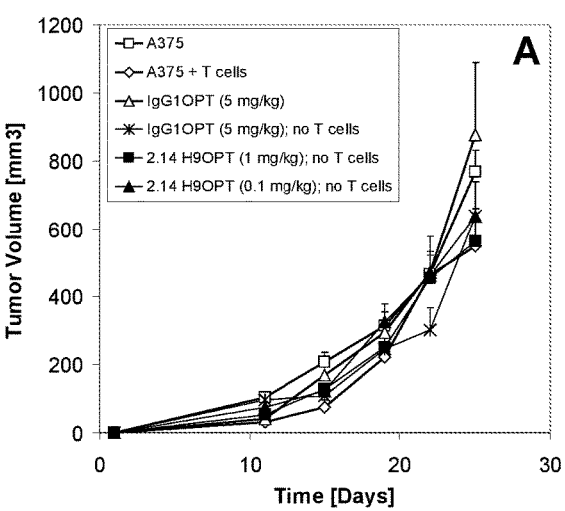
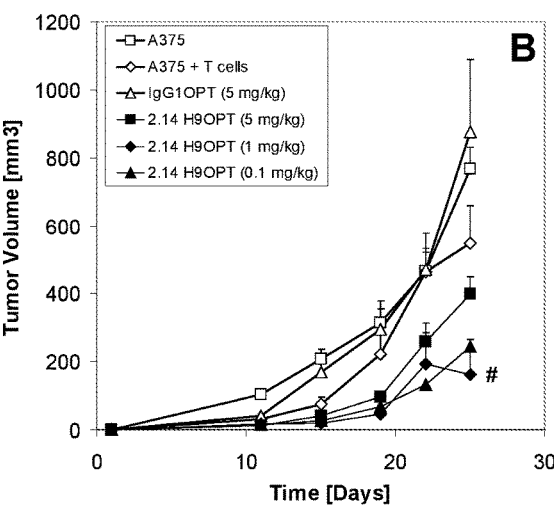

TARGETED BINDING AGENTS AGAINST B7-H1

CROSS REFERENCE TO RELATED APPLICATIONS

This application is a Continuation of U.S. application Ser. No. 16/519,614, filed on Jul. 23, 2019, which is a Continuation of U.S. application Ser. No. 15/333,683, filed on Oct. 25, 2016, now U.S. Pat. No. 10,400,039, which is a Continuation of U.S. application Ser. No. 14/271,108, filed on May 6, 2014, now U.S. Pat. No. 9,493,565, which is a Continuation of U.S. application Ser. No. 13/511,538 filed on Aug. 7, 2012, now U.S. Pat. No. 8,779,108, which is a U.S. National Stage Application of International Application No. PCT/US2010/058007 filed on Nov. 24, 2010, which claims benefit under 35 U.S.C. § 119(e) of U.S. Provisional Application No. 61/264,061 filed Nov. 24, 2009. Each of the above listed applications is incorporated by reference herein in its entirety for all purposes.

REFERENCE TO THE SEQUENCE LISTING

This application is being filed electronically and includes an electronically submitted sequence listing. The sequence listing is entitled "22-0661-WO-US-CON4_Sequence-Listing.xml" and was created on Jun. 17, 2025, and has a size of 180,316 bytes. The sequence listing contained in this .xml file is part of the specification and is herein incorporated by reference in its entirety.

FIELD OF THE INVENTION

The invention relates to targeted binding agents against the B7-H1 protein and uses of such agents. In some embodiments, the invention relates to fully human monoclonal antibodies directed to B7-H1 and uses of these antibodies. Aspects of the invention also relate to cell lines expressing such targeted binding agents or antibodies. The described targeted binding agents are useful as diagnostics and for the treatment of diseases associated with the activity and/or expression of B7-H1.

DESCRIPTION OF THE RELATED ART

An adaptive immune response involves activation, selection, and clonal proliferation of two major classes of lymphocytes termed T cells and B cells. After encountering an antigen, T cells proliferate and differentiate into antigen-specific effector cells, while B cells proliferate and differentiate into antibody-secreting cells. T cell activation is a multi-step process requiring several signaling events between the T cell and an antigen-presenting cell (APC). For T cell activation to occur, two types of signals must be delivered to a resting T cell. The first type is mediated by the antigen-specific T cell receptor (TcR), and confers specificity to the immune response. The second, costimulatory, type regulates the magnitude of the response and is delivered through accessory receptors on the T cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of a T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Molecular homologues of CD28 and CTLA-4 and their B-7 like ligands have been recently identified. ICOS is a CD28-like costimulatory receptor. PD-1 (Programmed Death 1) is an inhibitory receptor and a counterpart of CTLA-4. This disclosure relates to modulation of immune responses mediated by B7-H1.

B7-H1, also known as PD-L1, is a type I transmembrane protein of approximately 53 kDa in size. In humans B7-H1 is expressed on a number of immune cell types including activated and anergic/exhausted T cells, on naïve and activated B cells, as well as on myeloid dendritic cells (DC), monocytes and mast cells. It is also expressed on non-immune cells including islets of the pancreas, Kupffer cells of the liver, vascular endothelium and selected epithelia, for example airway epithelia and renal tubule epithelia, where its expression is enhanced during inflammatory episodes. B7-H1 expression is also found at increased levels on a number of tumours including, but not limited to breast, colon, colorectal, lung, renal, including renal cell carcinoma, gastric, bladder, non-small cell lung cancer (NSCLC), hepatocellular cancer (HCC), and pancreatic cancer, as well as melanoma.

B7-H1 is a member of the B7 family of proteins, which contain two extracellular Ig domains, one N-terminal V-type domain followed by a C-type domain. The intracellular domain of 30 amino acids length contains no obvious signaling motifs, but does bear a potential site for protein kinase C phosphorylation. The murine form of B7-H1 bears 69% amino acid identity with the human form of B7-H1, and also shares a conserved structure.

B7-H1 is known to bind two alternative ligands, the first of these, PD-1, is a 50-55 kDa type I transmembrane receptor that was originally identified in a T cell line undergoing activation-induced apoptosis. PD-1 is expressed on activated T cells, B cells, and monocytes, as well as other cells of the immune system and binds both B7-H1 (PD-L1) and the related B7-DC (PD-L2). The second is the B7 family member B7-1, which is expressed on activated T cells, B cells, monocytes and antigen presenting cells.

PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine (TEYATI in human and mouse) are also conserved between human and murine orthologues.

Signalling via the PD-1/B7-H1 axis is believed to serve critical, non-redundant functions within the immune system, by negatively regulating T cell responses. This regulation is involved in T cell development in the thymus, in regulation of chronic inflammatory responses and in maintenance of both peripheral tolerance and immune privilege. The critical nature of these functions is exemplified in PD-1-deficient mice, which exhibit an autoimmune phenotype. PD-1 deficiency in the C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies. The function of signaling via B7-H1/B7-1 is less clear, but is thought to also be involved in delivering negative regulatory signals to both T cells and antigen presenting cells.

B7-H1 expression on tumour cells is believed to aid tumours in evading detection and elimination by the immune system. B7-H1 functions in this respect via several alternative mechanisms including driving exhaustion and anergy of tumour infiltrating T lymphocytes, stimulating secretion of immune repressive cytokines into the tumour micro-environment, stimulating repressive regulatory T cell function and protecting B7-H1 expressing tumour cells from lysis by tumour cell specific cytotoxic T cells.

In general, a need exists to provide safe and effective therapeutic methods for disorders associated with repression of an immune response such as, for example cancer and chronic viral infection. Modulation of the immune responses involved in these disorders can be accomplished by manipulation of the B7-H1/PD-1 pathway.

SUMMARY OF THE INVENTION

The present invention relates to targeted binding agents that specifically bind to B7-H1 and inhibit the biological activity of B7-H1. In one embodiment of the invention, the invention relates to targeted binding agents that specifically bind to B7-H1 and thereby inhibit B7-H1 activity. In another embodiment of the invention, the invention relates to targeted binding agents that specifically bind to B7-H1 and thereby inhibit binding of B7-H1 to PD-1. In yet another embodiment of the invention, the invention relates to targeted binding agents that block B7-H1 induced T-cell suppression and thereby enhance anti-tumor immunity. In yet another embodiment of the invention, the invention further relates to targeted binding agents that can further stimulate one or more of the following activities including T cell proliferation, IFN-7 and/or IL-2 secretion in mixed lymphocyte reactions. Embodiments of the invention relate to targeted binding agents that specifically bind to B7-H1 and inhibit the biological activity of B7-H1. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the biological activity than would occur in the absence of the targeted binding agent.

Embodiments of the invention relate to targeted binding agents that specifically bind to B7-H1 and thereby inhibit B7-H1 activity. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of B7-H1 activity than would occur in the absence of the targeted binding agent.

Embodiments of the invention relate to targeted binding agents that specifically bind to B7-H1 and thereby inhibit binding to PD-1. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of B7-H1/PD-1 receptor ligand binding compared to what would occur in the absence of the targeted binding agent.

In another embodiment, the targeted binding agents of the invention can inhibit binding of PD-1/Fc to human B7-H1 expressed on ES-2 cells. In one embodiment the targeted binding agent inhibits binding with an IC50 of less than 1 nM, 0.5 nM, 0.4, 0.3, 0.2, 0.1, 0.09, 0.08, 0.07 or 0.06 nM. Further, in another embodiment, the antibodies of the invention have an IC50 of about 1 nM down to about 0.06 nM; or of about 0.5 nM down to about 0.06 nM; or of about 0.1 nM down to about 0.06 nM; or of about 1 nM down to about 0.1 nM; or of about 1 nM down to about 0.5 nM.

Embodiments of the invention relate to targeted binding agents that specifically bind to B7-H1 and thereby inhibit binding to its ligand B7-1. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, 95%, 96%, 97%, 98% 99% or 100% of B7-H1/B7-1 receptor ligand binding compared to what would occur in the absence of the targeted binding agent.

Embodiments of the invention relate to targeted binding agents that specifically bind to B7-H1 and inhibit B7-H1 induced tumor proliferation. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of B7-H1 induced tumor proliferation than would occur in the absence of the targeted binding agent.

Further embodiments of the invention relate to targeted binding agents that specifically bind to B7-H1 and thereby inhibit B7-H1 induced tumor cell survival. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of B7-H1 induced tumor cell survival than would occur in the absence of the targeted binding agent.

Further embodiments of the invention relate to targeted binding agents that specifically bind to B7-H1 and thereby inhibit tumour growth of A375 or HPAC cancer cell lines. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of growth of cancer cells at day 30 compared to an isotype control.

Further embodiments of the invention relate to targeted binding agents that specifically bind to B7-H1 and thereby inhibit B7-H1 mediated suppression of tumour reactive T-cells, thereby enhancing anti-tumour cytolytic T-cell activity. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of B7-H1 mediated suppression of tumour reactive T-cell activity than would occur in the absence of the targeted binding agent.

Further embodiments of the invention relate to targeted binding agents that specifically bind to B7-H1 and thereby enhance anti-tumour immunity. In one embodiment the targeted binding agent enhances at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of anti-tumor immunity than would occur in the absence of the targeted binding agent.

Further embodiments of the invention relate to targeted binding agents that specifically bind to B7-H1 and thereby inhibit cell proliferation. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cell proliferation than would occur in the absence of the targeted binding agent.

Further embodiments of the invention relate to targeted binding agents that specifically bind to B7-H1 and increase specific cytolytic (CTL) activity against B7-H1 expressing tumor cells. In one embodiment, the antibodies of the invention have an EC50 of less than or equal to 100 nM, 50 nM or 1 nM. Further, in another embodiment, the antibodies of the invention have an EC50 of about 100 nM down to about 1 nM; or of about 50 nM down to about 1 nM; or of about 20 nM down to about 1 nM; or of about 100 nM down to about 50 nM; or of about 100 nM down to about 70 nM.

Further embodiments of the invention relate to targeted binding agents that specifically bind to B7-H1 and inhibit B7-H1 mediated suppression of T-cell proliferation at an EC50 less than or equal to 100 nM. In one embodiment, the antibodies of the invention have an EC50 of less than or equal to 100 nM, e.g., 90, 80, 70, 60, 50, 40, 30, 20 or 10 nM. Further, in another embodiment, the antibodies of the invention have an EC50 of about 100 nM down to about 10 nM; or of about 50 nM down to about 10 nM; or of about 20 nM down to about 10 nM; or of about 100 nM down to about 50 nM; or of about 100 nM down to about 70 nM; or of about 100 nM down to about 80 nM.

The targeted binding agents also inhibit tumour cell adhesion, motility, invasion and cellular metastasis and in addition, the targeted binding agents are useful for reducing tumour growth. Mechanisms by which this can be achieved can include, and are not limited to, inhibiting B7-H1 activity.

In one embodiment of the invention, the targeted binding agent is an antibody. In one embodiment of the invention, the targeted binding agent is a monoclonal antibody. In one embodiment of the invention, the targeted binding agent is a fully human monoclonal antibody or a fragment thereof. Such monoclonal antibodies may be referred to herein as anti-B7-H1 antibodies or antibodies of the invention.

Antibodies, monoclonal antibodies and human monoclonal antibodies include the antibodies of the IgG1, IgG2, IgG3 and IgG4 isotypes, for example IgG2. In one embodiment of the invention, the targeted binding agent is a fully human monoclonal antibody of the IgG2 isotype. This isotype has reduced potential to elicit effector function in comparison with other isotypes, which may lead to reduced toxicity. In another embodiment of the invention, the targeted binding agent is a fully human monoclonal antibody of the IgG1 isotype. The IgG1 isotype has increased potential to elicit Antibody Directed Cell-mediated Cytotoxicity (ADCC) in comparison with other isotypes, which may lead to improved efficacy. The IgG1 isotype has improved stability in comparison with other isotypes, e.g. IgG4, which may lead to improved bioavailability/ease of manufacture/ longer half-life. In one embodiment, the fully human monoclonal antibody of the IgG1 isotype is of the z, za or f allotype. In one embodiment of the invention, the targeted binding agent has desirable therapeutic properties, selected from one or more of the following: high binding affinity for B7-H1, the ability to inhibit B7-H1 activity in vitro and in vivo, the ability to inhibit B7-H1-mediated tumour cell survival, and the ability to inhibit B7-H1 mediated suppression of tumour reactive T-cells, which may in turn reduce tumour cell proliferation, motility, invasion, metastasis, and tumour growth.

In one embodiment, the invention includes antibodies that specifically bind to B7-H1 with very high affinities (Kd). In some embodiments of the invention, the targeted binding agent binds B7-H1 with a binding affinity (Kd) of less than 5 nanomolar (nM). In other embodiments, the targeted binding agent binds with a Kd of less than 4 nM, 3 nM, 2.5 nM, 2 nM or 1 nM. Further, in some other embodiments antibodies of the invention binds B7-H1 with a Kd of about 5 nM to about 1 nM; or about 5 nM to about 2 nM; or about 5 nM to about 3 nM; or about 5 nM to about 4 nM; or about 3 nM to about 1 nM; or about 2 nM to about 1 nM. In some embodiments of the invention, the targeted binding agent binds B7-H1 with a Kd of less than 950 picomolar (pM). In some embodiments of the invention, the targeted binding agent binds B7-H1 with a Kd of less than 900 pM. In other embodiments, the targeted binding agent binds B7-H1 with a Kd of less than 800 pM, 700 pM or 600 pM. In some embodiments of the invention, the targeted binding agent binds B7-H1 with a Kd of less than 500 pM. In other embodiments, the targeted binding agent binds B7-H1 with a Kd of less than 400 pM. In still other embodiments, the targeted binding agent binds B7-H1 with a Kd of less than 300 pM. In some other embodiments, the targeted binding agent binds B7-H1 with a Kd of less than 200 pM. In some other embodiments, the targeted binding agent binds B7-H1 with a Kd of less than 100 pM. Further, in some other embodiments antibodies of the invention binds B7-H1 with a Kd of about 900 pM to about 100 pM; or about 900 pM to about 200 pM; or about 900 pM to about 300 pM; or about 900 pM to about 400 pM; or about 900 pM to about 500 pM; or about 900 pM to about 600 pM; or about 900 pM to about 700 pM; or about 200 pM to about 100 pM; or about 300 pM to about 200 pM; or about 400 pM to about 300 pM. In some other embodiments, the targeted binding agent binds B7-H1 with a Kd of less than 90 pM, 80 pM, 70 pM, 60 pM, 55 pM or 50 pM. In some other embodiments, the targeted binding agent binds B7-H1 with a Kd of less than 60 pM. In some other embodiments, the targeted binding agent binds B7-H1 with a Kd of less than 55 pM. Further, in some other embodiments antibodies of the invention binds B7-H1 with a Kd of about 100 pM to about 50 pM; or about 100 pM to about 70 pM; or about 100 pM to about 80 pM; or about 100 pM to about 90 pM; or about 70 pM to about 50 pM; or about 60 pM to about 50 pM; or about 55 pM to about 50 pM. The Kd may be assessed using a method described herein or known to one of skill in the art (e.g., a BIAcore assay, ELISA) (Biacore International AB, Uppsala, Sweden). Targeted binding agents of the invention have considerably improved binding affinities for B7-H1 in comparison with the antibodies reported in the prior art.

The binding properties of the targeted binding agent or antibody of the invention may also be measured by reference to the dissociation or association rates ($k_{off}$ and $k_{on}$ respectively).

In one embodiment of the invention, a targeted binding agent or an antibody of the invention may have a $k_{on}$ rate (antibody (Ab)+antigen (Ag)$^{k_{on}} \rightarrow$Ab-Ag) of at least $10^4$ $M^{-1}s^{-1}$, at least $5 \times 10^4$ $M^{-1}s^{-1}$, at least $10^5$ $M^{-1}s^{-1}$, at least $2 \times 10^5$ $M^{-1}s^{-1}$, at least $5 \times 10^5$ $M^{-1}s^{-1}$, at least $10^6$ $M^{-1}s^{-1}$, at least $5 \times 10^6$ $M^{-1}s^{-1}$, at least $10^7$ $M^{-1}s^{-1}$, at least $5 \times 10^7$ $M^{-1}s^{-1}$, or at least $10^8$ $M^{-1}s^{-1}$ as measured by a BIAcore assay. Further, in some other embodiments antibodies of the invention have a $k_{on}$ rate of about $5 \times 10^4$ $M^{-1}s^{-1}$ to about $5 \times 10^8$ $M^{-1}s^{-1}$; or of about $5 \times 10^5$ $M^{-1}s^{-1}$ to about $5 \times 10^8$ $M^{-1}s^{-1}$; or of about $5 \times 10^6$ $M^{-1}s^{-1}$ to about $5 \times 10^8$ $M^{-1}s^{-1}$; or of about $5 \times 10^7$ $M^{-1}s^1$ to about $5 \times 10^8$ $M^{-1}s^{-1}$, as measured by a BIAcore assay.

In another embodiment of the invention, targeted binding agent or an antibody may have a $k_{off}$ rate ((Ab-Ag)$^{k_{off}} \rightarrow$antibody (Ab)+antigen (Ag)) of less than $5 \times 10^{-1}$ $s^{-1}$, less than $10^{-1}$ $s^{-1}$, less than $5 \times 10^{-2}$ $s^{-1}$, less than $10^{-2}$ $s^{-1}$, less than $5 \times 10^{-3}$ $s^{-1}$, less than $10^{-3}$ $s^{-1}$, less than $5 \times 10^{-4}$ $s^{-1}$, less than $10^{-4}$-1, less than $5 \times 10^{-5}$ $s^{-1}$, less than $10^{-5}$ $s^{-1}$, less than $5 \times 10^{-6}$ $s^{-1}$ less than $10^{-6}$ $s^{-1}$ less than $5 \times 10^{-7}$ $s^{-1}$, less than $10^{-7}s^{-1}$, less than $5 \times 10^{-8}$ $s^{-1}$ less than $10^{-8}$ $s^{-1}$ less than $5 \times 10^{-9}$ $s^{-1}$, less than $10^{-9}$ $s^{-1}$, or less than $10^{-10}$ $s^{-1}$ as measured by a BIAcore assay. Further, in some other embodiments antibodies of the invention have a $k_{off}$ rate of about $1 \times 10^{-4}$ $s^{-1}$ to about $1 \times 10^{-5}$ $s^{-1}$; or of about $1 \times 10^{-4}$ $s^{-1}$ to about $5 \times 10^{-4}$ $s^{-1}$, as measured by a BIAcore assay.

The targeted binding agent of the invention specifically binds human B7-H1. In some examples, the targeted binding agent of the invention does not bind other immune co-modulatory proteins, e.g., human PD-L2, human B7-H2, human B7-H3, human CD28, human CTLA-4 and human PD1.

In another embodiment, the targeted binding agent of the invention is cross-reactive with other B7-H1 proteins from other species. In one embodiment, the targeted binding agent of the invention is cross-reactive with cynomolgus monkey B7-H1. In another embodiment, the targeted binding agent of the invention is cross-reactive with mouse B7-H1, e.g., 2.7A4. In another embodiment, the targeted binding agent of the invention is cross-reactive with cynomolgus monkey B7-H1 and with mouse B7-H1, e.g., 2.7A4. In another embodiment, the targeted binding agent of the invention is cross-reactive with cynomolgus monkey B7-H1 but not with mouse B7-H1, e.g., 2.9D10 and 2.14H9.

In one embodiment, the targeted binding agent or antibody comprises a sequence comprising any one of the heavy chain sequences (VH) shown in Table 8. In another embodiment the targeted binding agent or antibody comprises a sequence comprising any one of the heavy chain sequences of antibodies 2.9D10, 2.7A4, 2.14H9, 3.15G8, 2.20A8, 3.18G1, 2.7A4OPT, or 2.14H9OPT. Light-chain promiscuity is well established in the art, thus, a targeted binding agent or antibody comprising a sequence comprising any one of the heavy chain sequences of antibodies 2.9D10, 2.7A4, 2.14H9, 3.15G8, 2.20A8, 3.18G1, 2.7A4OPT, or 2.14H9OPT, or another antibody as disclosed herein, may further comprise any one of the light chain sequences (VL) shown in Table 9 or of antibodies 2.9D10, 2.7A4, 2.14H9, 3.15G8, 2.20A8, 3.18G1, 2.7A4OPT or 2.14H9OPT, or other antibody as disclosed herein. In another embodiment the targeted binding agent or antibody comprises a sequence comprising any one of the heavy chain sequences of antibodies 2.9D10, 2.7A4, 2.14H9, 3.15G8, 2.20A8, 3.18G1, 2.7A4OPT, or 2.14H9OPT and further comprising the corresponding light chain sequence of antibody 2.9D10, 2.7A4, 2.14H9, 3.15G8, 2.20A8, 3.18G1, 2.7A4OPT, or 2.14H9OPT. In some embodiments, the antibody is a fully human monoclonal antibody.

In one embodiment, the targeted binding agent or antibody comprises a sequence comprising any one of the light chain sequences shown in Table 9. In another embodiment, the targeted binding agent or antibody comprises a sequence comprising any one of the light chain sequences of antibodies 2.9D10, 2.7A4, 2.14H9, 3.15G8, 2.20A8, 3.18G1, 2.7A4OPT, or 2.14H9OPT. In some embodiments, the antibody is a fully human monoclonal antibody.

In another embodiment the targeted binding agent or antibody comprises a sequence comprising any of the heavy chain sequence of antibody 2.7A4 and further comprising the light chain sequence of antibody 2.7A4. In another embodiment the targeted binding agent or antibody comprises a sequence comprising any of the heavy chain sequence of antibody 2.14H9 and further comprising the light chain sequence of antibody 2.14H9. In another embodiment the targeted binding agent or antibody comprises a sequence comprising any of the heavy chain sequence of antibody 2.9D10 and further comprising the light chain sequence of antibody 2.9D10. In another embodiment the targeted binding agent or antibody comprises a sequence comprising any of the heavy chain sequence of antibody 2.7A.4OPT and further comprising the light chain sequence of antibody 2.7A.4OPT. In another embodiment the targeted binding agent or antibody comprises a sequence comprising any of the heavy chain sequence of antibody 2.14H9OPT and further comprising the light chain sequence of antibody 2.14H9OPT.

In some embodiments, the targeting binding agent is any one of the monoclonal antibodies as shown in Table 1. In some embodiments, the targeting binding agent is a monoclonal antibody selected from the group consisting of: 2.7A4, 2.14H9, 2.9D10, 2.7A4OPT or 2.14H9OPT. In one embodiment, the targeting binding agent comprises one or more of fully human monoclonal antibodies 2.7A4, 2.14H9, 2.9D10, 2.7A4OPT or 2.14H9OPT. In certain embodiments, the targeting binding agent is monoclonal antibody 2.7A4. In certain other embodiments, the targeting binding agent is monoclonal antibody 2.14H9. In still other embodiments, the targeting binding agent is monoclonal antibody 2.9D10. In certain embodiments, the targeting binding agent is monoclonal antibody 2.7A4OPT. In certain other embodiments, the targeting binding agent is monoclonal antibody 2.14H9OPT. In additional embodiments, the targeted binding agent is derivable from any of the foregoing monoclonal antibodies.

In another embodiment the targeted binding agent may comprise a sequence comprising any one of the CDR1, CDR2 or CDR3 of the heavy chain variable sequences encoded by a polynucleotide in a plasmid designated 2.7A4_G, 2.14H9_G, and 2.9D10_NG which were deposited at NCIMB under number 41598 on Nov. 19, 2008, under number 41597 on Nov. 19, 2008, and under number 41599 on Nov. 19, 2008, respectively.

In another embodiment the targeted binding agent may comprise a sequence comprising any one of the CDR1, CDR2 or CDR3 of the light chain variable domain sequences encoded by a polynucleotide in a plasmid designated 2.7A4_G, 2.14H9_G and 2.9D10_NG which were deposited under number 41598 on Nov. 19, 2008, under number 41597 on Nov. 19, 2008, or under number 41599 on Nov. 19, 2008, respectively.

In one embodiment, a targeted binding agent or an antibody of the invention comprises a heavy chain variable domain amino acid sequence comprising a CDR3 encoded by the polynucleotide in plasmid designated 2.7A4_G which was deposited at the NCIMB under deposit number 41598 on Nov. 19, 2008 and a light chain variable domain amino acid sequence comprising a CDR3 encoded by the polynucleotide in plasmid designated 2.7A4_G which was deposited at the NCIMB under deposit number 41598 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.7A4_G which was deposited at the NCIMB under deposit number 41598 on Nov. 19, 2008.

In another embodiment, a targeted binding agent or an antibody of the invention comprises a light chain variable domain amino acid sequence comprising at least one, at least two, or at least three of the CDRs of the antibody encoded by the polynucleotide in plasmid designated 2.7A4_G which was deposited at the NCIMB under deposit number 41598 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.7A4_G which was deposited at the NCIMB under deposit number 41598 on Nov. 19, 2008 and a light chain variable domain amino acid sequence comprising at least one, at least two, or at least three of the CDRs of the antibody encoded by the poly-nucleotide in plasmid designated 2.7A4_G which was deposited at the NCIMB under deposit number 41598 on Nov. 19, 2008.

In one embodiment, a targeted binding agent or an anti-body of the invention comprises a heavy chain variable domain amino acid sequence comprising a CDR3 encoded by the polynucleotide in plasmid designated 2.14H9_G which was deposited at the NCIMB under number 41597 on Nov. 19, 2008.

In one embodiment, a targeted binding agent or an anti-body of the invention comprises a heavy chain variable domain amino acid sequence comprising a CDR3 encoded by the polynucleotide in plasmid designated 2.14H9_G which was deposited at the NCIMB under number 41597 on Nov. 19, 2008, and a light chain variable domain amino acid sequence comprising a CDR3 encoded by the polynucle-otide in plasmid designated 2.14H9_G which was deposited at the NCIMB under number 41597 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.14H9_G which was deposited at the NCIMB under number 41597 on Nov. 19, 2008.

In another embodiment, a targeted binding agent or an antibody of the invention comprises a light chain variable domain amino acid sequence comprising at least one, at least two, or at least three of the CDRs of the antibody encoded by the polynucleotide in plasmid designated 2.14H9_G which was deposited at the NCIMB under number 41597 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.14H9_G which was deposited at the NCIMB under number 41597 on Nov. 19, 2008 and a light chain variable domain amino acid sequence comprising at least one, at least two, or at least three of the CDRs of the antibody encoded by the polynucleotide in plasmid designated 2.14H9_G which was deposited at the NCIMB under number 41597 on Nov. 19, 2008.

In one embodiment, a targeted binding agent or an anti-body of the invention comprises a heavy chain variable domain amino acid sequence comprising a CDR3 encoded by the polynucleotide in plasmid designated 2.9D10NG which was deposited at the NCIMB under number 41599 on Nov. 19, 2008.

In one embodiment, a targeted binding agent or an anti-body of the invention comprises a heavy chain variable domain amino acid sequence comprising a CDR3 encoded by the polynucleotide in plasmid designated 2.9D10_NG which was deposited at the NCIMB under number 41599 on Nov. 19, 2008 and a light chain variable domain amino acid sequence comprising a CDR3 encoded by the polynucle-otide in plasmid designated 2.9D10_NG which was depos-ited at the NCIMB under number 41599 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.9D10_NG which was deposited at the NCIMB under number 41599 on Nov. 19, 2008.

In another embodiment, a targeted binding agent or an antibody of the invention comprises a light chain variable domain amino acid sequence comprising at least one, at least two, or at least three of the CDRs of the antibody encoded by the polynucleotide in plasmid designated 2.9D10_NG which was deposited at the NCIMB under number 41599 on Nov. 19, 2008.

In another embodiment, a targeted binding agent or an antibody of the invention comprises a heavy chain variable domain amino acid sequence comprising at least one, at least two, or at least three of the CDRs of the antibody encoded by the polynucleotide in plasmid designated 2.9D10_NG which was deposited at the NCIMB under number 41599 on Nov. 19, 2008 and a light chain variable domain amino acid sequence comprising at least one, at least two, or at least three of the CDRs of the antibody encoded by the poly-nucleotide in plasmid designated 2.9D10 NG which was deposited at the NCIMB under number 41599 on Nov. 19, 2008.

In another embodiment, a targeted binding agent or an antibody of the invention comprises a heavy chain variable sequence of an antibody encoded by the polynucleotide in plasmid designated 2.7A4_G which was deposited at the NCIMB number 41598 on Nov. 19, 2008.

In another embodiment, a targeted binding agent or an antibody of the invention comprises a heavy chain variable sequence of an antibody encoded by the polynucleotide in plasmid designated 2.14H9_G which was deposited at the NCIMB under number 41597 on Nov. 19, 2008.

In another embodiment, a targeted binding agent or an antibody of the invention comprises a heavy chain variable domain sequence of an antibody encoded by the polynucle-otide in plasmid designated 2.9D10_NG which was depos-ited at the NCIMB under number 41599 on Nov. 19, 2008.

In another embodiment, a targeted binding agent or an antibody of the invention comprises a light chain variable domain of an antibody encoded by the polynucleotide in plasmid designated 2.7A4_G which was deposited at the NCIMB under number 41598 on Nov. 19, 2008.

In another embodiment, a targeted binding agent or an antibody of the invention comprises a light chain variable domain of an antibody encoded by the polynucleotide in plasmid designated 2.14H9_G which was deposited at the NCIMB under number 41597 on Nov. 19, 2008.

In another embodiment, a targeted binding agent or an antibody of the invention comprises a light chain variable domain of an antibody encoded by the polynucleotide in plasmid designated 2.9D10_NG which was deposited at the NCIMB under number 41599 on Nov. 19, 2008.

In another embodiment, a targeted binding agent or an antibody of the invention comprises a heavy chain variable domain sequence of an antibody encoded by the polynucleotide in plasmid designated 2.7A4_G which was deposited at the NCIMB under number 41598 on Nov. 19, 2008 and a light chain variable domain sequence of an antibody encoded by the polynucleotide in plasmid designated 2.7A4_G which was deposited at the NCIMB under number 41598 on Nov. 19, 2008.

In another embodiment, a targeted binding agent or an antibody of the invention comprises a light chain variable domain sequence of an antibody encoded by the polynucleotide in plasmid designated 2.14H9_G which was deposited at the NCIMB under number 41597 on Nov. 19, 2008 and a heavy chain variable domain sequence of an antibody encoded by the polynucleotide in plasmid designated 2.14H9_G which was deposited at the NCIMB under number 41597 on Nov. 19, 2008.

In another embodiment, a targeted binding agent or an antibody of the invention comprises a heavy chain variable domain sequence of an antibody encoded by the polynucleotide in plasmid designated 2.9D10_NG which was deposited at the NCIMB under number 41599 on Nov. 19, 2008 and a light chain variable domain sequence of an antibody encoded by the polynucleotide in plasmid designated 2.9D10_NG which was deposited at the NCIMB under number 41599 on Nov. 19, 2008.

In one embodiment a targeted binding agent or an antibody may comprise a sequence comprising a heavy chain CDR1 (HCDR1), heavy chain CDR2 (HCDR2) and heavy chain CDR3 (HCDR3) selected from any one of the sequences shown in Table 8. In one embodiment a targeted binding agent or an antibody may comprise a sequence comprising a light chain CDR1 (LCDR1), light chain CDR2 (LCDR2) and light chain CDR3 (LCDR3) selected from any one of the sequences shown in Table 9. In one embodiment a targeted binding agent or an antibody may comprise a sequence comprising a HCDR1, HCDR2 and HCDR3 selected from any one of the CDRs of antibodies 2.9D10, 2.7A4, 2.14H9, 3.15G8, 2.20A8, or 3.18G1. In one embodiment a targeted binding agent or an antibody may comprise a sequence comprising a LCDR1, LCDR2 and LCDR3 selected from any one of the CDRs of antibodies 2.9D10, 2.7A4, 2.14H9, 3.15G8, 2.20A8, or 3.18G1.

A further embodiment is a targeted binding agent or an antibody that specifically binds to B7-H1 and comprises a sequence comprising one of the CDR2 and one of the CDR3 sequences shown in Table 9. In a further embodiment the targeted binding agent or antibody further comprises a sequence comprising: a CDR3 sequence as shown in Table 8. In a further embodiment the targeted binding agent or antibody further comprises a sequence comprising: a CDR2 and a CDR3 sequence as shown in Table 8 and/or Table 9. In a further embodiment the targeted binding agent or antibody further comprises a sequence comprising: a CDR1, a CDR2 and a CDR3 sequence as shown in Table 8 and/or Table 9.

In another embodiment the targeted binding agent or antibody may comprise a sequence comprising any one of a CDR1, a CDR2 or a CDR3 of any one of the fully human monoclonal antibodies 2.7A4, 2.14H9 or 2.9D10, as shown in Table 8. In another embodiment the targeted binding agent or antibody may comprise a sequence comprising any one of a CDR1, a CDR2 or a CDR3 of any one of the fully human monoclonal antibodies 2.7A4, 2.14H9 or 2.9D10, as shown in Table 9. In one embodiment the targeted binding agent or antibody may comprise a sequence comprising a CDR1, a CDR2 and a CDR3 of any one of fully human monoclonal antibodies 2.7A4, 2.14H9, 2.9D10, 2.7A4OPT or 2.14H9OPT, as shown in Table 8. In another embodiment the targeted binding agent or antibody may comprise a sequence comprising a CDR1, a CDR2 and a CDR3 of any one of fully human monoclonal antibodies 2.7A4, 2.14H9, 2.9D10, 2.7A4OPT or 2.14H9OPT, as shown in Table 9.

In another embodiment the targeted binding agent or antibody comprises a sequence comprising the CDR1, CDR2 and CDR3 sequence of fully human monoclonal antibody 2.7A4 as shown in Table 8 and the CDR1, CDR2 and CDR3 sequence of fully human monoclonal antibody 2.7A4 as shown in Table 9. In another embodiment the targeted binding agent or antibody comprises a sequence comprising the CDR1, CDR2 and CDR3 sequence of fully human monoclonal antibody 2.14H9 as shown in Table 8 and the CDR1, CDR2 and CDR3 sequence of fully human monoclonal antibody 2.14H9 as shown in Table 9. In another embodiment the targeted binding agent or antibody comprises a sequence comprising the CDR1, CDR2 and CDR3 sequence of fully human monoclonal antibody 2.9D10 as shown in Table 8 and the CDR1, CDR2 and CDR3 sequence of fully human monoclonal antibody 2.9D10 as shown in Table 9. In some embodiments, the antibody is a fully human monoclonal antibody.

It is noted that those of ordinary skill in the art can readily accomplish CDR determinations. See for example, Kabat et al., Sequences of Proteins of Immunological Interest, Fifth Edition, NIH Publication 91-3242, Bethesda MD (1991), vols. 1-3. Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (presently available from the Kabat Database Website; see also Nucleic Acids Research, 2000, 28(1), 214-218). Any immunoglobulin sequence can be numbered according to Kabat by performing an alignment with the Kabat reference sequence. Accordingly, the Kabat numbering system provides a uniform system for numbering immunoglobulin chains.

A further embodiment of the invention is a targeted binding agent or antibody comprising a sequence comprising the contiguous sequence spanning the framework regions and CDRs, specifically from FR1 through FR4 or CDR1 through CDR3, of any one of the sequences 2.9D10, 2.7A4, 2.14H9, 3.15G8, 2.20A8, 3.18G1, 2.7A4OPT, or 2.14H9OPT, or as shown in Table 8 or Table 9. A further embodiment of the invention is a targeted binding agent or antibody comprising a sequence comprising the contiguous sequence spanning the framework regions and CDRs, specifically from FR1 through FR4 or CDR1 through CDR3, of any one of the sequences 2.9D10, 2.7A4, 2.14H9, 3.15G8, 2.20A8, 3.18G1, 2.7A4OPT, or 2.14H9OPT or as shown in Table 8 and Table 9. In one embodiment the targeted binding agent or antibody comprises a sequence comprising the contiguous sequences spanning the framework regions and CDRs, specifically from FR1 through FR4 or CDR1 through CDR3, of any one of the sequences of monoclonal antibodies 2.9D10, 2.7A4, 2.14H9, 3.15G8, 2.20A8, 3.18G1, 2.7A4OPT, or 2.14H9OPT or as shown in Table 8 or Table 9. A further embodiment of the invention is a targeted binding agent or antibody comprising a sequence comprising the contiguous sequence spanning the framework regions and CDRs, specifically from FR1 through FR4 or CDR1 through CDR3, of any one of the sequences of monoclonal antibodies 2.9D10, 2.7A4, 2.14H9, 3.15G8, 2.20A8, 3.18G1, 2.7A4OPT, or 2.14H9OPT or as shown in Table 8 and Table 9. In some embodiments, the antibody is a fully human monoclonal antibody.

In another embodiment, a targeted binding agent or antibody of the invention comprises a CDR3 sequence as shown in Table 8 or 9; or any one of a CDR1, a CDR2 or a CDR3 sequence as shown in Table 8 or 9; or a CDR1, a CDR2 and a CDR3 sequence of a light chain variable domain sequence as shown in Table 8; or a CDR1, a CDR2 and a CDR3 sequence of a heavy chain variable domain sequence as shown as shown in Table 9.

One embodiment provides a targeted binding agent or antibody, or antigen-binding portion thereof, wherein the agent or antibody, or antigen-binding portion thereof, comprises a sequence comprising SEQ ID NO.:2, SEQ ID NO.:7, SEQ ID NO.:12, SEQ ID NO.:17, SEQ ID NO.:22, SEQ ID NO.:27, SEQ ID NO.:32, SEQ ID NO.:37, SEQ ID NO.:42, SEQ ID NO.:47, SEQ ID NO.:52, SEQ ID NO.:57, SEQ ID NO.:62, SEQ ID NO.:67, SEQ ID NO.:72, or SEQ ID NO.:77.

One embodiment provides a targeted binding agent or antibody, or antigen-binding portion thereof, wherein the agent or antibody, or antigen-binding portion thereof, comprises a heavy chain sequence comprising the sequence of SEQ ID NO.:2. In one embodiment, the targeted binding agent or antibody, or antigen-binding portion thereof, further comprises a light chain sequence comprising the sequence of SEQ ID NO.:7. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:2 and comprises a light chain variable domain having at least 90% identity to the amino acid sequence of SEQ ID NO:7.

In another embodiment the targeted binding agent or antibody, or antigen-binding portion thereof, comprises a heavy chain sequence comprising the sequence of SEQ ID NO.:12. In one embodiment, the targeted binding agent or antibody, or antigen-binding portion thereof, further comprises a light chain sequence comprising the sequence of SEQ ID NO.:17. In some embodiments, the antibody is a fully human monoclonal antibody.

In one embodiment the targeted binding agent or antibody, or antigen-binding portion thereof, comprises a heavy chain variable domain having at least 90% identity to the amino acid of SEQ ID NO:12 and comprises a light chain variable domain having at least 90% identity to the amino acid sequence of SEQ ID NO:17.

In another embodiment the targeted binding agent or antibody, or antigen-binding portion thereof, comprises a heavy chain sequence comprising the sequence of SEQ ID NO.:22. In another embodiment, the targeted binding agent or antibody, or antigen-binding portion thereof, further comprises a light chain sequence comprising the sequence of SEQ ID NO.:27. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:22 and comprises a light chain variable domain having at least 90% identity to the amino acid sequence of SEQ ID NO:27.

In another embodiment the targeted binding agent or antibody, or antigen-binding portion thereof, comprises a heavy chain sequence comprising the sequence of SEQ ID NO.:32. In another embodiment, the targeted binding agent or antibody, or antigen-binding portion thereof, further comprises a light chain sequence comprising the sequence of SEQ ID NO.:37. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:32 and comprises a light chain variable domain having at least 90% identity to the amino acid sequence of SEQ ID NO:37.

In another embodiment the targeted binding agent or antibody, or antigen-binding portion thereof, comprises a heavy chain sequence comprising the sequence of SEQ ID NO.:42. In another embodiment, the targeted binding agent or antibody, or antigen-binding portion thereof, further comprises a light chain sequence comprising the sequence of SEQ ID NO.:47. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:42 and comprises a light chain variable domain having at least 90% identity to the amino acid sequence of SEQ ID NO:47.

In another embodiment the targeted binding agent or antibody, or antigen-binding portion thereof, comprises a heavy chain sequence comprising the sequence of SEQ ID NO.:52. In another embodiment, the targeted binding agent or antibody, or antigen-binding portion thereof, further comprises a light chain sequence comprising the sequence of SEQ ID NO.:57. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:52 and comprises a light chain variable domain having at least 90% identity to the amino acid sequence of SEQ ID NO:57.

In another embodiment the targeted binding agent or antibody, or antigen-binding portion thereof, comprises a heavy chain sequence comprising the sequence of SEQ ID NO.:62. In another embodiment, the targeted binding agent or antibody, or antigen-binding portion thereof, further comprises a light chain sequence comprising the sequence of SEQ ID NO.:67. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:62 and comprises a light chain variable domain having at least 90% identity to the amino acid sequence of SEQ ID NO:67.

In another embodiment the targeted binding agent or antibody, or antigen-binding portion thereof, comprises a heavy chain sequence comprising the sequence of SEQ ID NO.:72. In another embodiment, the targeted binding agent or antibody, or antigen-binding portion thereof, further comprises a light chain sequence comprising the sequence of SEQ ID NO.:77. In some embodiments, the antibody is a fully human monoclonal antibody.

In another embodiment the targeted binding agent or antibody, or antigen-binding portion thereof, comprises a heavy chain variable domain having at least 90% identity to the amino acid of SEQ ID NO:72 and comprises a light chain variable domain having at least 90% identity to the amino acid sequence of SEQ ID NO:77.

In one embodiment, the targeted binding agent or antibody comprises variants or derivatives of the CDRs disclosed herein, the contiguous sequences spanning the framework regions and CDRs (specifically from FR1 through FR4 or CDR1 through CDR3), the light or heavy chain sequences disclosed herein, or the antibodies disclosed herein. Variants include targeted binding agents or antibodies comprising sequences which have as many as twenty, sixteen, ten, nine or fewer, e.g. one, two, three, four, five or six amino acid additions, substitutions, deletions, and/or insertions in any of the CDR1, CDR2 or CDR3s as shown in Table 8 or Table 9, the contiguous sequences spanning the framework regions and CDRs (specifically from FR1 through FR4 or CDR1 through CDR3) as shown in Table 8 or Table 9, the light or heavy chain sequences disclosed herein, or with the monoclonal antibodies disclosed herein. Variants include targeted binding agents or antibodies comprising sequences which have one, two or three, amino acid additions, substitutions, deletions, and/or insertions in any of the CDR1, CDR2 or CDR3s as shown in Table 8 or Table 9, the contiguous sequences spanning the framework regions and CDRs (specifically from FR1 through FR4 or CDR1 through CDR3) as shown in Table 8 or Table 9, the light or heavy chain sequences disclosed herein, or with the monoclonal antibodies disclosed herein. Variants include targeted binding agents or antibodies comprising sequences which have at least about 60, 70, 80, 85, 90, 95, 98 or about 99% amino acid sequence identity with any of the CDR1, CDR2 or CDR3s as shown in Table 8 or Table 9, the contiguous sequences spanning the framework regions and CDRs (specifically from FR1 through FR4 or CDR1 through CDR3) as shown in Table 8 or Table 9, the light or heavy chain sequences disclosed herein, or with the monoclonal antibodies disclosed herein.

The percent identity of two amino acid sequences can be determined by any method known to one skilled in the art, including, but not limited to, pairwise protein alignment. In one embodiment variants comprise changes in the CDR sequences or light or heavy chain sequences disclosed herein that are naturally occurring or are introduced by in vitro engineering of native sequences using recombinant DNA techniques or mutagenesis techniques. Naturally occurring variants include those which are generated in vivo in the corresponding germline nucleotide sequences during the generation of an antibody to a foreign antigen.

In one embodiment variants include targeted binding agents or antibodies comprising sequences which have (a) a VH CDR1 having an amino acid sequence identical to or comprising 1, 2, or 3 amino acid residue substitutions relative to SEQ ID NO: 3;

(b) a VH CDR2 having an amino acid sequence identical to or comprising 1, 2, or 3 amino acid residue substitutions relative to SEQ ID NO: 4;

(c) a VH CDR3 having an amino acid sequence identical to or comprising 1, 2, or 3 amino acid residue substitutions relative to SEQ ID NO: 5;

(d) a VL CDR1 having an amino acid sequence identical to or comprising 1, 2, or 3 amino acid residue substitutions relative to VL CDR1 of SEQ ID NO: 8;

(e) a VL CDR2 having an amino acid sequence identical to or comprising 1, 2, or 3 amino acid residue substitutions relative to SEQ ID NO: 9; and (f) a VL CDR3 having an amino acid sequence identical to or comprising 1, 2, or 3 amino acid residue substitutions relative to SEQ ID NO: 10.

In another embodiment, variants include targeted binding agents or antibodies comprising sequences which have (a) a VH CDR1 having an amino acid sequence identical to or comprising 1, 2, or 3 amino acid residue substitutions relative to SEQ ID NO: 23;

(b) a VH CDR2 having an amino acid sequence identical to or comprising 1, 2, or 3 amino acid residue substitutions relative to SEQ ID NO: 24;

(c) a VH CDR3 having an amino acid sequence identical to or comprising 1, 2, or 3 amino acid residue substitutions relative to SEQ ID NO: 25;

(d) a VL CDR1 having an amino acid sequence identical to or comprising 1, 2, or 3 amino acid residue substitutions relative to VL CDR1 of SEQ ID NO: 28;

(e) a VL CDR2 having an amino acid sequence identical to or comprising 1, 2, or 3 amino acid residue substitutions relative to SEQ ID NO: 29; and (f) a VL CDR3 having an amino acid sequence identical to or comprising 1, 2, or 3 amino acid residue substitutions relative to SEQ ID NO: 30.

In one embodiment the derivative may be a heteroantibody, that is an antibody in which two or more antibodies are linked together. Derivatives include antibodies which have been chemically modified. Examples include covalent attachment of one or more polymers, such as water-soluble polymers, N-linked, or O-linked carbohydrates, sugars, phosphates, and/or other such molecules.

The derivatives are modified in a manner that is different from naturally occurring or starting antibody, either in the type or location of the molecules attached. Derivatives further include deletion of one or more chemical groups which are naturally present on the antibody.

In some embodiments of the invention, the targeted binding agent or antibody comprises a sequence comprising SEQ ID NO.: 2. In some embodiments of the invention, the targeted binding agent or antibody comprises a sequence comprising SEQ ID NO.: 2, wherein SEQ ID NO.: 2 comprises any one of the unique combinations of germline and non-germline residues indicated by each row of Table 10. In some embodiments of the invention, the targeted binding agent or antibody comprises a sequence comprising SEQ ID NO.: 2, wherein SEQ ID NO.: 2 comprises any one, any two, any three, any four or all five of the germline residues as indicated in Table 10. In some embodiments of the invention, the targeted binding agent or antibody comprises a sequence comprising SEQ ID NO.: 2, wherein SEQ ID NO.: 2 comprises any one of the unique combinations of germline and non-germline residues indicated by each row of Table 10. In some embodiments of the invention, the targeted binding agent or antibody comprises a sequence comprising SEQ ID NO.: 2, wherein SEQ ID NO.: 2 comprises any one, any two, any three, any four, any five, or all five of the germline residues as indicated in Table 10.

In some embodiments of the invention, the targeted binding agent or antibody comprises a sequence comprising SEQ ID NO.: 7, wherein SEQ ID NO.: 7 comprises any one of the unique combinations of germline and non-germline residues indicated by each row of Table 11 and any one of the unique combinations of germline and non-germline residues indicated by each row of Table 11. In some embodiments of the invention, the targeted binding agent or antibody comprises a sequence comprising SEQ ID NO.: 7, wherein SEQ ID NO.: 7 comprises any one, any two, any three, any four, any five, for all five of the germline residues as indicated in Table 11.

In some embodiments of the invention, the targeted binding agent or antibody comprises a sequence comprising SEQ ID NO.: 12. In some embodiments of the invention, the targeted binding agent or antibody comprises a sequence comprising SEQ ID NO.: 12, wherein SEQ ID NO.: 12 comprises any one of the unique combinations of germline and non-germline residues indicated by each row of Table 12. In some embodiments of the invention, the targeted binding agent or antibody comprises a sequence comprising SEQ ID NO.: 12, wherein SEQ ID NO.: 12 comprises any one, any two or all two of the germline residues as indicated in Table 12.

In some embodiments of the invention, the targeted binding agent or antibody comprises a sequence comprising SEQ ID NO.: 17. In some embodiments of the invention, the targeted binding agent or antibody comprises a sequence comprising SEQ ID NO.: 17, wherein SEQ ID NO.: 17 comprises any one of the unique combinations of germline and non-germline residues indicated by each row of Table 13. In some embodiments of the invention, the targeted binding agent or antibody comprises a sequence comprising SEQ ID NO.: 17, wherein SEQ ID NO.: 17 comprises any one, any two, any three, any four or all four of the germline residues as indicated in Table 13.

In some embodiments of the invention, the targeted binding agent or antibody comprises a sequence comprising SEQ ID NO.: 27. In some embodiments of the invention, the targeted binding agent or antibody comprises a sequence comprising SEQ ID NO.: 27, wherein SEQ ID NO.: 27 comprises any one of the unique combinations of germline and non-germline residues indicated by each row of Table 14. In some embodiments of the invention, the targeted binding agent or antibody comprises a sequence comprising SEQ ID NO.: 27, wherein SEQ ID NO.: 27 comprises any one, any two, any three or all three of the germline residues as indicated in Table 14.

A further embodiment of the invention is a targeted binding agent or antibody which competes for binding to B7-H1 with the targeted binding agent or antibodies of the invention. In another embodiment of the invention there is an antibody which competes for binding to B7-H1 with the targeted binding agent or antibodies of the invention. In another embodiment the targeted binding agent or antibody competes for binding to B7-H1 with any one of fully human monoclonal antibodies 2.7A4, 2.14H9 or 2.9D10, 2.7A4OPT or 2.14H9OPT. "Competes" indicates that the targeted binding agent or antibody competes for binding to B7-H1 with any one of fully human monoclonal antibodies 2.7A4, 2.14H9 or 2.9D10, 2.7A4OPT or 2.14H9OPT, i.e. competition is unidirectional.

Embodiments of the invention include a targeted binding agent or antibody which cross competes with any one of fully human monoclonal antibodies 2.7A4, 2.14H9 or 2.9D10, 2.7A4OPT or 2.14H9OPT for binding to B7-H1. "Cross competes" indicates that the targeted binding agent or antibody competes for binding to B7-H1 with any one of fully human monoclonal antibodies 2.7A4, 2.14H9 or 2.9D10, 2.7A4OPT or 2.14H9OPT, and vice versa, i.e. competition is bidirectional.

A further embodiment of the invention is a targeted binding agent or antibody that binds to the same epitope or epitopes on the extracellular domain of human B7-H1 as the targeted binding agent or antibodies of the invention.

Embodiments of the invention also include a targeted binding agent or antibody that binds to the same epitope or epitopes on the extracellular domain of human B7-H1 as any one of fully human monoclonal antibodies 2.7A4, 2.14H9 or 2.9D10, 2.7A4OPT or 2.14H9OPT.

In one embodiment, the targeted binding agent or antibody binds an epitope on human B7-H1 including at least one or more of the following amino acids selected from the group consisting of Asp at position 122 and Arg at position 125. In another embodiment, an antibody of the invention binds an epitope on human B7-H1 comprising at least two of the following three amino acid residues of Asp at position 122, Arg at position 125 and Arg at position 113. In another embodiment, the antibody binds an epitope on human B7-H1, wherein the antibody exhibits no binding to Ile at position 54, Ser at position 117 and Ala at position 121 on human B7-H1. In yet a further embodiment, an antibody of the invention loses its ability to bind to human B7-H1 if the Arg at position 113 is mutated to an Ala, or to a Tyr, or to a Leu as determined by a competition assay as compared to binding to wild-type B7-H1. In yet a further embodiment, an antibody of the invention loses its ability to bind to human B7-H1 if the Arg at position 125 is mutated to an Ala, or to a Gln, or to a Ser as determined by a competition assay as compared to binding to wild-type B7-H1. In yet a further embodiment, an antibody of the invention retains its ability to bind to human B7-H1 if the Arg at position 123 is mutated to an Ala, or to a Phe, or to a Thr as determined by a competition assay as compared to binding to wild-type B7-H1. In this example, the antibody is 2.14H9. In another example, the antibody is 2.14H9OPT.

In one embodiment, the targeted binding agent or antibody binds an epitope on the extracellular domain of human B7-H1 comprising at least one or more of the following amino acids Asp at position 122 and Thr at position 20. In one embodiment, the antibody binds at least two of the following three amino acid residues of Phe at position 19, Thr at position 20 and Asp at position 122 on human B7-H1. In another embodiment, the shows no binding to at least one of the following three amino acid residues of Ile at position 54, Met at position 115, Ser at position 117 and Ala at position 121 on human B7-H1. In yet a further embodiment, an antibody of the invention loses its ability to bind to human B7-H1 if the Phe at position 19 is mutated to an Ala, or to a Gly, or to a Ser as determined by a competition assay as compared to binding to wild-type B7-H1. In yet a further embodiment, an antibody of the invention loses its ability to bind to human B7-H1 if the Thr at position 20 is mutated to an Ala, or to a Val, or to a Asp as determined by a competition assay as compared to binding to wild-type B7-H1. In yet a further embodiment, an antibody of the invention loses its ability to bind to human B7-H1 if the Asp at position 122 is mutated to an Asn, or to a Glu as determined by a competition assay as compared to binding to wild-type B7-H1. In yet a further embodiment, an antibody of the invention retains its ability to bind to human B7-H1 if the Arg at position 123 is mutated to an Ala, or to a Phe, or to a Thr as determined by a competition assay as compared to binding to wild-type B7-H1. In one example, the antibody is 2.7A4. In another example, the antibody is 2.7A4OPT.

In one embodiment, the targeted binding agent is a bispecific antibody. A bispecific antibody is an antibody that has binding specificity for at least two different epitopes on the same or on different proteins. Methods for making bispecific antibodies are known in the art. (See, for example, Millstein et al., *Nature,* 305:537-539 (1983); Traunecker et al., *EMBO J,* 10:3655-3659 20 (1991); Suresh et al., *Methods in Enzymology,* 121:210 (1986); Kostelny et al., *J. Immunol.,* 148(5):1547-1553 (1992); Hollinger et al., *Proc. Natl Acad. Sci. USA,* 90:6444-6448 (1993); Gruber et al., *J Immunol.,* 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.) Embodiments of the invention described herein relate to monoclonal antibodies that specifically bind B7-H1 and affect B7-H1 function. Other embodiments relate to fully human antibodies that specifically bind B7-H1 and preparations thereof with desirable properties from a therapeutic perspective, including high binding affinity for B7-H1, high selectivity for inhibition of B7-H1 signaling, low toxicity, the ability to block PD-1 receptor activity, the ability to inhibit B7-H1-induced tumour cell survival through immune suppression, the ability to inhibit B7-H1 mediated repression of anti-tumour immunity, which may in turn inhibit proliferation or invasion-related diseases include neoplastic diseases, and/or the ability of tumour cells to grow in vitro and in vivo. Still other embodiments relate to a method of repressing B7-H1-mediated T cell inhibition in an animal by administering to an animal in need thereof an effective amount of a composition comprising the antibodies of the invention. Still other embodiments relate to fully human antibodies that specifically bind B7-H1 and preparations thereof that do not result in a significant Human Anti-Chimeric Antibody (HACA) response, thereby allowing for repeated administration.

In one embodiment of the invention there is provided nucleic acid molecule encoding any of the targeted binding agents or antibodies of the invention. In one embodiment is a nucleic acid molecule encoding the light chain or the heavy chain of an antibody of the invention. In one embodiment, the nucleic acid molecule encodes the light chain or the heavy chain of a fully human monoclonal antibody of any of the antibodies described herein. In one embodiment, the nucleic acid molecule encodes the light chain or the heavy chain of any one of the fully human monoclonal antibodies 2.7A4, 2.14H9, 2.9D10, 2.7A4OPT and 2.14H9OPT. In another embodiment, the nucleic acid molecule encodes the light chain and the heavy chain of any one of the fully human monoclonal antibodies 2.7A4, 2.14H9, 2.9D10, 2.7A4OPT and 2.14H9OPT. The invention also encompasses polynucleotides that hybridize under stringent or lower stringency hybridization conditions, as defined herein, to polynucleotides that encode any of the targeted binding agents or antibodies described herein.

In another embodiment of the invention there is provided a vector comprising a nucleic acid molecule or molecules as described hereinabove, wherein the vector encodes a targeted binding agent as described hereinabove. In one embodiment of the invention there is provided a vector comprising a nucleic acid molecule or molecules as described hereinabove, wherein the vector encodes a light chain and/or a heavy chain of an antibody as defined hereinabove. In one embodiment, the vector comprises a nucleic acid molecule encoding the light chain and/or the heavy chain of a fully human monoclonal antibody. In one embodiment, the vector comprises a nucleic acid molecule encoding the light chain or the heavy chain of any one of the fully human monoclonal antibodies 2.7A4, 2.14H9, 2.9D10, 2.7A4OPT and 2.14H9OPT. In another embodiment, the vector comprises a nucleic acid molecule encoding the light chain and the heavy chain of any one of the fully human monoclonal antibodies 2.7A4, 2.14H9, 2.9D10, 2.7A4OPT and 2.14H9OPT.

In a further embodiment there is provided a host cell transformed with any of the nucleic acid molecules as described hereinabove. In another embodiment of the invention there is provided a host cell comprising the vector comprising the nucleic acid molecule as described hereinabove. In one embodiment the host cell may comprise more than one vector.

As known in the art, antibodies can advantageously be, for example, polyclonal, oligoclonal, monoclonal, chimeric, humanised, and/or fully human antibodies.

It will be appreciated that embodiments of the invention are not limited to any particular form of an antibody or method of generation or production. In some embodiments of the invention, the targeted binding agent is a binding fragment of a fully human monoclonal antibody. For example, the targeted binding agent can be a full-length antibody (e.g., having an intact human Fc region) or an antibody binding fragment (e.g., a Fab, Fab' or F(ab')$_2$, Fv, dAb or other well known antibody fragment, as described in more detail below). In addition, the antibodies can be single-domain antibodies such as camelid or human single VH or VL domains that bind to B7-H1, such as a dAb fragment.

Embodiments of the invention described herein also provide cells for producing these antibodies. Examples of cells include hybridomas, or recombinantly created cells, such as Chinese hamster ovary (CHO) cells, variants of CHO cells (for example DG44) and NSO cells that produce antibodies against B7-H1. Additional information about variants of CHO cells can be found in Andersen and Reilly (2004) *Current Opinion in Biotechnology* 15, 456-462 which is incorporated herein in its entirety by reference. The antibody can be manufactured from a hybridoma that secretes the antibody, or from a recombinantly engineered cell that has been transformed or transfected with a gene or genes encoding the antibody.

In addition, one embodiment of the invention is a method of producing a targeted binding agent or an antibody of the invention by culturing host cells under conditions wherein a nucleic acid molecule is expressed to produce the targeted binding agent or antibody followed by recovery of the targeted binding agent or antibody. In one embodiment is a method of producing an antibody of the invention by culturing host cells under conditions wherein a nucleic acid molecule is expressed to produce the antibody, followed by recovery of the antibody. Still other embodiments include an antibody of the invention produced by the method of culturing a host cell which expresses an antibody encoded by a nucleic acid molecule encoding an antibody of the invention, and isolating said antibody from said culture.

It should be realised that embodiments of the invention also include any nucleic acid molecule which encodes an antibody or fragment of an antibody of the invention including nucleic acid sequences optimised for increasing yields of antibodies or fragments thereof when transfected into host cells for antibody production.

A further embodiment herein includes a method of producing antibodies that specifically bind to B7-H1 and inhibit the biological activity of B7-H1, by immunising a mammal with cells expressing B7-H1, isolated cell membranes containing B7-H1, purified B7-H1, or a fragment thereof, and/or one or more orthologous sequences or fragments thereof.

A further embodiment herein includes a method of producing high affinity antibodies that specifically bind to B7-H1 and inhibit the biological activity of B7-H1, by immunising a mammal with cells expressing B7-H1, isolated cell membranes containing B7-H1, purified B7-H1, or a fragment thereof, and/or one or more orthologous sequences or fragments thereof.

Other embodiments are based upon the generation and identification of isolated antibodies that bind specifically to B7-H1 and inhibit the biological activity of B7-H1. B7-H1 is expressed on a number of tumour types. Antibodies that specifically bind to B7-H1 can prevent B7-H1-mediated tumour cell survival and inhibit B7-H1 mediated repression of anti-tumour immune responses through immune suppression, this can in turn reduce tumour cell invasion, metastasis, tumour growth, and other properties.

In addition, the antibody can be manufactured from a hybridoma that secretes the antibody, or from a recombinantly engineered cell that has been transformed or transfected with a gene or genes encoding the antibody.

In one embodiment there is a hybridoma that produces the targeted binding agent or antibody of the invention. In one embodiment there is a hybridoma that produces the light chain and/or the heavy chain of an antibody of the invention. In one embodiment the hybridoma may produce a light chain and/or a heavy chain of a fully human monoclonal antibody. In another embodiment, the hybridoma produces the light chain and/or the heavy chain of the fully human monoclonal antibody 2.7A4, 2.14H9, 2.9D10, 2.7A4OPT and 2.14H9OPT. Alternatively the hybridoma may produce an antibody that binds to the same epitope or epitopes as fully human monoclonal antibody 2.7A4, 2.14H9, 2.9D10, 2.7A4OPT and 2.14H9OPT. Alternatively the hybridoma may produce an antibody that competes for binding to B7-H1 with fully human monoclonal antibody 2.7A4, 2.14H9, 2.9D10, 2.7A4OPT and 2.14H9OPT. Alternatively the hybridoma may produce an antibody that cross-competes for binding to B7-H1 with fully human monoclonal antibody 2.7A4, 2.14H9, 2.9D10, 2.7A4OPT and 2.14H9OPT.

In other embodiments the invention provides compositions, including a targeted binding agent or antibody of the invention or binding fragment thereof, and a pharmaceutically acceptable carrier.

Still further embodiments of the invention include methods of treating a proliferative or invasion-related disease in an animal by administering to the animal a therapeutically effective dose of a targeted binding agent of the invention. In certain embodiments the method further comprises selecting an animal in need of treatment for a proliferative or invasion-related disease, and administering to the animal a therapeutically effective dose of a targeted binding agent of the invention. In certain embodiments, the animal is human. In certain embodiments, the targeted binding agent is a fully human monoclonal antibody. In certain embodiments, the targeted binding agent is an antibody of the invention and may be selected from the group consisting of 2.7A4, 2.14H9 or 2.9D10, 2.7A4OPT or 2.14H9OPT.

Still further embodiments of the invention include methods of inhibiting cell proliferation or invasion-related disease, with a B7-H1 mediated component, in an animal by administering to the animal a therapeutically effective dose of a targeted binding agent of the invention. In certain embodiments the method further comprises selecting an animal in need of treatment for proliferation or invasion-related disease, with a B7-H1 mediated component, and administering to said animal a therapeutically effective dose of a targeted binding agent of the invention. In certain embodiments, the animal is human. In certain embodiments, the targeted binding agent is a fully human monoclonal antibody. In certain embodiments, the targeted binding agent is an antibody of the invention and may be selected from the group consisting of 2.7A4, 2.14H9 or 2.9D10, 2.7A4OPT or 2.14H9OPT.

Still further embodiments of the invention include methods of inhibiting tumour cell invasion, cellular metastasis or tumour growth in an animal by administering to the animal a therapeutically effective dose of a targeted binding agent of the invention. In certain embodiments the method further comprises selecting an animal in need of treatment for tumour cell, invasion, cellular metastasis or tumour growth, and administering to the animal a therapeutically effective dose of a targeted binding agent of the invention. In certain embodiments, the animal is human. In certain embodiments, the targeted binding agent is a fully human monoclonal antibody. In certain embodiments, the targeted binding agent is an antibody of the invention and may be selected from the group consisting of 2.7A4, 2.14H9 or 2.9D10, 2.7A4OPT or 2.14H9OPT.

Still further embodiments of the invention include methods of treating an animal suffering from a neoplastic disease by administering to the animal a therapeutically effective dose of a targeted binding agent of the invention. In certain embodiments the method further comprises selecting an animal in need of treatment for a neoplastic disease, and administering to the animal a therapeutically effective dose of a targeted binding agent of the invention.

Still further embodiments of the invention include methods of treating an animal suffering from a non-neoplastic disease by administering to the animal a therapeutically effective dose of a targeted binding agent of the invention. In certain embodiments the method further comprises selecting an animal in need of treatment for a non-neoplastic disease, and administering to the animal a therapeutically effective dose of a targeted binding agent of the invention.

Still further embodiments of the invention include methods of treating an animal suffering from chronic viral infection by administering to the animal a therapeutically effective dose of a targeted binding agent of the invention. In certain embodiments the method further comprises selecting an animal in need of treatment for chronic viral infection, and administering to the animal a therapeutically effective dose of a targeted binding agent of the invention.

Still further embodiments of the invention include methods of treating an animal suffering from a malignant tumour by administering to the animal a therapeutically effective dose of a targeted binding agent of the invention. In certain embodiments the method further comprises selecting an animal in need of treatment for a malignant tumour, and administering to the animal a therapeutically effective dose of a targeted binding agent of the invention.

Still further embodiments of the invention include methods of treating an animal suffering from a disease or condition associated with B7-H1 expression by administering to the animal a therapeutically effective dose of a targeted binding agent of the invention. In certain embodiments the method further comprises selecting an animal in need of treatment for a disease or condition associated with B7-H1 expression, and administering to the animal a therapeutically effective dose of a targeted binding agent of the invention.

A malignant tumour may be selected from the group consisting of: solid tumours such as melanoma, skin cancers, small cell lung cancer, non-small cell lung cancer, glioma, hepatocellular (liver) carcinoma, gallbladder cancer, thyroid tumour, bone cancer, gastric (stomach) cancer, prostate cancer, breast cancer, ovarian cancer, cervical cancer, uterine cancer, vulval cancer, endometrial cancer, testicular cancer, bladder cancer, lung cancer, glioblastoma, endometrial cancer, kidney cancer, renal cell carcinoma, colon cancer, colorectal, pancreatic cancer, esophageal carcinoma, brain/CNS cancers, head and neck cancers, neuronal cancers, mesothelioma, sarcomas, biliary (cholangiocarcinoma), small bowel adenocarcinoma, pediatric malignancies, epidermoid carcinoma, sarcomas, cancer of the pleural/peritoneal membranes and leukaemia, including acute myeloid leukaemia, acute lymphoblastic leukaemia, and multiple myeloma.

Treatable proliferative or invasion-related diseases include neoplastic diseases, such as, melanoma, skin cancer, small cell lung cancer, non-small cell lung cancer, salivary gland, glioma, hepatocellular (liver) carcinoma, gallbladder cancer, thyroid tumour, bone cancer, gastric (stomach) cancer, prostate cancer, breast cancer, ovarian cancer, cervical cancer, uterine cancer, vulval cancer, endometrial cancer, testicular cancer, bladder cancer, lung cancer, glioblastoma, thyroid cancer, endometrial cancer, kidney cancer, colon cancer, colorectal cancer, pancreatic cancer, esophageal carcinoma, brain/CNS cancers, neuronal cancers, head and neck cancers, mesothelioma, sarcomas, biliary (cholangiocarcinoma), small bowel adenocarcinoma, pediatric malignancies, epidermoid carcinoma, sarcomas, cancer of the pleural/peritoneal membranes and leukaemia, including acute myeloid leukaemia, acute lymphoblastic leukaemia, and multiple myeloma. Treatable chronic viral infections include HIV, hepatitis B virus (HBV), and hepatitis C virus (HCV) in humans, simian immunodeficiency virus (SIV) in monkeys, and lymphocytic choriomeningitis virus (LCMV) in mice.

Disease-related cell invasion and/or proliferation may be any abnormal, undesirable or pathological cell invasion and/or proliferation, for example tumour-related cell invasion and/or proliferation.

In one embodiment, the neoplastic disease is a solid tumour selected from any one of the following carcinomas of the breast, colon, colorectal, prostate, stomach, gastric, ovary, esophagus, pancreas, gallbladder, non-small cell lung cancer, thyroid, endometrium, head and neck, renal, renal cell carcinoma, bladder and gliomas.

In one embodiment the present invention is suitable for use in inhibiting B7-H1, in patients with a tumour which is dependent alone, or in part, on B7-H1.

Still further embodiments of the invention include use of a targeted binding agent or antibody of the invention in the preparation of a medicament for the treatment of an animal suffering from a proliferative or invasion-related disease. In certain embodiments the use further comprises selecting an animal in need of treatment for a proliferative or invasion-related disease.

Still further embodiments of the invention include use of a targeted binding agent or antibody of the invention in the preparation of medicament for the treatment of proliferation or invasion-related disease, with a B7-H1 mediated component, in an animal. In certain embodiments the use further comprises selecting an animal in need of treatment for proliferation or invasion-related disease, with a B7-H1 mediated component.

Still further embodiments of the invention include use of a targeted binding agent or antibody of the invention in the preparation of medicament for the treatment of tumour cell invasion, cellular metastasis or tumour growth in an animal. In certain embodiments the use further comprises selecting an animal in need of treatment for tumour cell invasion, cellular metastasis or tumour.

Still further embodiments of the invention include use of a targeted binding agent or antibody of the invention in the preparation of a medicament for the treatment of an animal suffering from a neoplastic disease. In certain embodiments the use further comprises selecting an animal in need of treatment for a neoplastic disease.

Still further embodiments of the invention include use of a targeted binding agent or antibody of the invention in the preparation of a medicament for the treatment of an animal suffering from a disease where the etiology is associated with an infectious agent, such as, for example, hepatocellular cancer, gastric cancer, or cervical cancer. In certain embodiments the use further comprises selecting an animal in need of treatment for a neoplastic disease.

Still further embodiments of the invention include use of a targeted binding agent or antibody of the invention in the preparation of a medicament for the treatment of an animal suffering from a non-neoplastic disease. In certain embodiments the use further comprises selecting an animal in need of treatment for a non-neoplastic disease.

Still further embodiments of the invention include use of a targeted binding agent or antibody of the invention in the preparation of a medicament for the treatment of an animal suffering from chronic viral infection. In certain embodiments the use further comprises selecting an animal in need of treatment for a non-neoplastic disease. In still other embodiments, the use further comprises ocular disease, inflammatory disease, cardiovascular disease and sepsis.

Still further embodiments of the invention include use of a targeted binding agent or antibody of the invention in the preparation of a medicament for the treatment of an animal suffering from a malignant tumour. In certain embodiments the use further comprises selecting an animal in need of treatment for a malignant tumour.

Still further embodiments of the invention include use of a targeted binding agent or antibody of the invention in the preparation of a medicament for the treatment of an animal suffering from a disease or condition associated with B7-H1 expression. In certain embodiments the use further comprises selecting an animal in need of treatment for a disease or condition associated with B7-H1 expression.

Still further embodiments of the invention include a targeted binding agent or antibody of the invention for use as a medicament for the treatment of an animal suffering from a proliferative or invasion-related disease.

Still further embodiments of the invention include a targeted binding agent or antibody of the invention for use as a medicament for the treatment of an animal suffering from tumour cell invasion, cellular metastasis or tumour growth in an animal.

Still further embodiments of the invention include a targeted binding agent or antibody of the invention for use as a medicament for the treatment of an animal suffering from a disease or condition associated with B7-H1 expression.

In one embodiment treatment of
a proliferative or invasion-related disease;
a neoplastic disease;
a non-neoplastic disease;
a malignant tumour; or
chronic viral infection; or
a disease or condition associated with B7-H1 expression, comprises managing, ameliorating, preventing, any of the aforementioned diseases or conditions.

In one embodiment treatment of a neoplastic disease comprises inhibition of tumour growth, tumour growth delay, regression of tumour, shrinkage of tumour, increased time to regrowth of tumour on cessation of treatment, increased time to tumour recurrence, slowing of disease progression.

In one embodiment treatment of a disease or condition associated with B7-H1 expression comprises inhibiting the growth of cells that express B7-H1.

In some embodiments, following administration of the targeted binding agent or antibody of the invention, a clearing agent is administered, to remove excess circulating antibody from the blood.

In some embodiments of the invention, the animal to be treated is a human.

In some embodiments of the invention, the targeted binding agent is a fully human monoclonal antibody.

In some embodiments of the invention, the targeted binding agent is selected from the group consisting of fully human monoclonal antibodies 2.7A4, 2.14H9 and 2.9D10.

Embodiments of the invention include a conjugate comprising the targeted binding agent as described herein, and a therapeutic agent. In some embodiments of the invention, the therapeutic agent is a toxin. In other embodiments, the therapeutic agent is a radioisotope. In still other embodiments, the therapeutic agent is a pharmaceutical composition.

In another aspect, a method of selectively killing a cancerous cell in a patient is provided. The method comprises administering a fully human antibody conjugate to a patient. The fully human antibody conjugate comprises an antibody that can bind to B7-H1 and an agent. The agent is either a toxin, a radioisotope, or another substance that will kill a cancer cell. The antibody conjugate thereby selectively kills the cancer cell.

In one aspect, a conjugated fully human antibody that specifically binds to B7-H1 is provided. Attached to the antibody is an agent, and the binding of the antibody to a cell results in the delivery of the agent to the cell. In one embodiment, the above conjugated fully human antibody binds to an extracellular domain of B7-H1. In another embodiment, the antibody and conjugated toxin are internalised by a cell that expresses B7-H1. In another embodiment, the agent is a cytotoxic agent. In another embodiment, the agent is, for example saporin, or auristatin, pseudomonas exotoxin, gelonin, ricin, calicheamicin or maytansine-based immunoconjugates, and the like. In still another embodiment, the agent is a radioisotope.

The targeted binding agent or antibody of the invention can be administered alone, or can be administered in combination with additional antibodies or chemotherapeutic drugs or radiation therapy or therapeutic vaccines. For example, a monoclonal, oligoclonal or polyclonal mixture of B7-H1 antibodies that block B7-H1 mediated repression of anti-tumour immunity can be administered in combination with a drug shown to inhibit tumour cell proliferation.

According to another aspect of the invention there is provided a pharmaceutical composition comprising a targeted binding agent of antibody of the invention and a pharmaceutically acceptable carrier.

Another embodiment of the invention includes a method of diagnosing diseases or conditions in which an antibody as disclosed herein is utilised to detect the presence and/or level of B7-H1 in a patient or patient sample. In one embodiment, the patient sample is blood or blood serum or urine.

In further embodiments, methods for the identification of risk factors, diagnosis of disease, and staging of disease is presented which involves the identification of the expression and/or overexpression of B7-H1 using anti-B7-H1 antibodies. In some embodiments, the methods comprise administering to a patient a fully human antibody conjugate that selectively binds to B7-H1 on a cell. The antibody conjugate comprises an antibody that specifically binds to B7-H1 and a label. The methods further comprise observing the presence of the label in the patient. A relatively high amount of the label will indicate a relatively high risk of the disease and a relatively low amount of the label will indicate a relatively low risk of the disease. In one embodiment, the label is a green fluorescent protein.

The invention further provides methods for assaying for the presence and/or level of B7-H1 in a patient sample, comprising contacting an antibody as disclosed herein with a biological sample from a patient, and detecting the level of binding between said antibody and B7-H1 in said sample. In more specific embodiments, the biological sample is blood, plasma or serum.

Another embodiment of the invention includes a method for diagnosing a condition associated with the expression of B7-H1 in a cell by contacting the serum or a cell with an antibody as disclosed herein, and thereafter detecting the presence of B7-H1. In one embodiment the condition can be a proliferative or invasion-related disease including, but not limited to, a neoplastic disease.

In another embodiment, the invention includes an assay kit for detecting B7-H1 in mammalian tissues, cells, or body fluids. Such a kit would be useful to screen for B7-H1-related diseases. The kit includes a targeted binding agent or antibody of the invention and a means for indicating the reaction of the targeted binding agent or antibody with B7-H1, if present. In one embodiment the antibody is a monoclonal antibody. In one embodiment, the antibody that binds B7-H1 is labeled. In another embodiment the antibody is an unlabeled primary antibody and the kit further includes a means for detecting the primary antibody. In one embodiment, the means for detecting includes a labeled second antibody that is an anti-immunoglobulin. The antibody may be labeled with a marker selected from the group consisting of a fluorochrome, an enzyme, a radionuclide and a radiopaque material.

In some embodiments, the targeted binding agents or antibodies as disclosed herein can be modified to enhance their capability of fixing complement and participating in complement-dependent cytotoxicity (CDC). In other embodiments, the targeted binding agents or antibodies can be modified to enhance their capability of activating effector cells and participating in antibody-dependent cytotoxicity (ADCC). In yet other embodiments, the targeted binding agents or antibodies can be modified both to enhance their capability of activating effector cells and participating in antibody-dependent cytotoxicity (ADCC) and to enhance their capability of fixing complement and participating in complement-dependent cytotoxicity (CDC).

In some embodiments, the targeted binding agents or antibodies as disclosed herein can be modified to reduce their capability of fixing complement and participating in complement-dependent cytotoxicity (CDC). In other embodiments, the targeted binding agents or antibodies can be modified to reduce their capability of activating effector cells and participating in antibody-dependent cytotoxicity (ADCC). In yet other embodiments, the targeted binding agents or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In certain embodiments, the half-life of a targeted binding agent or antibody as disclosed herein and of compositions of the invention is at least about 4 to 7 days. In certain embodiments, the mean half-life of a targeted binding agent or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a targeted binding agent or antibody as disclosed herein and of compositions of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of a targeted binding agent or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/3461.

In another embodiment, the invention provides an article of manufacture including a container. The container includes a composition containing a targeted binding agent or antibody as disclosed herein, and a package insert or label indicating that the composition can be used to treat cell adhesion, invasion, angiogenesis, and/or proliferation-related diseases, including, but not limited to, diseases characterised by the expression or overexpression of B7-H1.

In other embodiments, the invention provides a kit for treating diseases involving the expression of B7-H1, comprising a targeted binding agent or antibody as disclosed herein, and instructions to administer the monoclonal antibodies to a subject in need of treatment.

The present invention provides formulation of proteins comprising a variant Fc region. That is, a non naturally occurring Fc region, for example an Fc region comprising one or more non naturally occurring amino acid residues. Also encompassed by the variant Fc regions of present invention are Fc regions which comprise amino acid deletions, additions and/or modifications.

The serum half-life of proteins comprising Fc regions may be increased by increasing the binding affinity of the Fc region for FcRn. In one embodiment, the Fc variant protein has enhanced serum half life relative to comparable molecule.

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, 235E and 331S, as numbered by the EU index as set forth in Kabat. In a further specific embodiment, an Fc variant of the invention comprises the 234F, 235F, and 331S non naturally occurring amino acid residues, as numbered by the EU index as set forth in Kabat. In another specific embodiment, an Fc variant of the invention comprises the 234F, 235Y, and 331S non naturally occurring amino acid residues, as numbered by the EU index as set forth in Kabat. In another specific embodiment, an Fc variant of the invention comprises the 234F, 235E, and 331S non naturally occurring amino acid residues, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, 235E and 331S, as numbered by the EU index as set forth in Kabat; at least one non naturally occurring amino acid selected from the group consisting of 234F, 235F, and 331S, as numbered by the EU index as set forth in Kabat, and at least one non naturally occurring amino acid at one or more positions are selected from the group consisting of 252Y, 254T and 256E, as numbered by the EU index as set forth in Kabat. As used herein, the "OPT" and "TM" designations are synonymous and are used to describe antibodies of the invention engineered to introduce the three mutations; L234F and L235E in the hinge and P331S in the CH2 domain of the IgG molecule to eliminate its ability to trigger antibody-dependent cell-mediated cytotoxicity and complement-dependent cytotoxicity (Oganesyan V. et al. (2008), Acta Cryst., D64: 700-704).

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, 235E and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, 235E and 331S, as numbered by the EU index as set forth in Kabat; and at least one non naturally occurring amino acid at one or more positions are selected from the group consisting of 252Y, 254T and 256E, as numbered by the EU index as set forth in Kabat.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci.* USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments of the invention, the glycosylation patterns of the antibodies provided herein are modified to enhance ADCC and CDC effector function. See Shields R L et al., (2002) JBC. 277:26733; Shinkawa T et al., (2003) JBC. 278:3466 and Okazaki A et al., (2004) J. Mol. Biol., 336: 1239. In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It is also known in the art that the glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). Accordingly, in one embodiment the Fc regions of the antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867).

BRIEF DESCRIPTION OF THE DRAWINGS

FIG. 8A/B/C are line graphs showing the effect of anti-B7-H1 antibodies of the invention on HPAC cells in a mouse xenograft model.

FIG. 9A/B/C are line graphs showing the effect of anti-B7-H1 antibodies of the invention on A375 cells in a mouse xenograft model.

FIG. 10A/B are line graphs showing the effect of anti-B7-H1 antibodies of the invention on HPAC cells in a mouse xenograft model.

FIG. 12A/B/C/D are line graphs showing the effect of anti-B7-H1 antibodies of the invention on A375 cells in a mouse xenograft model.

FIG. 13A/B are line graphs showing the effect of anti-B7-H1 antibodies of the invention on A375 cells in a mouse xenograft model with and without the presence of T cells.

FIG. 14A/B are line graphs showing the effect of anti-B7-H1 antibodies of the invention on A375 cells in a mouse xenograft model with and without the presence of T cells.

DEFINITIONS

Figure 1:
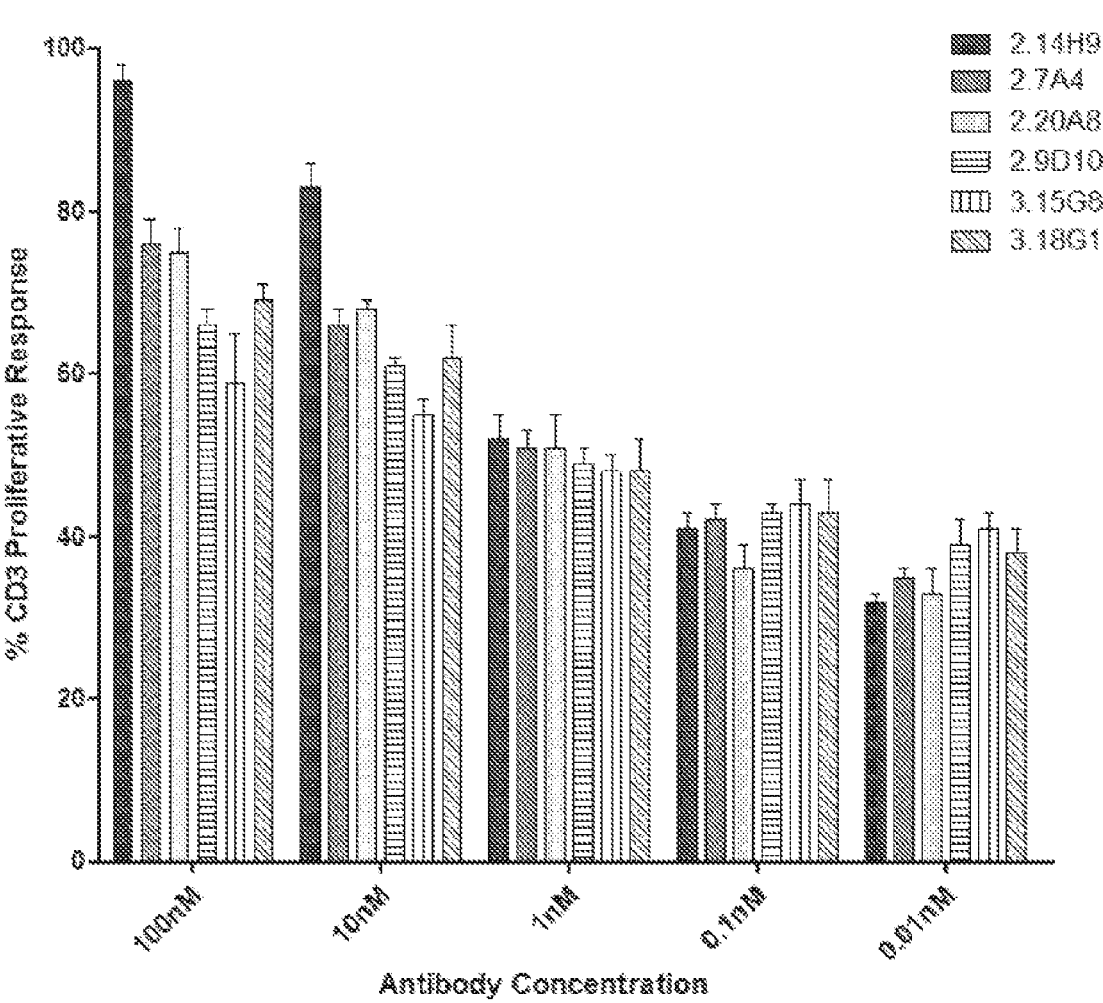
FIG. 1 is a bar graph showing the effects of the anti-B7-H1 antibodies of the invention on T cell proliferation in beads assay.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilised in connection with, and techniques of, cell and tissue culture, molecular biology, and protein and oligo- or polynucleotide chemistry and hybridisation described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See for example, e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilised in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilised in accordance with the present disclosure, the following terms, unless otherwise indicated, shall be understood to have the following meanings:

An antagonist or inhibitor may be a polypeptide, nucleic acid, carbohydrate, lipid, small molecular weight compound, an oligonucleotide, an oligopeptide, RNA interference (RNAi), antisense, a recombinant protein, an antibody, or fragments thereof or conjugates or fusion proteins thereof. For a review of RNAi see Milhavet O, Gary DS, Mattson M P. (Pharmacol Rev. 2003 Dec; 55(4):629-48. Review) and antisense (see Opalinska J B, Gewirtz A M. (Sci STKE. 2003 Oct. 28; 2003 (206):pe47.) A compound refers to any small molecular weight compound with a molecular weight of less than about 2000 Daltons.

The term "B7-H1" refers to the human B7-H, B7H1, B7-H1, B7 homolog 1, CD274 antigen, PDCD1L1, PDCD1LG1, PDCD1 ligand 1, PDL1, PD-L1, Programmed cell death 1 ligand 1 precursor, or Programmed death ligand 1.

The term "neutralising" or "inhibits" when referring to a targeted binding agent, such as an antibody, relates to the ability of said agent to eliminate, reduce, or significantly reduce, the activity of a target antigen. Accordingly, a "neutralising" anti-B7-H1 antibody of the invention is capable of eliminating or significantly reducing the activity of B7-H1. A neutralising, antagonising or inhibiting antibody that specifically binds B7-H1 may, for example, act by blocking the binding of B7-H1 to its cognate ligands. Ideally, a neutralising antibody against B7-H1 inhibits B7-H1 mediated repression of T-cell immunity. A neutralising, antagonising or inhibiting antibody that specifically binds B7-H1 may, for example, act by inhibiting binding of B7-H1 to PD-1 and/or to B7-1.

"Inhibiting the biological activity of B7-H1" encompasses an inhibition of B7-H1 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in comparison with the biological activity in the absence of a targeted binding agent or antibody of the invention.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally occurring.

The term "control sequence" as used herein refers to polynucleotide sequences that are necessary either to effect or to affect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences may include promoters, enhancers, introns, transcription termination sequences, polyadenylation signal sequences, and 5' and '3 untranslated regions. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide, or RNA-DNA heteroduplexes. The term includes single and double stranded forms of DNA.

The term "oligonucleotide" referred to herein includes naturally occurring, and modified nucleotides linked together by naturally occurring, and non naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridise" referred to herein means to detectably and specifically bind. Polynucleotides, oligonucleotides and fragments thereof selectively hybridise to nucleic acid strands under hybridisation and wash conditions that minimise appreciable amounts of detectable binding to nonspecific nucleic acids. High stringency conditions can be used to achieve selective hybridisation conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Stringent hybridization conditions include, but are not limited to, hybridization to filter-bound DNA in 6× sodium chloride/sodium citrate (SSC) (0.9 M NaCl/90 mM NaCitrate, pH 7.0) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximising matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M.O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences". As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerised comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognise sequence motifs and structural conformations that may be used to define structural and functional domains in accordance with the antibodies described herein. Glutaminyl and asparaginyl residues are frequently deamidated to the corresponding glutamyl and aspartyl residues, respectively. These residues are deamidated under neutral or basic conditions. The deamidated form of these residues falls within the scope of this invention.

In general, cysteine residues in proteins are either engaged in cysteine-cysteine disulfide bonds or sterically protected from the disulfide bond formation when they are a part of folded protein region. Disulfide bond formation in proteins is a complex process, which is determined by the redox potential of the environment and specialized thiol-disulfide exchanging enzymes (Creighton, Methods Enzymol. 107, 305-329, 1984; Houee-Levin, Methods Enzymol. 353, 35-44,2002). When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterises the parent sequence). Examples of art-recognised polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. Nature 354:105 (1991), which are each incorporated herein by reference. Additionally, such methods may be used to make amino acid substitutions or deletions of one or more variable region cysteine residues participating in an intrachain disulfide bond to generate antibody molecules lacking one or more intrachain disulfide bonds.

The term "CDR region" or "CDR" is intended to indicate the hypervariable regions of the heavy and light chains of an antibody which confer the antigen-binding specificity to the antibody. CDRs may be defined according to the Kabat system (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognises.

The third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 μlays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Kabat et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3.

Variants of the VH and VL domains and CDRs of the present invention, including those for which amino acid sequences are set out herein, and which can be employed in targeting binding agents and antibodies for B7-H1 can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralisation of an antigen activity relative to known antibodies which are specific for the antigen if the activity is known; specified competitive ability with a known antibody or ligand to the antigen at a specific molar ratio; ability to immunoprecipitate ligand-receptor complex; ability to bind to a specified epitope; linear epitope, e.g. peptide sequence identified using peptide-binding scan, e.g. using peptides screened in linear and/or constrained conformation; conformational epitope, formed by non-continuous residues; ability to modulate a new biological activity of B7-H1, or downstream molecule; ability to bind and/or neutralise B7-H1 and/or for any other desired property. The techniques required to make substitutions within amino acid sequences of CDRs, antibody VH or VL domains and antigen binding sites are available in the art. Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Arup K. & Viswanadhan, Vellarkad N. Combinatorial Library Design and Evaluation Principles, Software, Tools, and Applications in Drug Discovery). In some cases the properties of antibodies can be derived from empirical and theoretical models (for example, analysis of likely contact residues or calculated physicochemical property) of antibody sequence, functional and three-dimensional structures and these properties can be considered singly and in combination. An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimisation experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity or confer other desirable properties.

The term "polypeptide fragment" as used herein refers to a polypeptide that has an amino-terminal and/or carboxy-terminal deletion, but where the remaining amino acid sequence is identical to the corresponding positions in the naturally occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to B7-H1, under suitable binding conditions, (2) ability to block appropriate B7-H1-protein binding, or (3) ability to inhibit B7-H1 activity. Typically, polypeptide analogs comprise a conservative amino acid substitution (or addition or deletion) with respect to the naturally occurring sequence. Analogs typically are at least 20 amino acids long, preferably at least 50 amino acids long or longer, and can often be as long as a full-length naturally occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerised molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclise the peptide.

As used herein "antibody" and "antibodies" (immunoglobulins) may be an oligoclonal antibody, a polyclonal antibody, a monoclonal antibody (including full-length monoclonal antibodies), a camelised antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. An antibody comprises a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. The variable regions of each light/heavy chain pair form an antibody binding site. Such antibodies may be derived from any mammal, including, but not limited to, humans, monkeys, pigs, horses, rabbits, dogs, cats, mice, etc.

The term "antibody" or "antibodies" includes binding fragments of the antibodies of the invention, exemplary fragments include single-chain Fvs (scFv), single-chain antibodies, single domain antibodies, domain antibodies, Fv fragments, Fab fragments, F(ab') fragments, F(ab')2 fragments, antibody fragments that exhibit the desired biological activity, disulfide-stabilised variable region (dsFv), dimeric variable region (Diabody), anti-idiotypic (anti-Id) antibodies (including, e.g., anti-Id antibodies to antibodies of the invention), intrabodies, linear antibodies, single-chain antibody molecules and multispecific antibodies formed from antibody fragments and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Digestion of antibodies with the enzyme, papain, results in two identical antigen-binding fragments, known also as "Fab" fragments, and a "Fc" fragment, having no antigen-binding activity but having the ability to crystallise. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" when used herein refers to a fragment of an antibody that comprises the constant domain of the light chain and the CH1 domain of the heavy chain.

dAb" when used herein refers to a fragment of an antibody that is the smallest functional binding unit of a human antibodies. A "dAb" is a single domain antibody and comprises either the variable domain of an antibody heavy chain (VH domain) or the variable domain of an antibody light chain (VL domain). Each dAb contains three of the six naturally occurring CDRs (Ward et al., Binding activities of a repertoire of single immunoglobulin variable domains secreted from *Escherichia coli. Nature* 341, 544-546 (1989); Holt, et al., Domain antibodies: protein for therapy, *Trends Biotechnol.* 21, 484-49 (2003)). With molecular weights ranging from 11 to 15 kDa, they are four times smaller than a fragment antigen binding (Fab)2 and half the size of a single chain Fv (scFv) molecule.

"Camelid" when used herein refers to antibody molecules are composed of heavy-chain dimers which are devoid of light chains, but nevertheless have an extensive antigen-binding repertoire (Hamers-Casterman C, Atarhouch T, Muyldermans S, Robinson G, Hamers C, Songa E B, Bendahman N, Hamers R (1993) Naturally occurring antibodies devoid of light chains. Nature 363:446-448).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al (1990) Nature, 348, 552-554, Holt et al (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426, Huston et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448,). Fv, scFv or diabody molecules may be stabilised by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see, Kabat et al., Sequences of Proteins of Immunological Interest, 5th Ed. Public Health Service, National Institutes of Health, Bethesda, MD (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, MD (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework" or "FR" residues are those variable domain residues flanking the CDRs. FR residues are present in chimeric, humanized, human, domain antibodies, diabodies, vaccibodies, linear antibodies, and bispecific antibodies.

As used herein, "targeted binding agent", "targeted binding protein", "specific binding protein" and like terms refer to an agent, for example an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. A targeted binding agent may comprise at least one antigen binding domain (e.g. a CDR) of an antibody, wherein said domain is fused or contained within a heterologous protein scaffold, e.g. a non-antibody protein scaffold.

"Binding fragments" of an antibody are produced by recombinant DNA techniques, or by enzymatic or chemical cleavage of intact antibodies. Binding fragments include Fab, Fab', $F(ab')_2$, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics.

An antibody is said to specifically bind an antigen when the dissociation constant is 1 pM, preferably 100 nM and most preferably 10 nM.

The term "agent" is used herein to denote a chemical compound, a mixture of chemical compounds, a biological macromolecule, or an extract made from biological materials.

"Active" or "activity" in regard to a B7-H1 polypeptide refers to a portion of aB7-H1 polypeptide that has a biological or an immunological activity of a native B7-H1 polypeptide. "Biological" when used herein refers to a biological function that results from the activity of the native B7-H1 polypeptide. A preferred B7-H1 biological activity includes, for example, B7-H1 induced cell proliferation, cell adhesion and invasion.

"Mammal" when used herein refers to any animal that is considered a mammal. Preferably, the mammal is human.

"Animal" when used herein encompasses animals considered a mammal. Preferably the animal is human.

The term "patient" includes human and veterinary subjects.

The term "mAb" refers to monoclonal antibody.

"Liposome" when used herein refers to a small vesicle that may be useful for delivery of drugs that may include the B7-H1 polypeptide of the invention or antibodies to such a B7-H1 polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, C, $^{15}$N, $^{35}$S, $^{90}$Y $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxidase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, monocytes, neutrophils, and macrophages) recognise bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarised in Table 9 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *PNAS* (*USA*) 95:652-656 (1988).

"Complement dependent cytotoxicity" and "CDC" refer to the mechanism by which antibodies carry out their cell-killing function. It is initiated by the binding of C1q, a constituent of the first component of complement, to the Fc domain of Igs, IgG or IgM, which are in complex with antigen (Hughs-Jones, N.C., and B. Gardner. 1979. Mol. Immunol. 16:697). C1q is a large, structurally complex glycoprotein of ~410 kDa present in human serum at a concentration of 70 µg/ml (Cooper, N. R. 1985. Adv. Immunol. 37:151). Together with two serine proteases, C1r and C1s, C1q forms the complex C1, the first component of complement. At least two of the N-terminal globular heads of C1q must be bound to the Fc of Igs for C1 activation, hence for initiation of the complement cascade (Cooper, N. R. 1985. Adv. Immunol. 37:151).

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called $\alpha$, $\delta$, $\epsilon$, $\gamma$, and $\mu$, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1, IgG2, IgG3, and IgG4 are known to bind Fc gamma receptors, which mediate various effector functions including ADCC. Human light chain constant regions may be classified into two major classes, kappa and lambda.

If desired, the isotype of an antibody that specifically binds B7-H1 can be switched, for example to take advantage of a biological property of a different isotype. For example, in some circumstances it can be desirable in connection with the generation of antibodies as therapeutic antibodies against B7-H1 that the antibodies be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable in connection with the generation of antibodies as therapeutic antibodies against B7-H1 that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-B7-H1 antibodies discussed herein are fully human antibodies. If an antibody possessed desired binding to B7-H1, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

"Whole blood assays" use unfractionated blood as a source of natural effectors. Blood contains complement in the plasma, together with FcR-expressing cellular effectors, such as polymorphonuclear cells (PMNs) and mononuclear cells (MNCs). Thus, whole blood assays allow simultaneous evaluation of the synergy of both ADCC and CDC effector mechanisms in vitro.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

Exemplary cancers in humans include a bladder tumour, breast tumour, prostate tumour, basal cell carcinoma, biliary tract cancer, bladder cancer, bone cancer, brain and CNS cancer (e.g., glioma tumour), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas.

Exemplary chronic infections in humans include HIV, hepatitis B virus (HBV), and hepatitis C virus (HCV).

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Song-sivilai & Lachmann Clin. Exp. Immunol. 79: 315-321 (1990), Kostelny et al. J. Immunol. 148:1547-1553 (1992). Bispecific antibodies do not exist in the form of fragments having a single binding site (e.g., Fab, Fab', and Fv).

Typically, a VH domain is paired with a VL domain to provide an antibody antigen-binding site, although a VH or VL domain alone may be used to bind antigen. The VH domain (see Table 9) may be paired with the VL domain (see Table 13), so that an antibody antigen-binding site is formed comprising both the VH and VL domains.

Human Antibodies and Humanisation of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilisation of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sised germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Amgen, Inc. (Fremont, California, U.S.A).

Such mice, then, are capable of producing human immunoglobulin molecules and antibodies and are deficient in the production of murine immunoglobulin molecules and antibodies. Technologies utilised for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

The production of the XenoMouse® strains of mice is further discussed and delineated in U.S. patent application Ser. No. 07/466,008, filed Jan. 12, 1990, Ser. No. 07/610, 515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, 08/430,938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilised a "minilocus" approach. In the minilocus approach, an exogenous Ig locus is mimicked through the inclusion of pieces (individual genes) from the Ig locus. Thus, one or more $V_H$ genes, one or more DH genes, one or more JH genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669, 6,023.010 to Krimpenfort and Berns, U.S. Pat. Nos. 5,612, 205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053, 131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XenoMouse® technology, as described below. Such mice are capable of producing human immunoglobulin molecules and antibodies and are deficient in the production of murine immunoglobulin molecules and antibodies. Technologies utilised for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

Through the use of such technology, fully human monoclonal antibodies to a variety of antigens have been produced. Essentially, XenoMouse® lines of mice are immunised with an antigen of interest (e.g. B7-H1), lymphatic cells (such as B-cells) are recovered from the hyper-immunised mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to B7-H1. Further, provided herein are characterisation of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the B7-H1 immunogen. The supernatants might also be screened for immunoreactivity against fragments of B7-H1 to further map the different antibodies for binding to domains of functional interest on B7-H1. The antibodies may also be screened other related human proteins and against the rat, the mouse, and non-human primate, such as Cynomolgus monkey, orthologues of B7-H1, the last to determine species cross-reactivity. B cells from wells containing antibodies of interest may be immortalised by various methods including fusion to make hybridomas either from individual or from pooled wells, or by infection with EBV or transfection by known immortalising genes and then plating in suitable medium. Alternatively, single plasma cells secreting antibodies with the desired specificities are then isolated using a B7-H1-specific hemolytic plaque assay (see for example Babcook et al., Proc. Natl. Acad. Sci. USA 93:7843-48 (1996)). Cells targeted for lysis are preferably sheep red blood cells (SRBCs) coated with the B7-H1 antigen.

In the presence of a B-cell culture containing plasma cells secreting the immunoglobulin of interest and complement, the formation of a plaque indicates specific B7-H1-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

As will be appreciated, antibodies as described herein can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalised cell lines available from the NCIMB, including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells (Hek293), and a number of other cell lines. Cell lines of particular preference are selected through determining which cell lines have high expression levels and produce antibodies with constitutive B7-H1 binding properties.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Antibody Sequences

Embodiments of the invention include the antibodies listed below in Table 1. This table reports the identification number of each antibody, along with the SEQ ID number of the variable domain of the corresponding heavy chain and light chain genes and polypeptides, respectively. Each antibody sequence has been given an identification number.

TABLE 1

| mAb ID No.: | Sequence | SEQ ID NO: |
| --- | --- | --- |
| 2.7A4 | Nucleotide sequence encoding the variable region of the heavy chain | 1 |
| | Amino acid sequence encoding the variable region of the heavy chain | 2 |
| | Nucleotide sequence encoding the variable region of the light chain | 6 |
| | Amino acid sequence encoding the variable region of the light chain | 7 |
| 2.9D10 | Nucleotide sequence encoding the variable region of the heavy chain | 11 |
| | Amino acid sequence encoding the variable region of the heavy chain | 12 |
| | Nucleotide sequence encoding the variable region of the light chain | 16 |
| | Amino acid sequence encoding the variable region of the light chain | 17 |
| 2.14H9 | Nucleotide sequence encoding the variable region of the heavy chain | 21 |
| | Amino acid sequence encoding the variable region of the heavy chain | 22 |
| | Nucleotide sequence encoding the variable region of the light chain | 26 |
| | Amino acid sequence encoding the variable region of the light chain | 27 |
| 2.20A8 | Nucleotide sequence encoding the variable region of the heavy chain | 31 |
| | Amino acid sequence encoding the variable region of the heavy chain | 32 |
| | Nucleotide sequence encoding the variable region of the light chain | 36 |
| | Amino acid sequence encoding the variable region of the light chain | 37 |
| 3.15G8 | Nucleotide sequence encoding the variable region of the heavy chain | 41 |
| | Amino acid sequence encoding the variable region of the heavy chain | 42 |
| | Nucleotide sequence encoding the variable region of the light chain | 46 |
| | Amino acid sequence encoding the variable region of the light chain | 47 |

TABLE 1-continued

| mAb ID No.: | Sequence | SEQ ID NO: |
| --- | --- | --- |
| 3.18G1 | Nucleotide sequence encoding the variable region of the heavy chain | 51 |
| | Amino acid sequence encoding the variable region of the heavy chain | 52 |
| | Nucleotide sequence encoding the variable region of the light chain | 56 |
| | Amino acid sequence encoding the variable region of the light chain | 57 |
| 2.7A4 OPT | Nucleotide sequence encoding the variable region of the heavy chain | 61 |
| | Amino acid sequence encoding the variable region of the heavy chain | 62 |
| | Nucleotide sequence encoding the variable region of the light chain | 66 |
| | Amino acid sequence encoding the variable region of the light chain | 67 |
| 2.14H9 OPT | Nucleotide sequence encoding the variable region of the heavy chain | 71 |
| | Amino acid sequence encoding the variable region of the heavy chain | 72 |
| | Nucleotide sequence encoding the variable region of the light chain | 76 |
| | Amino acid sequence encoding the variable region of the light chain | 77 |

Therapeutic Administration and Formulations

Embodiments of the invention include sterile pharmaceutical formulations of anti-B7-H1 antibodies that are useful as treatments for diseases. Such formulations would inhibit the binding of B7-H1 to one or more of its cognate ligands, thereby treating pathological conditions where, for example, serum or tissue B7-H1 is abnormally elevated. Antibodies of the invention preferably possess adequate affinity to potently inhibit B7-H1 activity, or inhibit B7-H1 binding to one or more of its cognate ligands, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilisation and reconstitution of the antibody. The antibody ordinarily will be stored in lyophilised form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumour site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilised). The composition can also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilisers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20*th* ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-β-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for protein stabilisation depending on the mechanism involved. For example, if the aggregation mechanism is discovered to be intermolecular S—S bond formation through disulfide interchange, stabilisation can be achieved by modifying sulfhydryl residues, lyophilising from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., Proc. Natl. Acad. Sci. USA, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages can be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.0001 mg/kg, 0.001 mg/kg, 0.01 mg/kg, 0.1 mg/kg, 1 mg/kg, 10 mg/kg to up to 100 mg/kg, 1000 mg/kg, 10000 mg/kg or more, of the patient's body weight depending on the factors mentioned above. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight depending on the factors mentioned above. Typically, the clinician will administer the therapeutic antibody until a dosage is reached that achieves the desired effect. The progress of this therapy is easily monitored by conventional assays or as described herein.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilisation and development of solid protein pharmaceuticals." *Int. J. Pharm.* 203(1-2):1-60 (2000), Charman W N "Lipids, lipophilic drugs, and oral drug delivery-some emerging concepts." *J Pharm Sci* 0.89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterised herein with respect to B7-H1, the design of other therapeutic modalities beyond antibody moieties is facilitated and disclosed to one skilled in the art. Such modalities include, without limitation, advanced antibody therapeutics, such as bispecific antibodies, immunotoxins, radiolabeled therapeutics, and single antibody V domains, antibody-like binding agent based on other than V region scaffolds, single domain antibodies, generation of peptide therapeutics, B7-H1 binding domains in novel scaffolds, gene therapies, particularly intrabodies, antisense therapeutics, and small molecules.

An antigen binding site may be provided by means of arrangement of CDRs on non-antibody protein scaffolds, such as fibronectin or cytochrome B etc. (Haan & Maggos (2004) BioCentury, 12(5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12(42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In connection with the generation of advanced antibody therapeutics, where complement fixation is a desirable attribute, it can be possible to sidestep the dependence on complement for cell killing through the use of bispecific antibodies, immunotoxins, or radiolabels, for example.

For example, bispecific antibodies can be generated that comprise (i) two antibodies one with a specificity to B7-H1 and another to a second molecule that are conjugated together, (ii) a single antibody that has one chain specific to B7-H1 and a second chain specific to a second molecule, or (iii) a single chain antibody that has specificity to B7-H1 and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made as desired. For example, the second specificity can be made to the heavy chain activation receptors, including, without limitation, CD16 or CD64 (see e.g., Deo et al. *Immunol. Today* 18:127 (1997)) or CD89 (see e.g., Valerius et al. *Blood* 90:4485-4492 (1997)).

Antibodies can also be modified to act as immunotoxins utilising techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilising techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each immunotoxin or radiolabeled molecule would be likely to kill cells expressing the desired multimeric enzyme subunit oligomerisation domain.

When an antibody is linked to an agent (e.g., radioisotope, pharmaceutical composition, or a toxin) it is contemplated that the agent possesses a pharmaceutical property selected from the group of antimitotic, alkylating, antimetabolite, antiangiogenic, apoptotic, alkaloid, COX-2, and antibiotic agents and combinations thereof. The agent can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof. Examples of toxins further include gelonin, Pseudomonas exotoxin (PE), PE40, PE38, diphtheria toxin, ricin, abrin, alpha toxin, saporin, ribonuclease (RNase), DNase I, Staphylococcal enterotoxin-A, pokeweed antiviral protein, gelonin, Pseudomonas endotoxin, members of the enediyne family of molecules, such as calicheamicin and esperamicin, as well as derivatives, combinations and modifications thereof. Chemical toxins can also be taken from the group consisting of duocarmycin (see, e.g., U.S. Pat. Nos. 5,703,080, 4,923, 990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

Examples of radioisotopes include gamma-emitters, positron-emitters, and x-ray emitters that can be used for localisation and/or therapy, and beta-emitters and alpha-emitters that can be used for therapy. The radioisotopes described previously as useful for diagnostics, prognostics and staging are also useful for therapeutics.

Non-limiting examples of anti-cancer or anti-leukemia agents include anthracyclines such as doxorubicin (adriamycin), daunorubicin (daunomycin), idarubicin, detorubicin, carminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. Preferably, the anti-cancer or anti-leukemia is doxorubicin, morpholinodoxorubicin, or morpholinodaunorubicin.

The antibodies of the invention also encompass antibodies that have half-lives (e.g., serum half-lives) in a mammal, preferably a human, of greater than that of an unmodified antibody. In one embodiment, said antibody half life is greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatisation that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

As will be appreciated by one of skill in the art, in the above embodiments, while affinity values can be important, other factors can be as important or more so, depending upon the particular function of the antibody. For example, for an immunotoxin (toxin associated with an antibody), the act of binding of the antibody to the target can be useful; however, in some embodiments, it is the internalisation of the toxin into the cell that is the desired end result. As such, antibodies with a high percent internalisation can be desirable in these situations. Thus, in one embodiment, antibodies with a high efficiency in internalisation are contemplated. A high efficiency of internalisation can be measured as a percent internalised antibody, and can be from a low value to 100%. For example, in varying embodiments, 0.1-5, 5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of B7-H1 expression in mammalian tissues or cells in order to screen for a disease or disorder associated with changes in expression of B7-H1. The kit comprises an antibody that binds B7-H1 and means for indicating the reaction of the antibody with the antigen, if present.

In some embodiments, an article of manufacture is provided comprising a container, comprising a composition containing an antibody that specifically binds B7-H1, and a package insert or label indicating that the composition can be used to treat disease mediated by B7-H1 expression. Preferably a mammal and, more preferably, a human, receives the antibody that specifically binds B7-H1.

Combinations

The anti-tumour treatment defined herein may be applied as a sole therapy or may involve, in addition to the compounds of the invention, conventional surgery, bone marrow and peripheral stem cell transplantations or radiotherapy or chemotherapy. Such chemotherapy may include one or more of the following categories of anti tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin); (ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or inhibitors of cathepsin activity, inhibitors of serine proteases for example matriptase, hepsin, urokinase and inhibitors of integrin αvβ6 function.

(iv) cytotoxic agents such as fludarabine, 2-chlorodeoxyadenosine, chlorambucil or doxorubicin and combination thereoff such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CNOP: cyclophosphamide+mitoxantrone+vincristine+prednisone, m-BACOD: methotrexate+bleomycin+doxorubicin+cyclophosphamide+vincristine+dexamethasone+leucovorin., MACOP-B: methotrexate+doxorubicin+cyclophosphamide+vincristine+prednisone fixed dose+bleomycin+leucovorin, or ProMACE CytaBOM: prednisone+doxorubicin+cyclophosphamide+etoposide+cytarabine+bleomycin+vincristine+methotrexate+leucovorin.

(v) inhibitors of growth factor function: for example such inhibitors include growth factor antibodies and growth factor receptor antibodies (for example the anti-erbB2 antibody trastuzumab 5 [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin™)] and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651, anti-vascular endothelial growth factor receptor antibodies such anti-KDR antibodies and anti-fit1 antibodies,) and compounds that work by other mechanisms (for example linomide, inhibitors of integrin αvβ3 function and angiostatin)] or colony stimulating factor 1 (CSF1) or CSF1 receptor; Additional details on AZD2171 may be found in Wedge et al (2005) Cancer Research. 65(10): 4389-400. Additional details on AZD6474 may be found in Ryan & Wedge (2005) British Journal of Cancer. 92 Suppl 1:S6-13. Both publications are herein incorporated by reference in their entireties.

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as ISIS 2503, an anti-ras antisense or G3139 (Genasense), an anti bcl2 antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(x) immunotherapy approaches, including for example treatment with Alemtuzumab (campath-1H™), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumour cell lines and approaches using anti idiotypic antibodies, adoptive T-cell transfer using T-cells that have been non-specifically activated or targeted to a specific antigen of interest ex vivo;

(xi) Vaccination approaches, including for example treatment with a vaccine directed against a specific viral infection such as HIV or HBV, or treatment with a vaccine directed against a specific tumour antigen;

(xii) inhibitors of protein degradation such as proteasome inhibitor such as Velcade (bortezomid); and (xiii) biotherapeutic therapeutic approaches for example those which use peptides or proteins (such as antibodies or soluble external receptor domain constructions) which either sequester receptor ligands, block ligand binding to receptor or decrease receptor signalling (e.g. due to enhanced receptor degradation or lowered expression levels).

In one embodiment the anti-tumour treatment defined herein may involve, in addition to the compounds of the invention, treatment with other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin).

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1: Expression of Recombinant Human B7-H1

The human B7-H1 cDNA (Dong, H. et al., 1999, Nat. Med. 5:1365-1369) was amplified from Image clone 7262208 (ATCC) using polymerase chain reaction (PCR) and then cloned into the Nhe 1 and EcoR1 sites of pcr3.1Bid vector. This construct was lipofected into CHO cells (American Type Tissue Collection, catalog #CCL-61) and the expression on the cell surface was confirmed by fluorescent activated cell sorting (FACS) analysis.

The extracellular domain of human B7-H1 (amino acid residues 1-239) fused to the Fc region of human IgG1 was purchased from R&D Systems Inc., catalog #156-B7-100.

Example 2: Immunisation and Titering

Immunisation Monoclonal antibodies against human B7-H1 were developed by sequentially immunizing XenoMouse® mice (XenoMouse strains: XMG2 (IgG2 kappa/lambda) and XMG4 (IgG4 kappa/lambda) Amgen, Inc. Vancouver, British Columbia, Canada) with either 5-10 ug of the B7-H1/Fc chimera protein or 1-2×10(6) CHO cells expressing recombinant human B7-H1 as described in Example 1.

Immunisations were conducted according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. The immunisation programs are summarised in Table 2.

Selection of Animals for Harvest by Titer Titres of antibodies in sera from the immunised mice were determined in an ELISA assay.

Plates (Corning Costar, cat #3368) were coated with the human B7-H1/Fc protein (R&D Systems Inc., catalog #156-B7-100). B7-H1—specific antibodies were detected with mouse anti-human IgG antibody and goat anti-mouse IgG Fc antibody conjugated to horseradish peroxidase. Typically, five animals with the highest titres within each immunization cohort were selected for lymphocyte isolation and generation of hybridomas.

TABLE 2

Summary of Immunisation Programs

| Group | Immunogen | Strain | No of mice | Immunisation routes |
|---|---|---|---|---|
| 1 | Recombinant human B7-H1/Fc protein | IgG2 | 10 | IP/SC, twice/wk, for 5 weeks |
| 2 | Recombinant human B7-H1/Fc protein | IgG4 | 10 | IP/SC, twice/wk, for 5 weeks |
| 3 | CHO cells expressing human B7-H1 | IgG2 | 10 | IP/SC, twice/wk, for 5 weeks |
| 4 | CHO cells expressing human B7-H1 | IgG4 | 10 | IP/SC, twice/wk, for 5 weeks |

"IP" refers to "intraperitoneal" and "SC" refers to "subcutaneous"

Example 3: Recovery of Lymphocytes, B-Cell Isolations, Fusions and Generation of Hybridomas Immunised mice were sacrificed by cervical dislocation, and the draining lymph nodes harvested and pooled from each cohort. The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 μl of CD90+ magnetic beads per 100 million cells, the cells were labeled by incubating the cells with the magnetic beads at 4° C. for 15 minutes. The magnetically labeled cell suspension containing up to 108 positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3x63Ag8.653 cells purchased from ATCC, cat. #CRL 1580 (Kearney et al, J. Immunol. 123, 1979, 1548-1550) at a ratio of 1:1. The cell mixture was gently pelleted by centrifugation at 800×g. After complete removal of the supernatant, the cells were treated with 2-4 mL of Pronase solution (CalBiochem, cat. #53702; 0.5 mg/ml in PBS) for no more than 2 minutes. Then β-5 ml of FBS was added to stop the enzyme activity and the suspension was adjusted to 40 ml total volume using electro cell fusion solution, (ECFS, 0.3M Sucrose, Sigma, Cat #S7903, 0.1 mM Magnesium Acetate, Sigma, Cat #M2545, 0.1 mM Calcium Acetate, Sigma, Cat #C4705). The supernatant was removed after centrifugation and the cells were resuspended in 40 ml ECFS. This wash step was repeated and the cells again were resuspended in ECFS to a concentration of $2\times10^6$ cells/ml.

Electro-cell fusion was performed using a fusion generator (model ECM2001, Genetronic, Inc., San Diego, CA). The fusion chamber size used was 2.0 ml, using the following instrument settings:

Alignment condition: voltage: 50 V, time: 50 sec.

Membrane breaking at: voltage: 3000 V, time: 30 psec

Post-fusion holding time: 3 sec

After ECF, the cell suspensions were carefully removed from the fusion chamber under sterile conditions and transferred into a sterile tube containing the same volume of Hybridoma Culture Medium (DMEM, JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in a small volume of Hybridoma Selection Medium (Hybridoma Culture Medium supplemented with 0.5×HA (Sigma, cat. #A9666)), and the volume adjusted appropriately with more Hybridoma Selection Medium, based on a final plating of $5\times10^6$ B cells total per 96-well plate and 200 μl per well. The cells were mixed gently and pipetted into 96-well plates and allowed to grow. On day 7 or 10, one-half the medium was removed, and the cells re-fed with Hybridoma Selection Medium.

Hybridomas were grown as routine in the selective medium. Exhaustive supernatants collected from the hybridomas were tested in various assays as described in Examples 4-5. Just to note, antibodies that begin with a 3 digit, e.g., 3.15G8, are IgG4 and antibodies that begin with a 2, e.g., 2.9D10, are IgG2.

Example 4: Binding to Cell Bound Human and Cynomolgus Monkey B7-H1

Supernatants collected from hybridoma cells were tested to assess the ability of the secreted antibodies to bind to 293T cells transiently expressing either full length human or cynomolgus monkey B7-H1. A mock-transfected 293T cell line was used as a negative control. Cells diluted in PBS containing 2% FBS were seeded at a density of 2500-3000 expressing and 15000-17500 mock transfected cells in 40 μl/well in 384 well plates (Corning Costar, catalog #3712). Immediately after plating, 10 μl/well of hybridoma supernatants were added and plates incubated for 1.5 hr at room temperature. Next, 10 μl/well of Cy5-conjugated goat anti-human IgG Fc (700 ng/ml, Jackson Immunoresearch, catalog #109-175-098) were added and plates incubated for 3 h at room temperature prior to reading the fluoresence signal on the FMAT 8200 instrument (Applied Biosystems). The results for 6 hybridoma supernatants are shown in Table 3.

TABLE 3

| Binding of hybridoma supernatants to cell-bound human or cynomologus B7-H1 | | | | | |
|---|---|---|---|---|---|
| | Human B7-H1 binding | | | Cynomolgus monkey B7-H1 binding | |
| Antibody ID | Count | FL1 | FL1xcount | Count | FL1 | FL1xcount |
| 2.9D10 | 22 | 7176 | 157872 | 54 | 5526.9 | 298454 |
| 2.14H9 | 31 | 10289 | 318949 | 56 | 6777.9 | 379561 |
| 3.15G8 | 22 | 8811 | 193850 | 64 | 8647.1 | 553414 |
| 2.20A8 | 34 | 10283 | 349622 | 65 | 7930.5 | 515484 |
| 2.7A4 | 37 | 6975.9 | 258108 | 59 | 8697.7 | 513164 |
| 3.18G1 | 21 | 10862 | 228106 | 66 | 10336.3 | 682195 |

Example 5: Inhibition of B7-H1/Pd-1 Receptor-Ligand Binding

To determine the relative potency of the antibody containing supernatants, their ability to inhibit the binding of human PD-1/Fc protein to human B7-H1 expressed on surface of CHO cells was evaluated. 25000 cells/well were plated in 50 μl of media into wells of a 384-well tissue culture plate (Corning Costar, catalog #3712). Next day, 50 μl/well of diluted (1:5) hybridoma supernatant was added and plates were incubated at 4 C for 1 hour on a shaker. Biotinylated human PD-1/Fc protein (R&D Systems, catalog #1086-PD) was added to a final concentration of 1.25 ug/ml and plates were incubated at 4 C for 1 hour on a shaker. Cells were washed and fixed in 100 ul of PBS containing 3.7% formaldehyde and 3% bovine serum albumin for 20 min at room temperature. Cells were washed and incubated in 100 ul of PBS containing 0.6% $H_2O_2$ and 3% bovine serum albumin for 10 min at room temperature. Cells were washed and incubated in 50 μl of horseradish peroxidase-conjugated streptavidin diluted at 1:4000 for 30 min at 4° C. Cells were washed before signal detection. Data are represented as the percentage of (ODmax−ODmin), where ODmax is the average value obtained with the cells incubated with irrelevant hybridoma supernatants in the presence of biotin-conjugated human PD-1/Fc protein and ODmin is the average value obtained with the cells incubated with irrelevant hybridoma supernatants in the absence of biotin-conjugated human PD-1/Fc protein. 0% of maximum response indicates 100% inhibition of B7-H1/PD-1 binding by a hybridoma supernatant (Table 4).

TABLE 4

Inhibition of human PD1 binding to human B7-H1
expressing cells by hybridoma supernatants

| Antibody ID | PD1-Fc binding to CHO-huB7-H1 cells (% of max) |
|---|---|
| 2.9D10 | −5 |
| 2.14H9 | 5 |
| 3.15G8 | 4 |
| 2.20A8 | 0 |
| 2.7A4 | 0 |
| 3.18G1 | 5 |

Example 6: Binding of Purified Anti-B7-H1 Antibodies to Human B7-H1, Human B7-Dc, Mouse B7-H1

The ability of the purified antibodies to bind to human B7-H1, B7-DC, mouse B7H1 and cynomolgus monkey B7-H1 was determined by FACS analysis. Briefly, 293T cells were either mock-transfected or transiently transfected with either human B7-H1 or human B7-DC using Lipofectamine 2000 (Invitrogen, catalog #11668). Mouse J558 cells expressing mouse B7-H1 were obtained from ATCC (catalog #TIB-6). Cells were resuspended in PBS containing 2% FBS (FACS buffer) and seeded at 50000 cells/well into V-bottomed plates. Anti-B7-H1 and isotype control antibodies diluted in FACS buffer were added at a final concentration of 5 μg/ml and plates were incubated for 1 h at 4° C. After washing with FACS buffer, goat anti-human Fc Cy5 (5 pg/ml, Jackson Immunoresearch, catalog #109-175-098) and 7-AAD (5 pg/ml) were added and plates were incubated for 15 min at 4° C. before being washed again with FACS buffer and being read on a FACSCalibur instrument. Table 5 shows ability of purified antibodies (5 pg/ml) to bind to 293T cells transfected with human B7-H1. None of the selected antibodies bound to 293T cells transfected with human B7-DC or to J558 cells that express mouse B7-H1. Mouse anti-human B7-DC (PD-L2) antibody (R&D systems cat #MAB1224, detected with goat anti-mouse Fc Cy5, Jackson Immunoresearch) was used as a positive control for B7-DC expression. PE-conjugated rat anti-mouse B7-H1 antibody (eBioscience, clone M1H5, detected with goat anti-rat Fc Cy5, Jackson Immunoresearch) was used as a positive control for mouse B7-H1 expression.

TABLE 5

Binding of purified anti-B7-H1 antibodies to cell-bound human
B7-H1, mouse B7-H1 or human B7-DC

| Ab ID | Human(h)B7-H1/293T (geo mean) | Human(h)B7-DC/293T (geo mean) | 293T (geo mean) | J558 (geo mean |
|---|---|---|---|---|
| 2.9D10 | 463.3 | 8.7 | 8.9 | 3.2 |
| 2.14H9 | 792.1 | 11.4 | 9.9 | 3.0 |
| 3.15G8 | 1183.3 | 10.1 | 9.4 | 3.2 |
| 2.20A8 | 462.8 | 9.5 | 8.4 | 3.3 |
| 2.7A4 | 753.8 | 10.5 | 9.4 | 3.2 |
| 3.18G1 | 1539.6 | 9.7 | 10.5 | 3.2 |
| IgG2 | 7.6 | 9.5 | 9.1 | 3.1 |
| IgG4 | 10.7 | 8.8 | 9.3 | 3.2 |

Example 7: Binding of Purified Human Anti-B7-H1 Antibodies to Stimulated Human and Cynomolgus Monkey T Cells 96-well high binding plates were incubated with 100 ul/well of anti-CD3 antibody diluted at 1 ug/ml in PBS (OKT3 clone, eBioscience, catalog #160037) at 4 C overnight. Human T cells were isolated from frozen leukopack using T cell enrichment kit (StemCell Technologies, catalog #19051). Anti-CD3 mAb coated plates were washed with PBS and purified T cells were added in 200 ul of ICM media at 360000 cells/well and cultured for 72 hours. T cells were then harvested, washed in FACS buffer and mixed with diluted purified anti-B7-H1 antibodies or irrelevant human IgG2 or IgG4 antibodies at final concentration of 1 ug/ml in 96-well V-bottom assay plate (50 ul/well). After 2 hours incubation at 4 C, T cells were washed twice in FACS buffer and then stained with Cy5-conjugated goat anti-human IgG Fc antibody (5 ug/ml, Jackson Immunoresearch, catalog #109-175-098) and 7-AAD (10 ug/ml). Cells were incubated for 30 min at 4° C. before being washed again with FACS buffer and being read on a FACSCalibur instrument. Live lymphocyte population was selected for analysis based on forward and side scatter as well as negative staining for 7-AAD.

For activation of cynomolgus monkey T cells 96-well high binding plates were incubated with 100 ul/well of goat anti-mouse IgG Fc antibody diluted at 1 ug/ml in PBS at 4 C overnight. Plates were washed with PBS and incubated with anti-CD3 antibody diluted at 1 ug/ml in ICM media (clone SP-34, BD catalog #556610) at 37 C for 2 hours. Cynomolgus monkey PBMC were isolated from peripheral blood (Bioreclamation, catalog #CYNWBCPT). Anti-CD3 mAb coated plates were washed with PBS and isolated PBMC were added in 200 ul of ICM media at ~200000 cells/well and cultured for 72 hours. Cells were then harvested, washed in FACS buffer and mixed with diluted purified anti-B7-H1 antibodies or irrelevant human IgG2 or IgG4 antibodies at a final concentration of 1 ug/ml in 96-well V-bottom assay plate (50 ul/well). After 2 hours incubation at 4 C, cells were washed twice in FACS buffer and then stained with Cy5-conjugated goat anti-human IgG Fc antibody (5 ug/ml, Jackson Immunoresearch, catalog #109-175-098), FITC-conjugated anti-CD3 antibody (diluted 1:25, Biospecialty) and 7-AAD (10 ug/ml). Cells were incubated for 1 hour at 4° C. before being washed again with FACS buffer and being read on a FACSCalibur instrument. Monkey T lymphocyte population was selected for analysis based on forward and side scatter as well as positive staining for CD3 marker and negative staining for 7-AAD. Table 6 shows the ability of purified anti-B7-H1 antibodies (1 pg/ml) to bind to activated human T cells as well as to activated cynomolgus monkey T cells.

TABLE 6

Binding of purified anti-B7-H1 antibodies to stimulated
human or cynomologus T-cells

| Ab ID | Human T cells (geo mean) | Cyno T cells (geo mean) |
|---|---|---|
| 2.9D10 | 49.0 | 106.8 |
| 2.14H9 | 53.0 | 106.3 |
| 3.15G8 | 48.0 | 92.8 |
| 2.20A8 | 41.0 | 80.7 |
| 2.7A4 | 49.0 | 103.9 |
| 3.18G1 | 45.0 | 94.6 |
| IgG2 | 10.0 | nd |
| IgG4 | 10.0 | 17.6 |

Example 8: Inhibition of B7-H1/Pd-1 Receptor-Ligand Binding

The ability of purified human anti-B7-H1 antibodies to inhibit the binding of human PD-1/Fc protein to human B7-H1 expressed on surface of ES-2 cells (ATCC, catalog #CRL-1978) was evaluated. Briefly, 50000 cells/well were plated in 50 ul of PBS into wells of a 384-well tissue culture plate (Corning Costar, catalog #3712). Next, 50 μl/well of a diluted monoclonal antibody was added at final concentration of 2.5, 0.5, 0.1, 0.02, 0.004, 0.008, 0.00016 nM and plates were incubated at 4 C for 1 hour. Cells were washed twice and 100 μl/well of biotinylated human PD-1/Fc protein (10 ug/ml, R&D Systems, catalog #1086-PD) was added and plates were incubated at 4 C for 1 hour. Cells were washed once and 100 μl/well of Cy5-conjugated streptavidin was added and plates were incubated at 4 C for 15 min before being washed again with PBS containing 2% FCS and being read on a FACSCalibur instrument. Some wells were incubated with irrelevant human IgG2 and IgG4 monoclonal antibodies with or without biotin-conjugated human PD-1/Fc to set minimal (0%) and maximal (100%) level of B7-H1/PD-1 binding inhibition. The percentage of the inhibition in relation to the antibody concentration was analyzed using curve fit tool (GraphPad Prism software) to calculate IC50 value for each antibody, which are shown in table 7.

TABLE 7

| Inhibition of human PD1 binding to human B7-H1 expressing ES-2 cell by purified anti-B7-H1 antibodies | |
| --- | --- |
| Ab ID | IC50, nM |
| 2.9D10 | 0.109 |
| 2.14H9 | 0.083 |
| 3.15G8 | 0.148 |
| 2.20A8 | 0.198 |
| 2.7A4 | 0.077 |
| 3.18G1 | 0.140 |

Example 9: Determination of the Effects of Anti-B7-H1 Antibodies on Proliferation of CD4 T Cells It has been demonstrated that B7-H1 protein co-presented with anti-CD3 antibody on beads inhibits CD3-mediated T cell activation (Freeman et al., J. Exp. Med., 2000, 192 (7): 1027-1034; Bennet et al., The Journal of Immunology, 2003, 170: 711-718). The ability of purified human monoclonal anti-B7-H1 antibodies to interfere with B7-H1-mediated suppression of T cell activation was determined as follows.

Briefly, 5×10(8) beads/ml of washed tosyl-activated Dynabeads M-450 (Invitrogen, Cat #140.13) were coated with 50 μg/ml of mouse anti-human CD3 antibody (BD Bioscience, Cat #555329) in 0.1 M sodium phosphate buffer (pH 7.4-8.0) at 37° C. for 24 hours with shaking. 4×10(8) of CD3-coated beads/ml were further coupled with recombinant human IgG1Fc (R&D Systems, cat #110-HG-100) at 160 μg/ml or with the recombinant human B7-H1/Fc protein (R&D Systems, Cat #156-B7-100) at 80 μg/ml combined with the human IgG1Fc protein at 80 μg/ml (total concentration 160 μg/ml) and incubated at 37° C. for 24 hours with shaking. The beads were then incubated in PBS containing 0.05% bovine serum albumin at room temperature for 1 hour, washed four times in 0.1% BSA and 2 mM EDTA in PBS (pH7.4) and finally resuspended in RPMI1640 media containing 10% FBS at 5×10(7) beads/ml.

Peripheral blood monocytes were isolated from a leukapheresis pack using Ficoll-Paque Plus (GE Healthcare 17-1440-03) density gradient centrifugation, resuspended in serum-free RPMI 1640 (Gibco 22400-089), and CD4+ T-cells were isolated from PBMC using Dynal CD4 Negative Isolation Kit (Invitrogen, cat #113-37D) per manufacturer's instructions. 10 ul of coated beads were mixed 10 ul of diluted anti-B7-H1 or control IgG2/4 antibody in a sample tube and incubated at RT for 3-4 hours on a shaker. Purified CD4+ T cells were plated at 10(5) cells/80 ul/well in 96-well plate (Corning, cat #3603) and bead-antibody mix was added at 20 ul/well to a total volume of 100 ul/well. T cell activation in the absence of B7-H1 inhibitory effect was determined using beads coated with anti-CD3 antibody and the human IgG1Fc protein. Cells were cultured for 5 days and supernatants were harvested and analyzed for IFN-γ release by using BD Human IFN-γ ELISA Kit II (BD Cat. No. 550612) per manufacturer's instructions. Cell proliferation was measured on day 5 by the addition of 10 μl/well of AlamarBlue (Invitrogen DAL 1025). Cells were incubated for 5 hours, and the fluorescence was quantitated on a SpectraMax Gemini EM spectrophotometer with an excitation wavelength of 545 nm and an emission wavelength of 600 nm. Data are represented as the percentage of ODmax, where ODmax is the average value obtained with T cells activated with anti-CD3/IgG1Fc beads. See FIG. 1.

Example 10: Determination of the Effects of Anti-B7-H1 Antibodies on Activation of CD4 T Cells in Dendritic Cell-T-Cell Mixed Lymphocyte Assay Enhancement of T cell activation by antibodies directed against B7-H1 was determined in a dendritic cell-T-cell mixed lymphocyte (DCMLR) assay. Dendritic cells were generated from monocytic precursors as described previously (Curr Protoc Immunol. 2001 May; Chapter 7: Unit 7.32). Peripheral blood monocytes were isolated from a leukapheresis pack using Ficoll-Paque Plus (GE Healthcare 17-1440-03) density gradient centrifugation, resuspended in serum-free RPMI 1640 (Gibco 22400-089), and allowed to adhere to T150 cell culture flasks (Corning 430825). After 1 hour at 37° C., the nonadherent cells were removed and the cells were cultured in RPMI supplemented with 5% human serum (Invitrogen 34005100). Cytokines were added at a final concentration of 2 ng/ml GM-CSF (BD Biosciences 550068) and 10 ng/ml IL-4 (BD Biosciences 554605). Fresh media with cytokines was added every 2-3 days. At day 6 of culture, cells were matured with 20 ng/ml of TNF-α (BD Biosciences 554618) and allowed to incubate for 24 hours. Mature dendritic cells were harvested, phenotyped, and frozen for later use.

Figure 2:
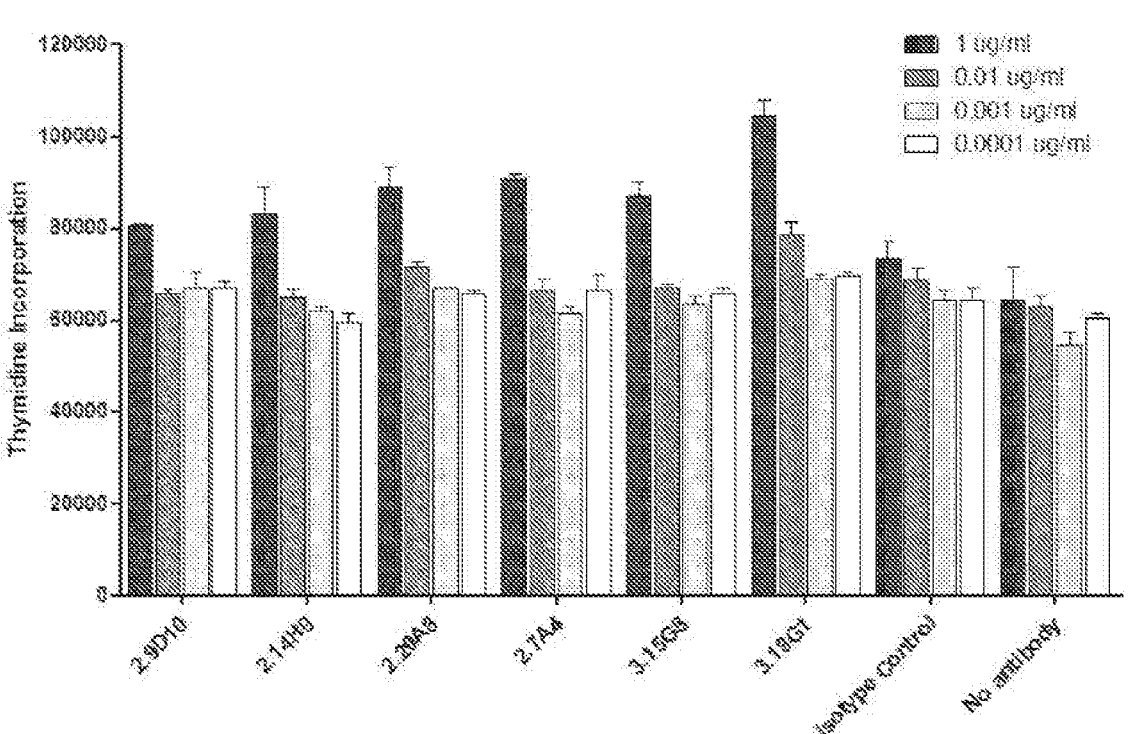
FIG. 2 is a bar graph showing enhancement of T-cell proliferation by anti-B7-H1 antibodies of the invention in DCMLR assay.
Figure 3:
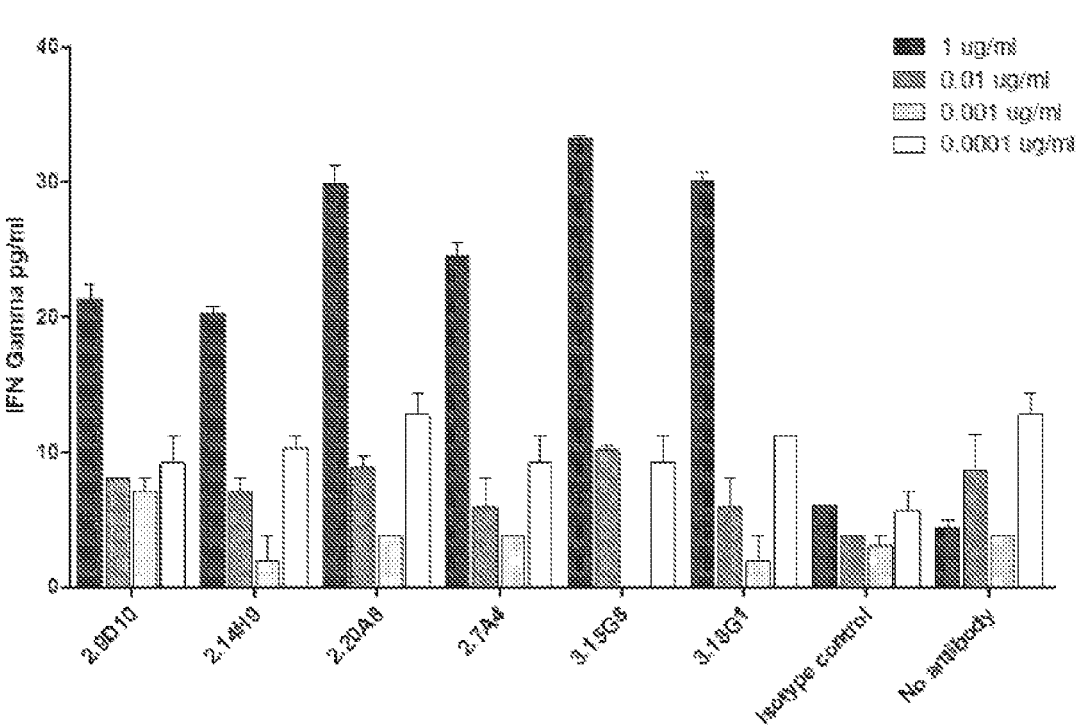
FIG. 3 is a bar graph showing IFN-γ release by anti-B7-H1 antibodies of the invention in DCMLR assay.

CD4+ T-cells were isolated from PBMC using a magnetic isolation kit (Dynal 113.17) per manufacturer's instructions and cultured in a primary MLR as described previously (J Immunol. 2003 Apr. 1; 170(7):3637-44). 1.5E5 allogeneic CD4+ responding T-cells were cultured in 96 well-flat bottom microtiter plates (Costar 3595) with dendritic cells at a T-cell:dendritic cell ratio of 1:2.5. Dendritic cell preparations were treated with 100 pg/ml of mitomycin C (Sigma M4287) prior to addition to coculture to prevent any proliferation from contaminating lymphocytes. Antibodies were added at various concentrations in a final volume of 200 μl of RPMI+10% human serum. Thymidine incorporation was measured on Day 5 by a 16-h pulse with [3H]thymidine (1 μci/well, Perkin-Elmer NET027001MC). Supernatants were harvested prior to radioactive labeling and analyzed for IFN-γ release by Luminex assay (BioRad 171-B11921) per manufacturer's instructions. Enhancement of T-cell proliferation by anti-B7-H1 antibodies from repeat experiments is shown in FIG. 2. Corresponding IFN-γ release is shown in FIG. 3.

Example 11: Structural Analysis of B7-H1 Antibodies

The heavy chain variable domain sequences and the light chain variable domain sequence s of the antibodies were sequenced to determine their DNA sequences. The complete sequence information for the anti-B7-H1 antibodies is provided in the sequence listing with nucleotide and amino acid sequences for each gamma and kappa or lambda chain combination. The variable heavy sequences were analyzed to determine the VH family and the J-region sequence. The sequences were then translated to determine the primary amino acid sequence and compared to the germline VH and J-region sequences to assess somatic hypermutations.

Tables 8 and 9 are tables comparing the antibody heavy chain regions to their cognate germline heavy chain region and the antibody light chain regions to their cognate germline light chain region. The amino acid numbering is by numerical numbering.

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult, or increase the immunogenicity risk of the antibody. In general, mutations in CDR regions are likely to contribute to improved affinity and function, while mutations in framework regions may increase the risk of immunogenicity. This risk can be reduced by reverting framework mutations to germline, while ensuring that activity of the antibody is not adversely impacted. Some structural liabilities may be generated by the diversification processes, or they may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites.

In order to reduce the risk of immunogenicity, and improve pharmaceutical properties of lead antibodies, it may be desirable to reduce the number of mutations from germline and/or remove structural liabilities.

Thus, in one embodiment, where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. Tables $10^{-14}$ below illustrate the positions of such variations back to germline for mAb 2.9D10, 2.7A4 and 2.14H9. Each row represents a unique combination of germline and non-germline residues at the position indicated by bold type. The position of the amino acid is represented by numerical numbering.

In another embodiment, the invention includes replacing any structural liabilities in the sequence that might affect the heterogeneity of the antibodies of the invention. Such liabilities include glycosylation sites, un-paired cysteines, surface exposed methinones, etc. To reduce the risk of such heterogeneity it is proposed that changes are made to remove one or more of such structural liabilities.

In one embodiment, it may be desirable to remove one or more consensus N-linked glycosylation sites from the antibody germline or antibody sequence. One skilled in the art would be readily able to identify such a glycosylation site. Typically an N-linked glycosylation consensus site sequence has the sequence of Asn-any AA-Ser or Thr where the middle amino acid cannot be a proline (Pro). In another example, unpaired cysteines can be replaced alone or in conjunction with other structural changes. An unpaired cysteine can be mutated to an appropriate amino acid that has comparable side chain properties such as a serine.

As referred to herein, a sequence that is optimized is a sequence which has been mutated at one or more positions back to its germline sequence or can be modified to remove one or more other liabilities such as structural liabilities. An optimized sequence can also include a sequence that has been mutated at one or more positions back to its germline sequence and which has also been further modified to remove one or more structural liabilities.

TABLE 8

| | | | | | FR1 SEQ ID NOS 87, 87, 87, 87, 94, 95, 95 and 96 | CDR1 SEQ ID NOS 97, 98, 97, 97, 97, 100, 102, and 103 | FR2 SEQ ID NOS 104, 104, 104, 104, 105, 105, 105 and 105 | CDR2 SEQ ID NOS 24, 24, 24, 14, 4, 34, and | FR3 SEQ ID NOS 108, 108, 108, 106, 108, 107 108, 107 111, 54 | CDR3 SEQ ID NOS 113, 25, 45, 15, 5, 35, and | FR4 SEQ ID NOS 119, 119, 120, 119, 119, 119 119 |
|---|---|---|---|---|---|---|---|---|---|---|---|
| | | | | Full length SEQ ID NO: | | | | | | 114, 115, 116, 117, 118 55 | 119, 119, 120, 119, 119, and |
| Heavy chain | V | D | J | | | | | | | | |
| | Germ-line | | | 81 | EVQLVES GGGLVQP GGSLRLS CAAS | GFTFSSYWM S | WVRQAPGK GLEWVA | NIKQDGS EKYYVDS VKG | RFTISRDNAKN SLYLQMNSLRA EDTAVYYCAR | ###WFGEL #FDY | WGQGTLVT VSS |
| 2.14H9 | VH3-7 | D3-10 | JH4B | 22 | ------- ------- ------- ---- | -----R--- - | -------- ------ | ------- ------- --- | ----------- ----------- ---------- | EGG----- A--- | -------- --- |

*Table 8 header note as printed: FR1 SEQ ID NOS 87, 87, 87, 87, 94, 95, 95 and 96; CDR1 SEQ ID NOS 97, 98, 97, 97, 100, 102, 101 and 103; FR2 SEQ ID NOS 104, 104, 104, 104, 105, 105, 105 and 105; CDR2 SEQ ID NOS 24, 24, 24, 14, 4, 34, 107 and 54; FR3 SEQ ID NOS 108, 108, 109, 108, 110, 111, 112; CDR3 SEQ ID NOS 113, 114, 115, 116, 117, 118 and 55; FR4 SEQ ID NOS 119, 119, 119, 120, 120, 119, 119, 119 and 119.*

TABLE 8-continued

| | | | | Full length SEQ ID NO: | FR1 SEQ ID NOS 87, 87, 87, 87, 87, 94, 95, 95 and 96 | CDR1 SEQ ID NOS 97, 98, 97, 97, 97, 99, 100, 101, 102, 101 and 103 | FR2 SEQ ID NOS 104, 104, 104, 104, 104, 105, 105, 105 and 105 | CDR2 SEQ ID NOS 24, 24, 24, 44, 24, 14, 4, 34, 107 and 54 | FR3 SEQ ID NOS 108, 108, 108, 109, 108, 108, 110, 111, 111 and 112 | CDR3 SEQ ID NOS 113, 25, 114, 45, 115, 15, 116, 5, 117, 35, 118 and 55 | FR4 SEQ ID NOS 119, 119, 119, 119, 120, 120, 119, 119, 119, 119 and 119 |
|---|---|---|---|---|---|---|---|---|---|---|---|
| Heavy chain | V | D | J | | | | | | | | |
| | | Germ-line | | 82 | EVQLVES GGGLVQP GGSLRLS CAAS | GFTFSSYWM S | WVRQAPGK GLEWVA | NIKQDGS EKYYVDS VKG | RFTISRDNAKN SLYLQMNSLRA EDTAVYYCAR | #QL###YF DY | WGQGTLVT VSS |
| 3.15G8 | VH3-7 | D6-6 | JH4B | 42 | ------- ------- ------- ---- | --------- - | -------- ------- | ------G ------- --- | ----------- --F--------- ---------- | V--YSD-- -- | -------- --- |
| | | Germ-line | | 83 | EVQLVES GGGLVQP GGSLRLS CAAS | GFTFSSYWM S | WVRQAPGK GLEWVA | NIKQDGS EKYYVDS VKG | RFTISRDNAKN SLYLQMNSLRA EDTAVYYCAR | DWNYYYYG MDV | WGQGTTVT VSS |
| 2.9D10 | VH3-7 | D1-1 | JH6B | 12 | ------- ------- ------- ---- | --------- - | -------- ------- | ------G -Q----- --- | ----------- ----------- ---------- | ----G--D --- | -------- --- |
| | | Germ-line | | 84 | EVQLVES GGGLVQP GGSLRLS CAAS | GFTFSSYSM N | WVRQAPGK GLEWVS | SISSSSS YIYYADS VKG | RFTISRDNAKN SLYLQMNSLRA EDTAVYYCAR | ###TAMV# FDY | WGQGTLVT VSS |
| 2.7A4 | VH3-21 | D5-5 | JH4B | 2 | ------- ------- ------- ---- | -----T--- - | -------- ------- | -----GD ------- --- | ----------- --F------K- ---------- | DLV-S--A --- | -------- --- |
| | | Germ-line | | 85 | EVQLVES GGGLVQP GGSLRLS CAAS | GFTFSSYAM S | WVRQAPGK GLEWVS | AISGSGG STYYADS VKG | RFTISRDNAKN SLYLQMNSLRA EDTAVYYCAK | ###YDSSG ##DY | WGQGTLVT VSS |
| 2.20A8 | VH3-23 | D3-22 | JH4B | 32 | ------- ------- ------- ---- | -----N--- - | -------- ------- | --R---- ------- --- | ----------- ----------- ---------- | DLH----- YL-- | -------- ------ |
| | | Germ-line | | 86 | EVQLVES GGGLVQP GGSLRLS CAAS | GFTFSSYAM S | WVRQAPGK GLEWVS | AISGSGG STYYADS VKG | RFTISRDNAKN SLYLQMNSLRA EDTAVYYCAK | ###GYSY# ##DY | WGQGTLVT VSS |
| 3.18G1 | VH3-23 | D5-5 | JH4B | 52 | ------- ------- ------- ---- | ----N---- - | -------- ------- | T------ F-FS--- --- | ----------- --F-------V --S---S--- | VLV-FNN GCW-- | -------- ---- |

TABLE 9

Table 9

| Light Chain | V | J | Full length SEQ ID NO: | FR1 SEQ ID NOS 121, 121, 121, 121, 122, 122, 122, 122, 123, 124, 125 and 125 | CDR1 SEQ ID NOS 126, 28, 126, 18, 48, 48, 48, 38, 127, 48, 58 and 58 | FR2 SEQ ID NOS 128, 128, 128, 128, 129, 130, 131, 130, 130, 132, 132, 133 and 133 | CDR2 SEQ ID NOS 134, 29, 134, 19, 49, 135, 39, 9, 9, 59 and 59 | FR3 SEQ. ID NOS 136, 136, 136, 136, 137, 138, 137, 137, 139, 139, 140 and 140 | CDR3 SEQ ID NOS 141, 30, 142, 20, 143, 50, 144, 40, 145, 10, 146 and 60 | FR4 SEQ. ID NOS 147, 148, 149, 149, 147, 147, 150, 150, 151, 152, 151 and 153 |
|---|---|---|---|---|---|---|---|---|---|---|
| | | Germline | 88 | EIVLTQSPGTLS LSPGERATLSC | RASQSVSSSYLA | WYQQKPGQAPRL LIY | GASSRAT | GIPDRFSGSGS GTDFTLTISRL EPEDFAVYYC | QQYGS##WT | FGQGTKVE IK |
| 2.14H9 | A27 | JK1 | 27 | ------------ ---------- | ----R------- | ------------ --- | D------ | ----------- ----------- ---------- | -----LP-- | -----E-- -- |
| | | Germline | 89 | EIVLTQSPGTLS LSPGERATLSC | RASQSVSSSYLA | WYQQKPGQAPRL LIY | GASSRAT | GIPDRFSGSGS GTDFTLTISRL EPEDFAVYYC | QQYGSS#FT | FGPGTKVD IK |
| 2.9D10 | A27 | JK3 | 17 | ------------ ---------- | --------N--- | -F---------- --F | -T----- | ----------- ----------- ---------- | ------I-- | -------- -- |
| | | Germline | 90 | DIQMTQSPSSVS ASVGDRVTITC | RASQGISSWLA | WYQQKPGKAPKL LIY | AASSLQS | GVPSRFSGSGS GTDFTLTISSL QPEDFATYYC | QQANSFPPT | FGQGTKVE IK |
| 3.15G8 | L5 | JK1 | 47 | ------------ ---------- | ------------ | ------S----- ----- | ---G--- | ----------- ----------- ----L----- | --SH-L--- | -------- -- |
| | | Germline | 91 | DIQMTQSPSSVS ASVGDRVTITC | RASQGISSWLA | WYQQKPGKAPKL LIY | AASSLQS | GVPSRFSGSGS GTDFTLTISSL QPEDFATYYC | QQANSF##T | FGGGTKVE IK |
| 2.20A8 | L5 | JK4 | 37 | ------------ ---------- | ------R---- | ------------ --- | -I-R--- | ----------- ----------- ---------- | ------PL- | -------- -- |
| | | Germline | 92 | SYELTQPPSVSV SPGQTARITC | SGDALPKKYAY | WYQQKSGQAPVL VIY | EDSKRPS | GIPERFSGSSS GTMATLTISGA QVEDEADYYC | YSTDSSGNH RV | FGGGTKLT VL |
| 2.7A4 | V2-7 | JL3 | 7 | ------------ ----A----- | ------Q--VF | ------------ --- | ------- | ----------- ----------- ---------- | ----R---- -- | -----R-- -- |
| | | Germline | 93 | SYVLTQPPSVSV APGQTARITC | GGNNIGSKSVH | WYQQKPGQAPVL VVY | DDSDRPS | GIPERFSGSNS GNTATLTISRV EAGDEADYYC | QVWDSSSDH VV | FGGGTKLT VL |
| 3.18G1 | V2-14 | JL2 | 57 | ------------ ---------- | ------------ | ------------ --- | ------- | ----------- ----------- ---------- | ------N-- -- | -------- -- |

| TABLE 10 | | | | | | TABLE 10-continued | | | | |
|---|---|---|---|---|---|---|---|---|---|---|
| Exemplary Mutations of 2.7A4 Heavy Chain (SEQ ID NO: 2) to Germline at the Indicated Residue Number | | | | | | Exemplary Mutations of 2.7A4 Heavy Chain (SEQ ID NO: 2) to Germline at the Indicated Residue Number | | | | |
| 31 | 55 | 56 | 80 | 87 | | 31 | 55 | 56 | 80 | 87 |
| S | S | S | F | K | | S | G | S | Y | K |
| T | S | S | F | K | | T | G | S | Y | K |
| S | G | S | F | K | | S | S | D | Y | K |
| T | G | S | F | K | | T | S | D | Y | K |
| S | S | D | F | K | | S | G | D | Y | K |
| T | S | D | F | K | | T | G | D | Y | K |
| S | G | D | F | K | | S | S | S | F | R |
| T | G | D | F | K | | T | S | S | F | R |
| S | S | S | Y | K | | S | G | S | F | R |
| T | S | S | Y | K | | T | G | S | F | R |

TABLE 10-continued

| 31 | 55 | 56 | 80 | 87 |
|---|---|---|---|---|
| S | S | D | F | R |
| T | S | D | F | R |
| S | G | D | F | R |
| T | G | D | F | R |
| S | S | S | Y | R |
| T | S | S | Y | R |
| S | G | S | Y | R |
| T | G | S | Y | R |
| S | S | D | Y | R |
| T | S | D | Y | R |
| S | G | D | Y | R |
| T | G | D | Y | R |

Exemplary Mutations of 2.7A4 Heavy Chain (SEQ ID NO: 2) to Germline at the Indicated Residue Number In some embodiments of the invention, the targeted binding agent or antibody comprises a sequence comprising SEQ ID NO.: 2. In certain embodiments, SEQ ID NO.: 2 comprises any one of the combinations of germline and non-germline residues indicated by each row of Table 10. In some embodiments, SEQ ID NO: 2 comprises any one, any two, any three, any four, any five, or all five of the germline residues as indicated in Table 10. In certain embodiments, SEQ ID NO.: 2 comprises any one of the unique combinations of germline and non-germline residues indicated by each row of Table 10. In one specific example, the non germline sequence is mutated back to germline at position 80 where F is changed to a Y and at position 87 where K is changed to an R. A specific example of such a sequence is 2.7A4VHOPT as shown in Table 15.

TABLE 11

Exemplary Mutations of 2.7A4 Light Chain (SEQ ID NO: 7) to Germline at the Indicated Residue Number

| 17 | 29 | 32 | 33 | 104 |
|---|---|---|---|---|
| T | K | A | Y | K |
| A | K | A | Y | K |
| T | Q | A | Y | K |
| A | Q | A | Y | K |
| T | K | V | Y | K |
| A | K | V | Y | K |
| T | Q | V | Y | K |
| A | Q | V | Y | K |
| T | K | A | F | K |
| A | K | A | F | K |
| T | Q | A | F | K |
| A | Q | A | F | K |
| T | K | V | F | K |
| A | K | V | F | K |
| T | Q | V | F | K |
| A | Q | V | F | K |
| T | K | A | Y | R |
| A | K | A | Y | R |
| T | Q | A | Y | R |
| A | Q | A | Y | R |
| T | K | V | Y | R |
| A | K | V | Y | R |
| T | Q | V | Y | R |
| A | Q | V | Y | R |
| T | K | A | F | R |
| A | K | A | F | R |
| T | Q | A | F | R |
| A | Q | A | F | R |
| T | K | V | F | R |
| A | K | V | F | R |
| T | Q | V | F | R |
| A | Q | V | F | R |
| T | K | A | Y | R |

TABLE 11-continued

Exemplary Mutations of 2.7A4 Light Chain (SEQ ID NO: 7) to Germline at the Indicated Residue Number

| 17 | 29 | 32 | 33 | 104 |
|---|---|---|---|---|
| A | K | A | Y | R |
| T | Q | A | Y | R |
| A | Q | A | Y | R |
| T | K | V | Y | R |
| A | K | V | Y | R |
| T | Q | V | Y | R |
| A | Q | V | Y | R |
| T | K | A | F | R |
| A | K | A | F | R |
| T | Q | A | F | R |
| A | Q | A | F | R |
| T | K | V | F | R |
| A | K | V | F | R |
| T | Q | V | F | R |
| A | Q | V | F | R |

In some embodiments of the invention, the targeted binding agent or antibody comprises a sequence comprising SEQ ID NO.: 7. In certain embodiments, SEQ ID NO.: 7 comprises any one of the combinations of germline and non-germline residues indicated by each row of Table 11. In some embodiments, SEQ ID NO: 7 comprises any one, any two, any three, any four, any five, or all five of the germline residues as indicated in Table 11. In certain embodiments, SEQ ID NO.: 7 comprises any one of the unique combinations of germline and non-germline residues indicated by each row of Table 11. Specific examples of 2.7A4 variable light domain which has been mutated to particular germline sequences include 2.7A4 VLOPT (optimized where the non-germline sequence has been mutated from an A to a T at position 17 and a R to a K at position 104) as shown in Table 15.

TABLE 12

Exemplary Mutations of 2.9D10 Heavy Chain (SEQ ID NO: 12) to Germline at the Indicated Residue Number

| 56 | 58 |
|---|---|
| G | K |
| S | K |
| G | Q |
| S | Q |

In some embodiments of the invention, the targeted binding agent or antibody comprises a sequence comprising SEQ ID NO.: 12. In certain embodiments, SEQ ID NO.: 12 comprises any one of the combinations of germline and non-germline residues indicated by each row of Table 12. In some embodiments, SEQ ID NO: 12 comprises any one, any two, or all two of the germline residues as indicated in Table 12. In certain embodiments, SEQ ID NO.: 12 comprises any one of the unique combinations of germline and non-germline residues indicated by each row of Table 12.

TABLE 13

Exemplary Mutations of 2.9D10 Light Chain (SEQ ID NO: 17) to Germline at the Indicated Residue Number

| 32 | 37 | 50 | 52 |
|---|---|---|---|
| S | Y | Y | A |
| N | Y | Y | A |

TABLE 13-continued

| Exemplary Mutations of 2.9D10 Light Chain (SEQ ID NO: 17) to Germline at the Indicated Residue Number | | | |
|---|---|---|---|
| 32 | 37 | 50 | 52 |
| S | F | Y | A |
| N | F | Y | A |
| S | Y | F | A |
| N | Y | F | A |
| S | F | F | A |
| N | F | F | A |
| S | Y | Y | T |
| N | Y | Y | T |
| S | F | Y | T |
| N | F | Y | T |
| S | Y | F | T |
| N | Y | F | T |
| S | F | F | T |
| N | F | F | T |
| S | Y | Y | A |
| N | Y | Y | A |
| S | F | Y | A |
| N | F | Y | A |
| S | Y | F | A |
| N | Y | F | A |
| S | F | F | A |
| N | F | F | A |
| S | Y | Y | T |
| N | Y | Y | T |
| S | F | Y | T |
| N | F | Y | T |
| S | Y | F | T |
| N | Y | F | T |
| S | F | F | T |
| N | F | F | T |

In some embodiments of the invention, the targeted binding agent or antibody comprises a sequence comprising SEQ ID NO.: 17. In certain embodiments, SEQ ID NO.: 17 comprises any one of the combinations of germline and non-germline residues indicated by each row of Table 13. In some embodiments, SEQ ID NO: 17 comprises any one, any

TABLE 14

| Exemplary Mutations of 2.14H9 Light Chain (SEQ ID NO: 27) to Germline at the Indicated Residue Number | | |
|---|---|---|
| 28 | 51 | 104 |
| R | G | K |
| S | G | K |
| R | D | K |
| S | D | K |
| R | G | K |
| S | G | K |
| R | D | K |
| S | D | K |
| R | G | E |
| S | G | E |
| R | D | E |
| S | D | E |
| R | G | E |
| S | G | E |
| R | D | E |
| S | D | E |

In some embodiments of the invention, the targeted binding agent or antibody comprises a sequence comprising SEQ ID NO.: 27. In certain embodiments, SEQ ID NO.: 27 comprises any one of the combinations of germline and non-germline residues indicated by each row of Table 14. In some embodiments, SEQ ID NO: 27 comprises any one, any two, any three, or all three of the germline residues as indicated in Table 14. In certain embodiments, SEQ ID NO.: 27 comprises any one of the unique combinations of germline and non-germline residues indicated by each row of Table 14. Specific examples of 2.7A4 variable light domain which has been mutated to a particular germline sequence including 2.14H9OPT (optimized where the non-germline sequence has been mutated from an E to a K at position 104) as shown in Table 15.

The heavy chain of 2.14H9 can be changed at amino acid 31 of SEQ ID NO:22 from a R to a S.

TABLE 15

Table 15

| | Full length SEQ ID NO: | FR1 SEQ ID NOS 153, 123 and 121 | CDR1 SEQ ID NOS 63, 68 and 78 | FR2 SEQ ID NOS 105, 132 and 128 | CDR2 SEQ ID NOS 64, 69 and 79 | FR3 SEQ ID NOS 108, 139 and 136 | CDR3 SEQ ID NOS 65, 70 and 80 | FR4 SEQ ID NOS 119, 151 and 147 |
|---|---|---|---|---|---|---|---|---|
| 2.7A4OPT Heavy Chain | 62 | EVQLVESGGGL VKPGGSLRLSC AASGFTFS | TYSMN | WVRQAPGKGL EWVS | SISSSGDYW YADSVKG | RFTISRDNAKNSL YLQVINSLRAEDT AVYYCAR | DLVTSMVA FDY | WGQGTLV TVSS |
| 2.7A4OPT Light Chain | 67 | SYELTQPPSVSV SPGQTARITC | SGDALPQK YVF | WYQQKSGQAP VLVIY | EDSKRFS | GIPERFSGSSSGTM ATLTISGAQVEDE ADYYC | YSTDRSGNH RV | FGGGTKLT VL |
| 2.14H9OPT Light Chain | 77 | EIVLTQSPGTLS LSPGERATLSC | RASQRVSS SYLA | WYQQKPGQAP RLLIY | DASSRAT | GIPDRESGSGSGTD FTLTBRLEPEDFA VYYC | QQYGSLPW T | FGQGTKVE IK | two, any three, any four, or all four of the germline residues as indicated in Table 7. In certain embodiments, SEQ ID NO.: 17 comprises any one of the unique combinations of germline and non-germline residues indicated by each row of Table 13. SEQ ID NO: 17 can be altered or further altered by making nongermlining changes to SEQ ID NO: 17. In one example, SEQ ID NO:17 can be altered such that from a F to a Y at position 37 and from a F to a Y at position 50.

Examples of Specific Germlining

The amino acid sequences of the VH and VL domains of the non-germlined (NG) anti-B7-H1 antibodies 2.7A4, 2.14H9 and 2.9D10 were aligned to the known human germline sequences in the VBASE database (Tomlinson, 1997; http://vbase.mrc-cpe.cam.ac.uk/), and the closest germline was identified by sequence similarity. The closest germline match for the anti-B7-H1 antibodies is described in Tables 16 and 17. Without considering the Vernier residues (Foote & Winter, J Mol Biol. Mar20:224(2):487-99, 1992), which were left unchanged, the positions to be changed are described in Table 18.

TABLE 16

Anti-B7-H1 heavy chain closest V and J germline matches

| | V | J |
|---|---|---|
| 2.7A4 Heavy Chain | VH3_(3-21) | JH4b |
| 2.9D10 Heavy Chain | VH3_(3-07) | JH6b |
| 2.14H9 Heavy Chain | VH3_(3-07) | JH4b |

TABLE 17

Anti-B7-H1 light chain closest V and J germline matches

| | V | J |
|---|---|---|
| 2.7A4 Light Chain | VL3_(3p) | JL2 |
| 2.9D10 Light Chain | VK3_(A27) | JK3 |
| 2.14H9 Light Chain | VK3_(A27) | JK1 |

Considering antibody 2.7A4 there are 2 changes in the frameworks of the VH domain and 2 changes in the frameworks of the VL domain. These residues, located at Kabat number 79 and 83 (or residues 80 and 87 if by numerical numbering) for the VH domain and Kabat number 18 and 103 (or residues 17 and 104 if by numerical numbering) for the VL domain, were reverted to the human germline. See Table 18. For antibody 2.14H9 there are no changes in the frameworks of the VH domain and 1 change in the frameworks of the VL domain. This residue, located at Kabat number 103 in the VL domain (or 104 if residue calculated using numerical numbering), was reverted to human germline. See Table 18. In antibody 2.9D10 there are no changes in the frameworks of the VH domain and 2 changes in VL domain, located at Kabat number at Kabat numbers 36 and 49 (or numerical numbering residues 37 and 50). However, those 2 residues are located at Vernier position and have not been mutated to not alter the CDR loop structures.

TABLE 18

Example of residues mutated during germlining for anti-B7-H1 V domains. Residues are numbering according to Kabat nomenclature

| Germlined V domain | Mutations |
|---|---|
| 2.7A4VHOPT | F79Y + K83R |
| 2.7A4VLOPT | A18T + R103K |
| 2.14H9VLOPT | E103K |

Germlining of these amino acid residues was carried out using standard site directed mutagenesis techniques with the appropriate mutagenic primers. The germlined sequences have the prefix "OPT" after the antibody name, for example, 2.7A4VHOPT, 2.7VLOPT and 2.14H9VLOPT. Germlined IgG were then re-evaluated in the human B7-H1/hPD1 ligand inhibition assay to confirm there had not been a reduction in antibody in vitro activity.

Figure 4:
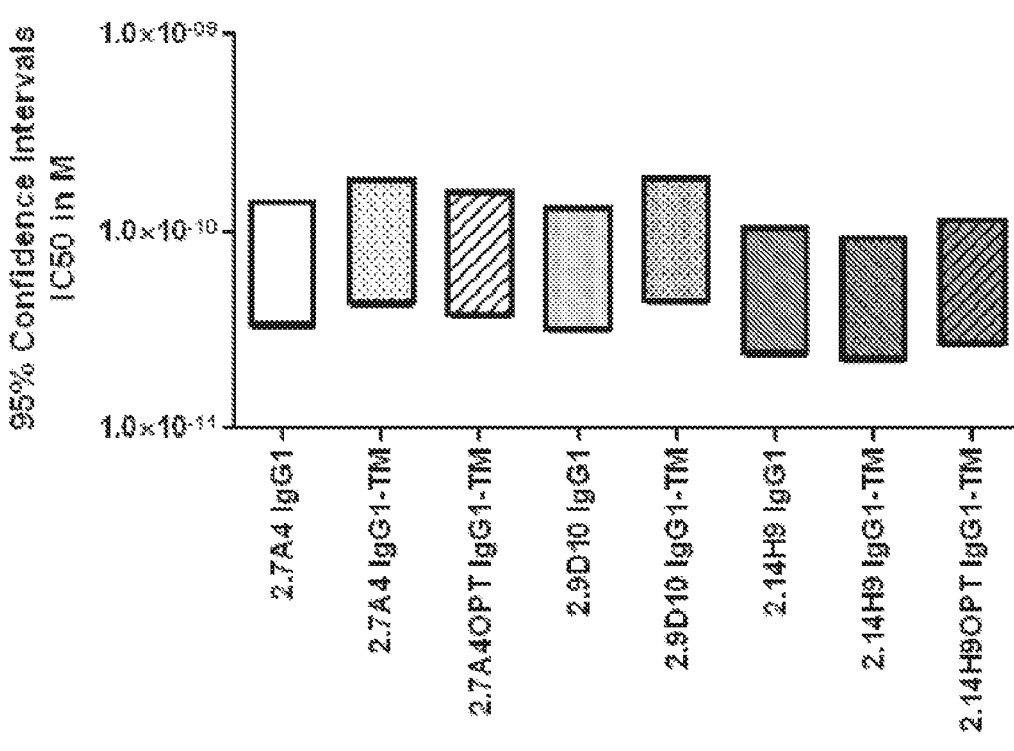
FIG. 4 is a graph showing 95% confidence interval for anti-B7-H1 IC50 by anti-B7-H1 antibodies of the invention in the human PD1/human B7-H1 ligand inhibition assay to evaluate the impact of IgG class switching and germlining on antibody activity.

Example activities for germlined versus non-germlined anti-B7-H1 antibodies are provided in FIG. 4.

Example of Gene Synthesis and Reformatting as IgG1 and IgG1-TM

Clones were converted from scFv to IgG format by sub-cloning the VH and VL domains into vectors expressing whole antibody heavy and light chains respectively. The VH domains were cloned into the vector pEU15.1 to express IgG1 or the vector pEU15.1-TM to express IgG1-TM antibodies. Both vectors contain the human heavy chain constant domains and regulatory elements to express whole IgG heavy chain in mammalian cells. The vector pEU15.1-TM is a modified pEU15.1 human IgG1 vector. It was engineered to introduce the three mutations; L234F and L235E in the hinge and P331S in the CH2 domain of the IgG molecule to eliminate its ability to trigger antibody-dependent cell-mediated cytotoxicity and complement-dependent cytotoxicity (Oganesyan V. et al. (2008), Acta Cryst., D64: 700-704). Vector engineering was performed using standard site directed mutagenesis techniques with the appropriate mutagenic primers.

The VL domains were cloned into pEU4.4 and pEU3.4 vectors for the expression of the human lambda and kappa light chain constant domains respectively, with regulatory elements to express whole IgG light chain in mammalian cells. Vectors for the expression of heavy chains and light chains were originally described in Vaughan et al. (Nature Biotechnology 14(3):309-314, 1996). These vectors have been engineered simply by introducing an OriP element.

To obtain IgGs, the heavy and light chain IgG expression vectors were transfected into EBNA-HEK293 mammalian cells (Invitrogen R620-07). IgGs were expressed and secreted into the medium. Harvests were pooled and spun down prior to purification. The IgG was purified using Protein A chromatography using an AKTA Express purification system (GE Healthcare) previously sanitised to avoid any endotoxin contamination of the sample. Culture supernatants are loaded onto 1 mL HiTrap™ MabSelectSure™ columns (GE Healthcare, 11-0034-93) and washed with 50 mM Tris-HCl pH 8.0, 250 mM NaCl. Bound IgG was eluted from the column using 0.1 M Sodium Citrate (pH 3.0) and neutralised by the addition of 1M Tris-HCl (pH 9.0). The eluted material was buffer exchanged into PBS using Nap10 columns (Amersham, 17-0854-02) and filtered before determining protein concentration and endotoxin levels. IgG concentration was determined spectrophotometrically using an extinction coefficient based on the amino acid sequence of the IgG (Vaughan et al. supra). Endotoxin level was determined using the Endosafe PTS Portable Test System (Charles River Laboratories) fitted with 1-0.1 EU/mL and 10-0.1 EU/mL LAL cartridges (Charles River Laboratories, PT520). The purified IgG were analysed for degradation by SDS-PAGE.

Anti-B7-H1 antibodies in the IgG1-TM format were evaluated and compared to the same antibodies but in the IgG1 format in the human B7-H1/hPD1 ligand inhibition assay to confirm there had not been a reduction in antibody in vitro activity due to IgG isotype switching (FIG. 4).

Example 12: Human B7H1/FC Binding Human PD1/FC—HTRF® Assay

The assay described is a homogenous TR-FRET assay using HTRF® assay technology requiring no wash steps. To a Costar 3676 microtitre plate 5 µl/well of biotinylated PD1/Fc at 1 nM diluted into PBS was added. This was followed with the addition of 5 µl/well streptavidin XL$^{ent}$ (CisBio) at 4 nM diluted into assay buffer (PBS+0.1% BSA+0.8M KF). 5 µl/well of a titration of sample material diluted in PBS was added to relevant wells. For the definition of total binding, 5 µl of PBS or relevant sample buffer was added per well. To define non-specific binding, an excess (600 nM) of unlabelled B7H1/Fc or PD1/Fc was used. The final process was the addition of 5 µl/well of cryptate labelled B7H1/Fc (cryptate label—CisBio, B7H1/Fc—RnD Systems) diluted 1:100 into assay buffer. The assay plate was left for 3 hours at room temperature before being read on a HTRF© compatible plate reader.

Example of IC50 determinations in the human PD1/human B7-H1 ligand inhibition assay for anti-B7-H1 antibodies are provided in Table 19. All anti-human B7-H1 antibodies are in the IgG1-TM format.

TABLE 19

| Example of IC50 determination (n = 2) in the human PD1/human B7-H1 ligand inhibition assay for anti-B7-H1 IgG | | |
|---|---|---|
| Antibody | Arithmetic mean | Standard Deviation |
| 2.9D10 | 1.1E−10 | 3.6E−11 |
| 2.7A4OPT | 1.6E−10 | 1.4E−10 |
| 2.14H9OPT | 1.1E−10 | 7.5E−11 |

Example 13: Human B7H1/FC Binding Human B7-1/FC—HTRF® Assay

The assay described was a homogenous TR-FRET assay using HTRF® assay technology requiring no wash steps. To a Costar 3676 microtitre plate 5 µl/well of biotinylated B7-1/Fc at 8 nM diluted into PBS was added. This was followed with the addition of 5 µl/well streptavidin XL$^{ent}$ (CisBio) at 20 nM diluted into assay buffer (PBS+0.1% BSA+0.8M KF). 5 µl/well of a titration of sample material diluted in PBS was added to relevant wells. For the definition of total binding, 5 µl of PBS or relevant sample buffer per well was added. To define non-specific binding, an excess (200 nM) of unlabelled B7H1/Fc or B7-1/Fc was used. The final process was the addition of 5 µl/well of cryptate labelled B7H1/Fc (cryptate label—CisBio, B7H1/Fc—RnD Systems) diluted 1:100 into assay buffer. The assay plate was left overnight at 4° C. before being allowed to recover to room temperature and read on a HTRF© compatible plate reader.

Example of IC50 determinations in the human B7-1/human B7-H1 ligand inhibition assay for anti-B7-H1 antibodies are provided in Table 20. All anti-human B7-H1 antibodies are in the IgG1-TM format.

TABLE 20

| Example of IC50 determination (n = 2) in the human B7-1/human B7-H1 ligand inhibition assay for anti-B7-H1 IgG | | |
|---|---|---|
| Antibody | Arithmetic mean | Standard Deviation |
| 2.9D10 | 5.41E−11 | 1.61E−11 |
| 2.7A4OPT | 5.31E−11 | 4.03E−13 |
| 2.14H9OPT | 4.93E−11 | 1.50E−11 |

Example 14: Cross Reactivity of Anti-B7-H1 Antibodies with Other Immune Co-Modulatory Proteins ELISAs were performed to determine the cross-reactivity of the anti-B7-H1 IgG1-TM antibodies for other immune co-modulatory molecules. The ELISAs consisted of coating MaxiSorp plates (NUNC) at 4° C. overnight with 250 ng per well of the extracellular domain (ECD) of human B7-H1

(R&D Systems, 156-B7), human PD-L2 (R&D Systems, 1224-PL), human B7-H2 (R&D Systems, 165-B7), human B7-H3 (R&D Systems, 1027-B3), human CD28 (R&D Systems, 342-CD), human CTLA-4 (R&D Systems, 325-CT) and human PD1 (R&D Systems, 1086-PD) followed by blocking the plates with PBS containing 3% dried milk powder at room temperature for 1 h. Murine cross reactivity was also investigated by coating the ECD of murine B7-H1 (R&D Systems, 1019-B7). Biotinylated anti-B7-H1 IgG1-TM diluted at 100 nM in PBS containing 3% dried milk powder, were incubated at room temperature for 2 h to allow binding. Bound biotinylated IgGs were detected with europium N1-labelled streptavidin (Perkin Elmer, 1244-360) at 0.2 ug/mL. Control experiment demonstrating antigen coating to the NUNC plate was performed using the commercial antibodies mouse IgG2a anti-human B7-H1 (R&D Systems, MAB156), mouse IgG2b anti-human PD-L2 (R&D Systems, MAB1224), mouse IgG2b anti-human B7-H2 (R&D Systems, MAB165), mouse IgG1 anti-human B7-H3 (R&D Systems, MAB1027), mouse IgG1 anti-human CD28 (R&D Systems, MAB342), mouse IgG2a anti-human CTLA-4 (Abcam, ab33320), mouse IgG2b anti-human PD1 (R&D Systems, MAB1086) and rat IgG2a anti-mouse B7-H1 (R&D Systems, MAB1019). Primary antibodies were incubated at 5 ug/mL in PBS containing 3% dried milk powder for 2 h at room temperature. Detection was carried out by incubating the secondary antibody anti-mouse IgG Peroxidase conjugate (Sigma, A2554) or anti-rat IgG Peroxidase conjugate (Sigma, A5795) diluted 1:5000 in PBS containing 3% dried milk powder for 1 h at room temperature and subsequent addition of TMB (Sigma, T0440). All eight antigens could be detected on the Maxisorp NUNC plate. Non-specific binding was determined using wells coated with the IgG1 isotype control at 5 ug/mL. Cross reactivities were calculated at a percent of the specific binding to the antigen relative to human B7-H1.

Figure 5:
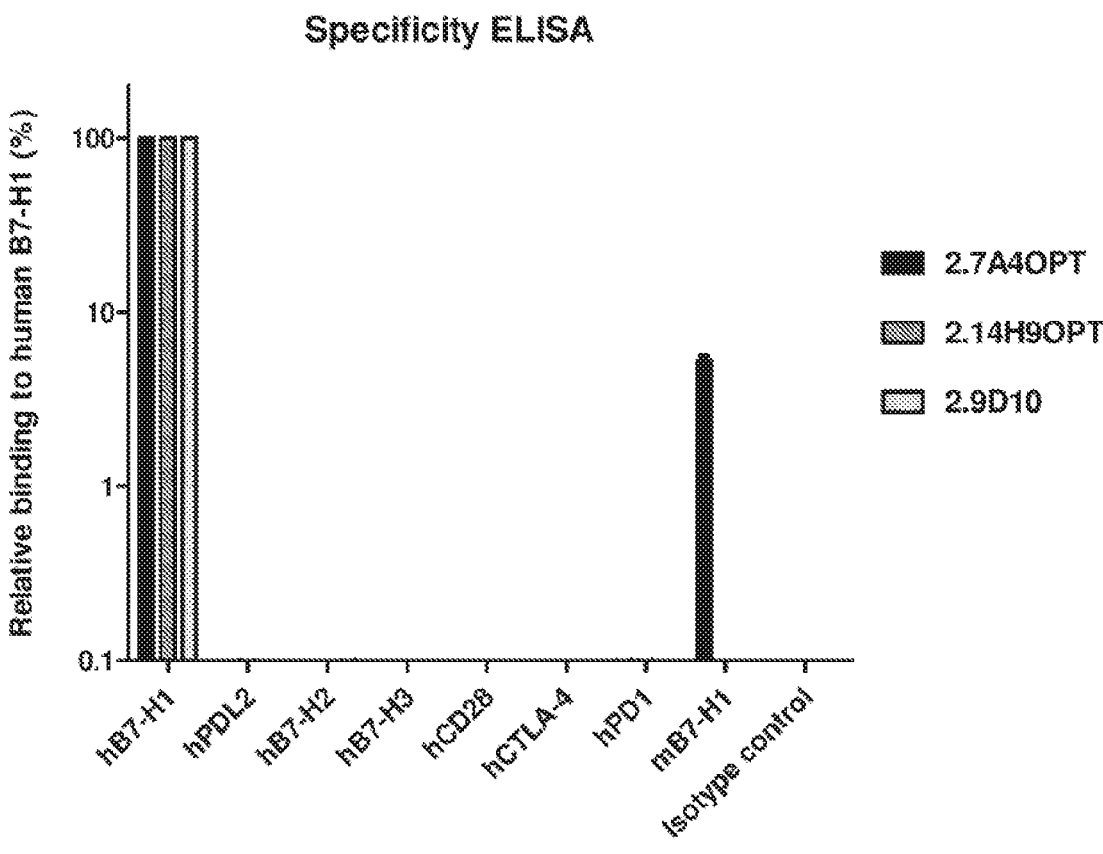
FIG. 5 is a line graph showing the results from an ELISA assay that was performed to evaluate anti-B7-H1 antibodies of the invention cross-reactivity to co-modulatory antigens.

The cross-reactivity of the 3 anti-B7-H1 IgG1-TM antibodies 2.7A4OPT, 2.9D10 and 2.14H9OPT to the panel of eight immune co-modulatory antigens were determined in triplicate. At 100 nM of antibody concentration, all three anti-B7-H1 antibodies show no cross reactivity for any of the seven human immune co-modulatory molecules we tested (FIG. 5). The IgG1-TM anti-B7-H1 antibody 2.7A4OPT displays a measurable cross reactivity for murine B7-H1 with a signal level of 5.3% on average compared to 100% binding to the human B7-H1. The other two anti-B7-H1 antibodies tested, 2.9D10 and 2.14H9OPT, do not show any cross reactivity for murine B7-H1 (FIG. 5).

Example 15: Affinity of Anti-B7-H1 Antibodies for Human and Cynomologus B7-H1

The binding affinity and kinetic parameters of anti-B7-H1 antibodies in the IgG1-TM format to monomeric human and cynomologus B7-H1 were determined by surface plasmon resonance using a BIAcore T100 instrument (BIAcore, Uppsala, Sweden). In brief, experiments were performed at 25° C. using HBS-EP buffer (10 mM HEPES, 150 mM NaCl, 3 mM EDTA, 0.05% v/v surfactant P20) as running buffer. IgGs were affinity captured on the surface of a CM5 sensor chip (BIAcore) via protein G, which was amine coupled onto the CM5 surface to achieve the density of ~500 Response Units (RU), according to the manufacturer's instructions (BIAapplications Handbook, BIAcore). Recombinant monomeric human or cynomologus B7-H1 FlagHisio extracellular domains (ECDs) were used as analytes. Dilutions of B7-H1 ECD (200-3.12 nM) in the running buffer were injected at a constant flow rate of 100 µl/min for 60 seconds. All measurements were baseline corrected by subtracting the sensorgram obtained with the control (activated-deactivated) flow cell, as well as double referenced with blank (zero analyte concentration) injections. Data were analyzed using the T-100 BIAevaluation software package and fitted to a simple 1:1 Langmuir binding model with local $R_{max}$ and bulk refractive index set to 0. Data were calculated from at least two independent experiments. Mass transport effects were limited by keeping the level of affinity-captured IgGs below 250 RU. Sensorgrams obtained with all tested antibodies could be readily fitted onto the monoexponential 1:1 binding model giving excellent fits with Chi$^2$ values consistently ≤0.3.

Affinity of anti-B7-H1 antibodies 2.7A4OPT and 2.14H9OPT for monomeric human B7-H1 is 1 nM and 175 pM respectively (Table 21).

TABLE 21

Affinity and kinetic parameters analysis of anti-B7-H1 antibodies for binding to human B7-H1

| mAb/HUMAN B7H1 | $K_d$ (nM) | $k_{on}$ (M$^{-1}$ s$^{-1}$) | $k_{off}$ (s$^{-1}$) |
|---|---|---|---|
| Reference Antibody #1 | 6.3 | $1.36 \times 10^6$ | 0.0086 |
| 2.7A4OPT | 1 | $1.24 \times 10^6$ | 0.0012 |
| 2.14H9OPT | 0.175 | $2 \times 10^6$ | 0.00035 |

Affinity of anti-B7-H1 antibodies 2.7A4OPT and 2.14H9OPT for monomeric cynomologus B7-H1 is 835 pM and 367 pM respectively (Table 22). Those two antibodies are strongly cross reactive for cynomologus B7-H1 as affinities are very close to the ones for human B7-H1.

TABLE 22

Affinity and kinetic parameters analysis of anti-B7-H1 antibodies for binding to cynomologus B7-H1

| mAb/CYNO B7H1 | $K_d$ (nM) | $k_{on}$ (M$^{-1}$ s$^{-1}$) | $k_{off}$ (s$^{-1}$) |
|---|---|---|---|
| Reference Antibody #1 | 4.64 | $1.36 \times 10^6$ | 0.0063 |
| 2.7A4OPT | 0.835 | $1.31 \times 10^6$ | 0.0011 |
| 2.14H9OPT | 0.367 | $1 \times 10^6$ | 0.00037 |

Example 16: Epitope Mapping of Anti-B7-H1 Antibodies

Epitope mapping was performed to identify human B7-H1 residues involved in the binding of anti-B7-H1 antibodies. The structure of the extracellular domain of human B7H1 in complex with murine PD1 has been previously described in the literature (Lin, D et al., 2008, Proc. Natl. Acad. Sci. USA, Vol. 105, p3011-3016) and reveals that fourteen B7-H1 residues are involved in the binding to PD1 (Table 23).

TABLE 23

Human B7-H1 residues involve in the binding to murine PD1

| Amino Acid | Position |
|---|---|
| Phe | 19 |
| Thr | 20 |
| Asp | 26 |
| Ile | 54 |
| Tyr | 56 |
| Gln | 66 |

TABLE 23-continued

Human B7-H1 residues involve in the binding to murine PD1

| Amino Acid | Position |
|---|---|
| Arg | 113 |
| Met | 115 |
| Ser | 117 |
| Ala | 121 |
| Asp | 122 |
| Tyr | 123 |
| Lys | 124 |
| Arg | 125 |

Anti-B7-H1 antibodies are competing for the binding of human B7-H1 to human PD1 (Example 5, 8 and 12) so they should interact with some of those 14 residues if we assume that there are negligible differences between the B7H1 binding interface to human and mouse PD1 (62% amino acid identity between the two species extracellular domain sequence). Single amino acid B7-H1 mutants will be generated for all the 14 positions described in Table 23. Mutants will be tested for binding to anti-B7-H1 antibodies by phage ELISA and the ability to compete the binding of anti-B7-H1 antibodies to human B7-H1 in HTRF© competition assays. All anti-B7-H1 antibodies described are in the IgG1-TM format.

Cloning of the Human B7-H1 Extracellular Domain Gene Infusion with Bacteriophage Gene II for Phage Display Expression Gene coding for the extracellular domain of the human B7-H1 protein (Uniprot accession number Q9NZQ7, amino acid [19-238]) has been synthetized externally by DNA2.0 Inc. and amplified by PCR using the primers B7H1_FOR (5'-AATAATGGCCCAGCCGGCCATGGCCTTTACCG-TGACGGTACCG-3'-SEQ ID NO: 154) and B7H1_REV (5'-AATAATGCGGCCGCCCTTTCGTTTGGGGGATGC-3'-SEQ ID NO: 155) to introduce the Sfi I and Not I restriction sites at 5' and 3' ends respectively. PCR product has then been directionally cloned in the pCANTAB6 vector (McCafferty J. et al., 1994, Appl. Biochem. Biotechnol., Vol. 47, p157-173) using Sfi I and Not I restriction sites. *E. coli* strain TG1 were transformed with the ligation and individual colonies were screened by sequencing to identify a B7-H1 transformant named B7-H1_pCANTA6.

Generating and Identifying B7-H1 Mutants

B7-H1 mutants have been generated by saturation mutagenesis at all the 14 residues of the PD1 interface using fully randomised NNS primers (Table 24) and the plasmid B7-H1_pCANTA6 as DNA template. Mutagenesis was performed with the Stratagene's QuickChange Multi Site-Directed Mutagenesis Kit (Catalog #200513) according to the manufacturer's instructions. Mutagenic reactions were used to transform *E. coli* strain TG1 and individual colonies were screened by sequencing to identify B7-H1 variants. A total of 252 variants were identified among the 280 possible (20 amino acids time 14 positions) and cherry picked in 3 96-wells culture plates.

TABLE 24

| Mutagenenic primers used to generate B7-H1 variants | | |
|---|---|---|
| Primer Name | Sequence | SEQ ID NO: |
| B7H1_SDM_F19_f | 5'-GCCGGCCATGGCCNNSACCGTGACGGTACCGAAAG-3' | SEQ ID NO: 156 |
| B7H1_SDM_T20_f | 5'-GCCGGCCATGGCCTTTNNSGTGACGGTACCGAAAG-3' | SEQ ID NO: 157 |
| B7H1_SDM_D26_f | 5'-CCGTGACGGTACCGAAANNSTTGTATGTGGTGGAGTATGG-3' | SEQ ID NO: 158 |
| B7H1_SDM_I54_f | 5'-GGATCTTGCTGCCCTTNNSGTCTACTGGGAAATGGAGGACAAG-3' | SEQ ID NO: 159 |
| B7H1_SDM_Y56_f | 5'-GGATCTTGCTGCCCTTATCGTCNNSTGGGAAATGGAGGACAAG-3' | SEQ ID NO: 160 |
| B7H1_SDM_Q66_f | 5'-GGAGGACAAGAACATCATCNNSTTTGTCCATGGAGAGGAGG-3' | SEQ ID NO: 161 |
| B7H1_SDM_R113_f | 5'-ATGCCGGGGTCTACNNSTGTATGATCTCTTACGGCGG-3' | SEQ ID NO: 162 |
| B7H1_SDM_M115_f | 5'-ATGCCGGGGTCTACCGCTGTNNSATCTCTTACGGCGG-3' | SEQ ID NO: 163 |
| B7H1_SDM_S117_f | 5'-CTACCGCTGTATGATCNNSTACGGCGGTGCCG-3' | SEQ ID NO: 164 |
| B7H1_SDM_A121_f | 5'-GATCTCTTACGGCGGTNNSGATTACAAACGGATAACC-3' | SEQ ID NO: 165 |
| B7H1_SDM_D122_f | 5'-GATCTCTTACGGCGGTGCCNNSTACAAACCGATAACC-3' | SEQ ID NO: 166 |
| B7H1_SDM_Y123_f | 5'-CGGCGGTGCCGATNNSAAACGGATAACCGTAAAGG-3' | SEQ ID NO: 167 |
| B7H1_SDM_K124_f | 5'-CGGCGGTGCCGATTACNNSCGGATAACCGTAAAGG-3' | SEQ ID NO: 168 |
| B7H1_SDM_R125_f | 5'-GCGGTGCCGATTACAAANNSATAACCGTAAAGGTAAACG-3' | SEQ ID NO: 169 |

Phage ELISA of B7-H1 Mutants for Binding to Anti-B7-H1 Antibodies

Binding of the 1B7-1H1 mutants to anti-17-1H1 antibodies 2.141H9OPT, 2.7A4OPT or Reference Ab #1 have been assessed by phage ELISA after assuring that the 1B7-1H1 extracellular domain in fusion with gene III protein could be displayed at the phage surface. Cherry picked TG1 cultures were grown and superinfected with M13K07 helper phage to produce phage particles displaying B7-H1 mutants at their surface. Phage supernatants were blocked in PBS+3% skimmed milk and incubated in NUNC MaxiSorb plates previously coated overnight with 1 ug/mL 2.14H9OPT, 2.7A4OPT or Reference antibody #1 in PBS and blocked with PBS+3% skimmed milk. Bound phages were detected using streptavidin coupled with europium (Perkin Elmer) after incubation with a biotinylated anti-M13 secondary antibody (Progen).

Among the 14 human B7-H1 residues located at the PD1 interface, four are not involved in the binding to any of the three tested anti-B7-H1 antibodies (Asp26, Tyr56, Glu66 and Lys124). Their replacements by an alanine or a glycine do not significantly affect the binding signal. Based on the phage ELISA data, a total of 28 mutants representative of 2 to 3 key changes for each of the 10 others positions have been selected to confirm their binding profile but using purified proteins.

Biochemical Competition Assays

Extracellular domain of human B7-H1 wild-type and mutants were expressed in bacteria and purified by affinity chromatography as previously described (Bannister D. et al., 2006, Biotechnology and bioengineering, 94, 931-937).

The HTRF® competition assays measured the binding of anti-B7-H1 antibody to HIS FLAG tagged B7-H1. Titration of non tagged B7-H1 samples, prepared as described above, will compete with HIS FLAG tagged B7-H1 for binding to anti-B7-H1 antibody, leading to a reduction in assay signal. The antibodies 2.14H9OPT, 2.7A4OPT and Reference antibody #1 were used to establish competition assays for characterising the relative binding of purified wild-type or mutants B7-H1. This will confirm which B7-H1 residues are required for antibody binding. 10 μl of B7-H1 sample was added to a 384 well low volume assay plate (Corning 3673). This was followed by the addition of 5 μL of either 0.29 nM 2.14H9OPT, or 1.15 nM 2.7A4OPT, or 1.15 nM Reference antibody #1 conjugated to DyLight649 according to manufacturer's instructions (ThermoFisher, 53051) and 5 μL of a mixed solution of 0.43 nM anti-FLAG cryptate (Cisbio International, 61FG2KLB) and 1.25 nM HIS FLAG tagged human B7-H1. Assay plates were incubated for 4 hours at room temperature prior to reading time resolved fluorescence at 620 nm and 665 nm emission wavelengths using an EnVision plate reader (Perkin Elmer).

Three additional B7-H1 residues (Ile54, Ser117 and Ala121) are not involved in the binding to 2.14H9OPT and 2.7A4OPT as $IC_{50}$ of B7-H1 mutants for those residues are similar or marginally modified compared to wild-type B7-H1. Competition data to the 3 anti-B7-H1 antibodies for wild-type and all the other B7-H1 mutants are summarised in the Table 25.

TABLE 25

IC$_{50}$ in nM in the human B7-H1 competition assays for binding to anti-B7-H1 antibodies

| B7-H1 sample | Competition assay IC$_{50}$ in nM | | |
| | 2.14H9OPT IgG1-TM | 2.7A4OPT IgG1-TM | Reference Ab#1 |
| --- | --- | --- | --- |
| wild-type B7H1 | 0.76 | 2.79 | 1.89 |
| B7H1_F19A | 0.56 | No inhibition | 27.6 |
| B7H1_F19G | 0.56 | No inhibition | 15.3 |
| B7H1_F19S | 0.66 | No inhibition | 21.6 |
| B7H1_T20A | 0.45 | No inhibition | 2.3 |
| B7H1_T20V | 0.64 | No inhibition | 1.9 |
| B7H1_T20D | 0.83 | No inhibition | 1.9 |
| B7H1_R113A | No inhibition | 4.6 | 172 |
| B7H1_R113Y | No inhibition | No inhibition | 3.9 |
| B7H1_R113L | No inhibition | No inhibition | 2 |
| B7H1_M115A | 3.9 | 6.9 | 86 |
| B7H1_M115G | 30.4 | 4.6 | No inhibition |
| B7H1_M115D | No inhibition | 5.8 | No inhibition |
| B7H1_D122E | 29.6 | No inhibition | 35.2 |
| B7H1_D122N | 15.5 | No inhibition | 2.5 |
| B7H1_Y123A | 232 | 1.77 | No inhibition |
| B7H1_Y123F | 0.5 | 2.21 | No inhibition |
| B7H1_Y123T | 427 | 2.07 | No inhibition |
| B7H1_R125A | No inhibition | 3 | 11.7 |
| B7H1_R125Q | No inhibition | 2.4 | 18.4 |
| B7H1_R125S | No inhibition | 2.7 | 9.7 |

Arg113 and Arg125 are strongly involved in the binding to 2.14H9OPT. Replacement by an Ala or other amino acids (Tyr or Leu at position 113 and Gln or Ser at position 125) lead to a total lost of binding to that antibody. Binding profile of those B7-H1 mutants to 2.7A4OPT or Reference antibody #1 is similar to the wild-type B7-H1. This shows that the lost of binding is not due to a general structural modification of B7-H1 as for instance an unfolded protein but to a direct involvement of those residues with 2.14H9OPT binding. Those data also demonstrate that 2.14H9OPT binding epitope is different from 2.7A4OPT and Reference antibody #1 epitopes. Met115, Asp122 and Tyr123 are also involved in the binding to 2.14H9OPT but to a lesser extend. Replacement of Met115 by an Ala does not affect the binding to 2.14H9OPT or 2.7A4OPT but replacement by an Asn leads to a total lost of binding activity to 2.14H9OPT but not to 2.7A4OPT. In a similar way, replacement of Asp122 by an Asn is affecting the binding to 2.14H9OPT but not to Reference antibody #1. Mutating Tyr123 by an Ala or a Thr greatly modify the binding profile to 2.14H9OPT but not to 2.7A4OPT. Interestingly, a replacement by a Phe does not change the binding to 2.14H9OPT suggesting that the hydroxyl group of the tyrosine 123 is not involved in the binding interaction.

Phe19, Thr20 and Asp122 are strongly involved in the binding to 2.7A4OPT. All B7-H1 mutants at those positions have no binding to that antibody but do bind 2.14H9OPT or Reference antibody #1 in a similar way to wild-type B7-H1, excepted B7H1_D122E mutant which binds those 2 antibodies less efficiently. Those three residues are specifics to the 2.7A4OPT mAb binding epitope and are not shared by the 2.14H9OPT or the Reference antibody #1 epitopes.

Arg113 is also involved in the 2.7A4OPT epitope but to a lesser extend. Replacement by an Ala does not affect the binding to that antibody but a Tyr or Leu mutations lead to a total lost of binding. Those mutations at position 113 do not affect the binding to the Reference antibody #1 showing that B7-H1 mutants are still in a correct conformation. It is possible that the replacement by a bulky amino acid as a Tyr may introduce some steric hindrances. Those results suggest that the Arg113 is not directly involved in the contact to the 2.7A4OPT antibody but is very close to the actual binding epitope.

This example demonstrates that the three anti-B7-H1 antibodies 2.14H9OPT, 2.7A4OPT and Reference antibody #1 have distinct binding epitopes at the B7-H1 interface with PD1. Furthermore, it is possible that those antibodies may also bind to other human B7-H1 residues but which are not located at the PD1 interface.

Example 17. Determination of the Effects of Anti-B7-H1 Antibodies on a Memory T-Cell Response to Sub-Optimal Concentrations of a Recall Antigen B7-H1 interaction with PD-1 has been shown to inhibit antigen specific T-cell responses. In order to assess the effect of anti-B7-H1 antibodies on this inhibition a sub-optimal antigen recall assay was performed.

Figure 6:
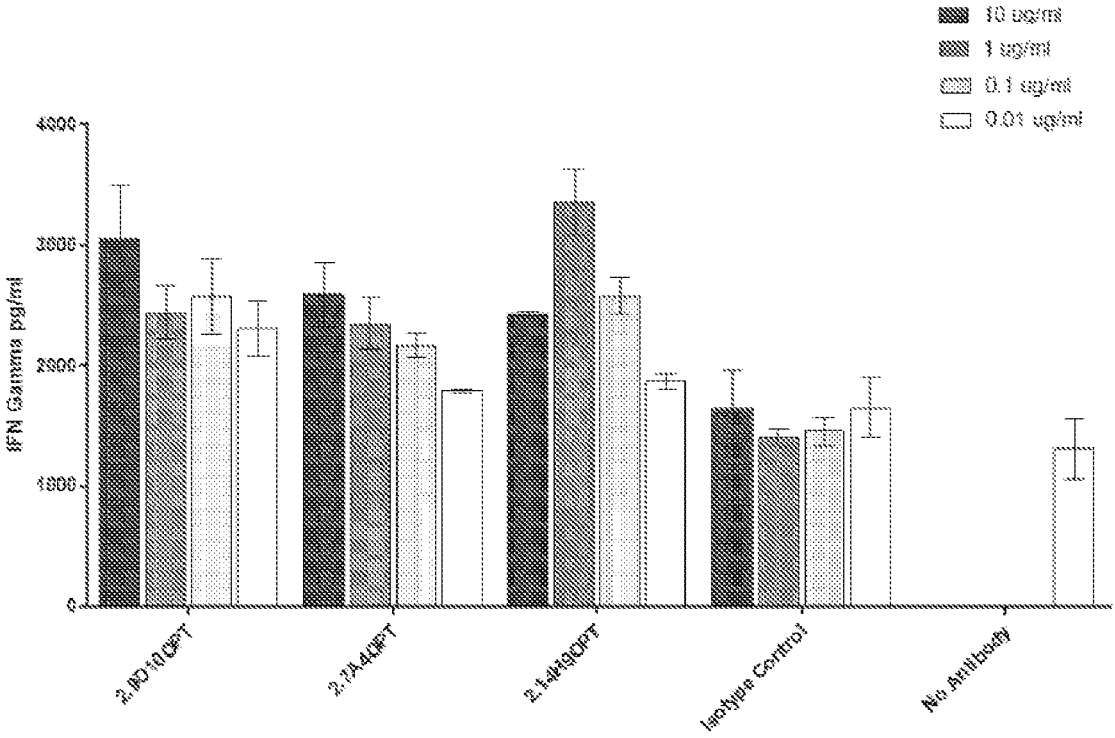
FIG. 6 is a bar graph showing the effects of anti-B7-H1 antibodies of the invention in the in-vitro Tet-recall assay.

Peripheral blood monocytes (PBMCs) were isolated from human blood buffy coats using Ficoll-Paque Plus (GE Healthcare 17-1440-03) density gradient centrifugation as per manufacturers instructions. Following isolation cells were resuspended in RPMI 1640 Glutamax I media (GIBCO, 61870) supplemented with 1% pen/strep (GIBCO, 15140) and 4% Human AB Serum (Invitrogen 34005), and then subsequently cultured in 96 well, round bottom tissue culture plates (Corning, 3799) at 370 C, 5% C02, with or without 0.1 g/mL tetanus toxoid (Calbiochem 582231) at a density of 1×105 cells per well. After three days of culture, anti-B7-H1 antibodies in the IgG1-TM format or isotype control were added at the indicated concentrations and cultures returned to 37° C. for a further 2 days, at which point supernatants were harvested and analysed by DELFIA for levels of interferon-γ. Enhancement of interferon-7 release by anti-B7-H1 antibodies is shown in FIG. 6.

Anti-B7-H1 antibodies 2.9D10, 2.7A4OPT and 2.14H9OPT are able to increase the release of Interferon-γ. This data confirms the ability of 2.9D10, 2.7A4OPT and 2.14H9OPT to enhance antigen specific T-cell responses.

Example 18. Determination of the Effects of Anti-B7-H1 Antibodies on a Memory T-Cell Response to Optimal Concentrations of a Recall Antigen B7-H1 has been suggested to have potential inhibitory signalling properties. The potential for anti-B7-H1 antibodies to act as agonist that might drive such inhibitory signalling was tested by examining their ability to inhibit an antigen recall response.

Peripheral blood monocytes (PBMCs) were isolated from a human blood buffy coats using Ficoll-Paque Plus (GE Healthcare 17-1440-03) density gradient centrifugation as per manufacturers instructions. Following isolation cells were resuspended in RPMI 1640 Glutamax I media (GIBCO, 61870) supplemented with 1% pen/strep (GIBCO, 15140) and 4% Human AB Serum (Invitrogen 34005), and then subsequently cultured, at a density of 1×105 cells per well, in 96 well, round bottom tissue culture plates (Corning, 3799) at 370 C, 5% C02, together with 5 g/mL tetanus toxoid (Calbiochem 582231) and in the presence or absence of varying concentrations of anti-B7-H1 antibodies in the IgG1-TM format or isotype control. An antibody against a T-cell co-receptor has been used as positive control. Following 5 days of culture cells were pulsed with 0.5 µCi/well tritiated thymidine for approximately 16 hours in order to assess proliferative activity.

Figure 7:
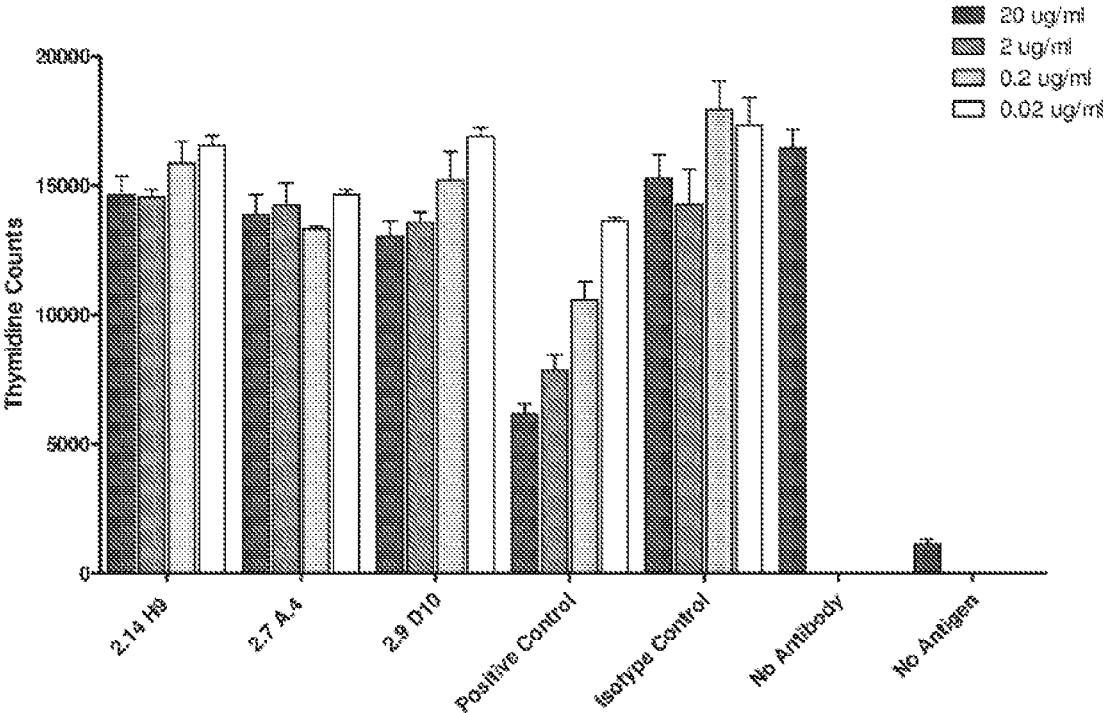
FIG. 7 is a bar graph showing the results form testing agonism activity of anti-B7-H1 antibodies of the invention using the Tet-recall assay.

No inhibitory effects were observed with 2.9D10, 2.7A4 and 2.14H9 anti-B7-H1 antibodies, in contrast to positive control, as shown in FIG. 7. This suggests that 2.9D10, 2.7A4 and 2.14H9 antibodies are pure antagonists, without any agonistic activity.

Example 19. Tumor Growth Inhibition Activity of Anti-B7-H1 Antibodies

The in-vivo activity of anti-human B7-H1 antibodies was investigated in xenograft mouse models using immunocompromised NOD/SCID (non-obese diabetic/severe combined immunodeficiency) mice. The mice were engrafted subcutaneously (SC) with human cancer cell lines expressing human B7-H1 and human CD4+ and CD8+ T cells that were isolated from peripheral blood mononuclear cells of healthy donors and cultured to enrich for alloreactive effector T cells. Intraperiteneal (IP) doses of anti-human B7-H1 antibodies were given to mice inoculated with the human pancreatic cancer cell line HPAC or the human melanoma cell line A375. Effect of the antibodies was observed on tumor growth until a 2000 mm$^3$ tumor volume or gross tumor necrosis.

To generate CD4+ and CD8+ T cell lines, human PBMC's from healthy donors were enriched for CD4+ or CD8+ T cells by the addition of 1 mL RosetteSep T cell enrichment product per 20 mL of whole blood. This was followed by a 20-minute incubation and subsequent isolation by density gradient centrifugation using RosetteSep DM-L density medium. After centrifugation, the cells were washed with PBS and resuspended in RPMI 1640 medium supplemented with 10% FBS. Enriched CD4+ and CD8+ T cells were cultured separately for 7-10 days in medium supplemented with rhIL-2 and each combined with mitomyosin C treated A375 or HPAC cells. T cells were collected and separately cultured again for 7-10 days in medium supplemented with rhIL-2 and combined with mitomyosin C treated A375 or HPAC cells. CD4+ and CD8+ T cells were collected and combined at a 1:1 ratio.

A375 and HPAC cancer cell lines and PBMC enriched for CD4+ and CD8+ T cells were mixed immediately before subcutaneous (SC) administration at the indicated effector-to-target (E:T) ratios. The inoculation number of cells for each cancer cell line was predetermined by empirical tumor forming dose studies; in general, 2.5×10$^6$ cells in a total volume of 0.2 mL were engrafted into each animal.

Six animals were assigned to each experimental group. The animals received an isotype control human IgG2a or IgG1OPT (also referred to herein as "IgG1TM") antibody or the anti-B7-H1 antibodies 2.14H9 IgG2a, 2.14H9OPT, 2.7A4OPT or Reference antibody #1 in the IgG1OPT format. A total of eight independent experiments have been carried out and study designs for each experiment are presented in Tables 26-33. Described anti-B7-H1 antibodies are in the IgG1OPT format except where specified.

The first dose (200 µL) of test article was administered IP 1 hour after engraftment of cancer/effector T cells; the animals received up to 4 additional doses of the test article on study days 3, 5, 8 and/or 10. As a positive control to enhance alloreactivity in some studies, rhIL-2 was administered IP 1 hour after engraftment of cancer/effector T cells; the animals received 4 additional daily doses of rhIL-2 for 4 consecutive days. The formation of tumor was observed in each animal one or two times a week. Tumors were measured by caliper; tumor volumes (V) were calculated using the following formula:

$$V \ (mm^3)=0.5(length \ (mm) \times width \ (mm) \times width \ (mm)/2).$$

For each group, the results are reported as the arithmetic mean. Anticancer effect, expressed as a percent tumor growth inhibition (TGI), was calculated by the following method:

$$\% \ TGI=[1-(mean \ tumor \ V \ of \ treatment \ group) \div (mean \ tumor \ V \ of \ control \ group)] \times 100.$$

In Study 1, anti-B7-H1 antibodies 2.14H9 IgG2a and 2.7A4OPT significantly inhibited the growth of HPAC (pancreas) cancer cells at day 30 by up to 61% and 50% respectively as compared to the isotype control group (FIG. 8 and Table 26).

TABLE 26

Study 1-Treatment groups and percent Tumor Growth Inhibition in mice engrafted with HPAC cancer cells following intravenous administration of anti-B7-H1 antibodies

| Group | Test Article | Dose (mg/kg/mouse) | % TGI at day 30 |
|---|---|---|---|
| 1 | None | NA | NA |
| 2 | None | NA | NA |
| 3 | rhIL-2 | 10$^5$ U/dose | NA |
| 4 | Isotype human IgG2a | 20 | NA |
| 5 | Isotype human IgG1OPT | 20 | NA |
| 6 | 2.14H9 IgG2a | 20 | 50 |
| 7 | 2.14H9 IgG2a | 10 | 22 |
| 8 | 2.14H9 IgG2a | 1 | 56 |
| 9 | 2.14H9 IgG2a | 0.1 | 61 |
| 10 | 2.7A4OPT | 20 | <1 |
| 11 | 2.7A4OPT | 10 | 30 |
| 12 | 2.7A4OPT | 1 | 50 |
| 13 | 2.7A4OPT | 0.1 | 15 |

NA = not applicable

In Study 2, anti-17-1H1 antibodies 2.141H9OPT and 2.7A4OPT inhibited the growth of TIPAC (pancreas) cancer cells at day 39 by up to 7000 and 68% respectively as compared to the 5 isotype control group (FIG. 9 and Table 27).

TABLE 27

Study 2-Treatment groups and percent Tumor Growth Inhibition in mice engrafted with HPAC cancer cells following intravenous administration of anti-B7-H1 antibodies

| Group | Test Article | Dose (mg/kg/mouse) | % TGI at day 39 |
|---|---|---|---|
| 1 | None | NA | NA |
| 2 | None | NA | NA |
| 3 | rhIL-2 | 10$^5$ U/dose | NA |
| 4 | Isotype human IgG1OPT | 20 | NA |
| 5 | 2.14H9OPT | 20 | 67 |
| 6 | 2.14H9OPT | 10 | 28 |
| 7 | 2.14H9OPT | 1 | 63 |
| 8 | 2.14H9OPT | 0.1 | 70 |

TABLE 27-continued

Study 2-Treatment groups and percent Tumor Growth Inhibition in mice engrafted with HPAC cancer cells following intravenous administration of anti-B7-H1 antibodies

| Group | Test Article | Dose (mg/kg/mouse) | % TGI at day 39 |
|-------|--------------|--------------------|-----------------|
| 9 | 2.7A4OPT | 20 | 54 |
| 10 | 2.7A4OPT | 10 | 61 |
| 11 | 2.7A4OPT | 1 | 50 |
| 12 | 2.7A4OPT | 0.1 | 68 |

NA = not applicable

In Study 3, anti-17-1H1 antibody 2.141H9OPT significantly inhibited the growth of HPAC (pancreas) cancer cells at day 30 by up to 6000 as compared to the isotype control group (FIG. 10 and Table 28).

TABLE 28

Study 3-Treatment groups and percent Tumor Growth Inhibition in mice engrafted with HPAC cancer cells following intravenous administration of anti-B7-H1 antibodies

| Group | Test Article | Dose (mg/kg/mouse) | % TGI at day 30 |
|-------|--------------|--------------------|-----------------|
| 1 | None | NA | NA |
| 2 | None | NA | NA |
| 3 | rhIL-2 | $10^5$ U/dose | NA |
| 4 | Isotype human IgG1OPT | 5 | NA |
| 5 | Reference antibody#1 | 5 | 37 |
| 6 | 2.14H9OPT | 5 | 60 |
| 7 | 2.14H9OPT | 1 | 57 |
| 8 | 2.14H9OPT | 0.1 | 57 |
| 9 | 2.14H9OPT | 0.01 | 26 |

NA = not applicable

Figure 11:
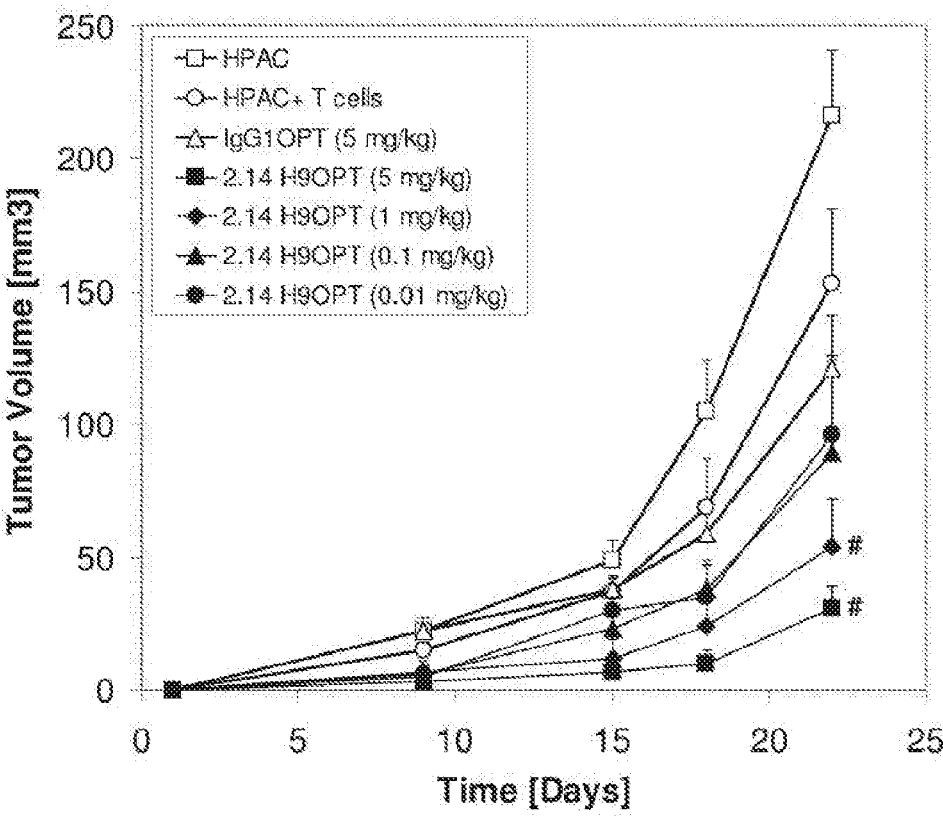
FIG. 11 is a line graph showing the effect of anti-B7-H1 antibodies of the invention on HPAC cells in a mouse xenograft model.

In Study 4 anti-B7-H1 antibody 2.14H9OPT significantly inhibited the growth of HPAC (pancreas) cancer cells at day 22 by up to 7400 as compared to the isotype control group (FIG. 11 and Table 29).

TABLE 29

Study 4-Treatment groups and percent Tumor Growth Inhibition in mice engrafted with HPAC cancer cells following intravenous administration of anti-B7-H1 antibodies

| Group | Test Article | Dose (mg/kg/mouse) | % TGI at day 22 |
|-------|--------------|--------------------|-----------------|
| 1 | None | NA | NA |
| 2 | None | NA | NA |
| 3 | Human IgG1OPT | 5 | NA |
| 4 | 2.14 H9OPT | 5 | 74 |
| 5 | 2.14 H9OPT | 1 | 55 |
| 6 | 2.14 H9OPT | 0.1 | 26 |
| 7 | 2.14 H9OPT | 0.01 | 21 |

In Study 5, IP administration of 2.14H9 IgG2a or 2.7OPT anti-B7-H1 antibodies in the A375 (melanoma) xenograft model also significantly inhibited tumor growth at day 29 by as much as 6400 and 61% respectively as compared to the isotype control group (FIG. 12 and Table 30).

TABLE 30

Study-5. Treatment groups and percent Tumor Growth Inhibition in mice engrafted with A375 cancer cells following intravenous administration of anti-B7-H1 antibodies

| Group | Test Article | Dose (mg/kg/mouse) | % TGI at day 29 |
|-------|--------------|--------------------|-----------------|
| 1 | None | NA | NA |
| 2 | rhIL-2 | $10^5$ U/dose | NA |
| 3 | Isotype human IgG2a | 10 | NA |
| 4 | Isotype human IgG2a | 1 | NA |
| 5 | Isotype human IgG2a | 0.1 | NA |
| 6 | Isotype human IgG1OPT | 10 | NA |
| 7 | Isotype human IgG1OPT | 1 | NA |
| 8 | Isotype human IgG1OPT | 0.1 | NA |
| 9 | 2.14H9 IgG2a | 10 | 54 |
| 10 | 2.14H9 IgG2a | 1 | 37 |
| 11 | 2.14H9 IgG2a | 0.1 | 64 |
| 12 | 2.7A4OPT | 10 | 21 |
| 13 | 2.7A4OPT | 1 | 61 |
| 14 | 2.7A4OPT | 0.1 | 55 |

NA = not applicable

In Study 6, anti-B7-H1 antibody 2.14H9OPT significantly inhibited the growth of A375 (melanoma) cancer cells when combined with T cells at day 25 by up to 77% as compared to the isotype control group (FIG. 13 and Table 31).

TABLE 31

Study-6. Treatment groups and percent Tumor Growth Inhibition in mice engrafted with A375 cancer cells following intravenous administration of anti-B7-H1 antibodies

| Group | Test Article | Dose (mg/kg/mouse) | % TGI at day 25 |
|-------|--------------|--------------------|-----------------|
| 1 | None | NA | NA |
| 2 | None | NA | NA |
| 3 | Human IgG1OPT | 5 | NA |
| 4 | Human IgG1OPT; no T cells | 5 | NA |
| 5 | 2.14 H9OPT | 5 | 67 |
| 6 | 2.14 H9OPT | 1 | 77 |
| 7 | 2.14 H9OPT | 0.1 | 72 |
| 8 | 2.14 H9OPT; no T cells | 1 | 13 |
| 9 | 2.14 H9OPT; no T cells | 0.1 | 25 |

NA = not applicable

In Study 7, anti-B7-H1 antibody 2.14H9OPT significantly inhibited the growth of A375 (melanoma) cancer cells when combined with T cells at day 25 by up to 82% as compared to the isotype control group (FIG. 14 and Table 32).

TABLE 32

Study-7. Treatment groups and percent Tumor Growth Inhibition in mice engrafted with A375 cancer cells following intravenous administration of anti-B7-H1 antibodies

| Group | Test Article | Dose (mg/kg/mouse) | % TGI at day 25 |
|-------|--------------|--------------------|-----------------|
| 1 | None | NA | NA |
| 2 | None | NA | NA |
| 3 | Human IgG1OPT | 5 | NA |
| 4 | Human IgG1OPT; no T cells | 5 | NA |
| 5 | 2.14 H9OPT | 5 | 55 |
| 6 | 2.14 H9OPT | 1 | 82 |
| 7 | 2.14 H9OPT | 0.1 | 72 |
| 8 | 2.14 H9OPT; no T cells | 1 | 36 |
| 9 | 2.14 H9OPT; no T cells | 0.1 | 27 |

NA = not applicable

Figure 15:
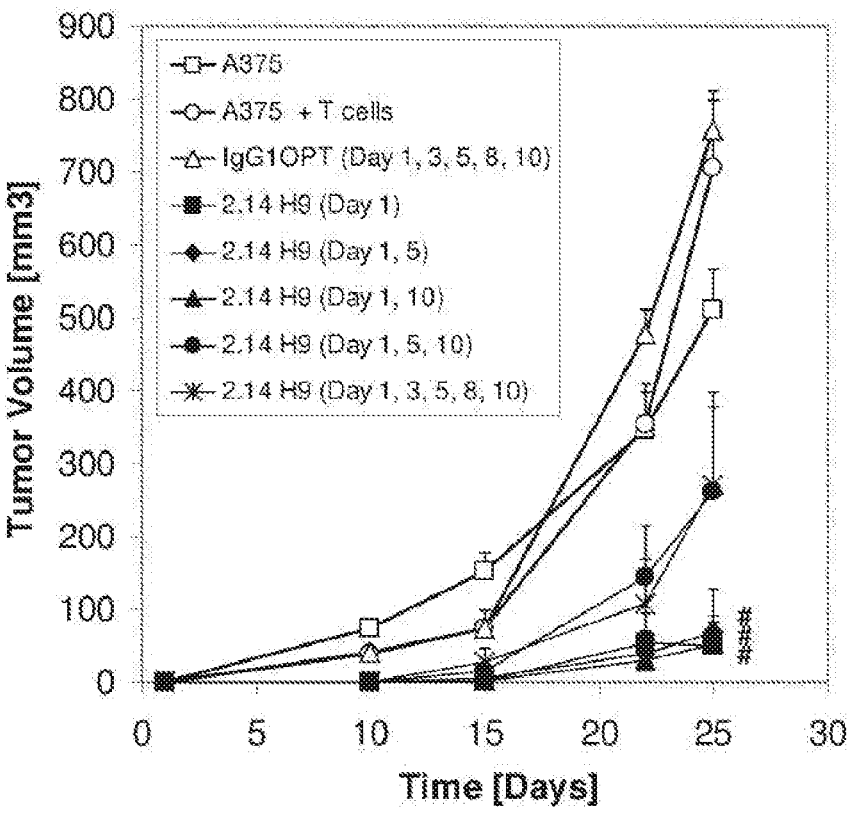
FIG. 15 is a line graph showing the effect of anti-B7-H1 antibodies of the invention on A375 cells in a mouse xenograft model.

In Study 8, anti-B7-H1 antibody 2.14H9OPT significantly inhibited the growth of A375 (melanoma) cancer cells when combined with T cells at day 25 by up to 93% as compared to the isotype control group (FIG. 15 and Table 33).

TABLE 33

Study-8. Treatment groups and percent Tumor Growth Inhibition in mice engrafted with A375 cancer cells following intravenous administration of anti-B7-H1 antibodies

| Group | Test Article | Dose (mg/kg/mouse) | Dose Schedule (Study Day) | % TGI at day 25 |
|---|---|---|---|---|
| 1 | None | NA | NA | NA |
| 2 | None | NA | NA | NA |
| 3 | Human IgG1OPT | 1 | 1, 3, 5, 8, 10 | NA |
| 4 | 2.14 H9OPT | 1 | 1 | 93 |
| 5 | 2.14 H9OPT | 1 | 1, 5 | 91 |
| 6 | 2.14 H9OPT | 1 | 1, 10 | 93 |
| 7 | 2.14 H9OPT; no T cells | 1 | 1, 5, 10 | 66 |
| 8 | 2.14 H9OPT; no T cells | 1 | 1, 3, 5, 8, 10 | 64 |

NA = not applicable

These results demonstrated that the anti-human B7-H1 antibodies 2.14H9 IgG2a, 2.14H9OPT and 2.7A4OPT have potent in vivo anticancer activity in xenograft mouse models of human cancers and provide evidence that those anti-human B7-H1 antibodies can have activity as a single-agent therapy for the treatment of patients with cancers expressing B7-H1.

INCORPORATION BY REFERENCE

All references cited herein, including patents, patent applications, papers, text books, and the like, and the references cited therein, to the extent that they are not already, are hereby incorporated herein by reference in their entirety. U.S. provisional patent application Ser. No. 61/264,061 filed Nov. 24, 2009, the figures and the sequences therein are hereby incorporated by reference in its entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

SEQUENCE LISTING

```
Sequence total quantity: 80
SEQ ID NO: 1              moltype = DNA  length = 360
FEATURE                   Location/Qualifiers
misc_feature              1..360
                          note = Synthetic
source                    1..360
                          mol_type = other DNA
                          organism = synthetic construct
SEQUENCE: 1
gaggtgcagc tggtcgagtc tggcggcgga ctggtgaagc ctggcggctc cctgagactg   60
tcttgcgccg ccagtggctt tacattcagt acctactcca tgaactgggt ccgccaggca  120
ccaggcaagg gcctggaatg ggtgtcctcc atctcatcca gtggcgacta catctactac  180
gccgactccg tgaagggccg gttcaccatc tcccgggaca acgccaagaa ctccctgttc  240
ctgcagatga actccctgaa ggccgaggac accgccgtgt actactgcgc cagggacctg  300
gtgacatcca tggtggcctt cgactactgg ggtcagggca ctctcgtcac agtgtcctct  360

SEQ ID NO: 2              moltype = AA  length = 120
FEATURE                   Location/Qualifiers
REGION                    1..120
                          note = Synthetic
source                    1..120
                          mol_type = protein
                          organism = synthetic construct
SEQUENCE: 2
EVQLVESGGG LVKPGGSLRL SCAASGFTFS TYSMNWVRQA PGKGLEWVSS ISSSGDYIYY   60
ADSVKGRFTI SRDNAKNSLF LQMNSLKAED TAVYYCARDL VTSMVAFDYW GQGTLVTVSS  120

SEQ ID NO: 3              moltype = AA  length = 5
FEATURE                   Location/Qualifiers
REGION                    1..5
                          note = Synthetic
source                    1..5
                          mol_type = protein
                          organism = synthetic construct
SEQUENCE: 3
TYSMN                                                                 5

SEQ ID NO: 4              moltype = AA  length = 17
FEATURE                   Location/Qualifiers
REGION                    1..17
                          note = Synthetic
source                    1..17
                          mol_type = protein
                          organism = synthetic construct
SEQUENCE: 4
```

-continued

```
SISSSGDYIY YADSVKG                                                      17

SEQ ID NO: 5             moltype = AA  length = 11
FEATURE                  Location/Qualifiers
REGION                   1..11
                         note = Synthetic
source                   1..11
                         mol_type = protein
                         organism = synthetic construct
SEQUENCE: 5
DLVTSMVAFD Y                                                            11

SEQ ID NO: 6             moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 6
tcttacgagc tgacccagcc tccttccgtg tccgtgtctc caggacaggc agccagaatc  60
acctgttccg gcgacgccct gcctcagaaa tacgtgttct ggtatcagca gaagtccggc 120
caggcccctg tgctggtgat ctacgaggac tccaagcggc cttccggcat ccctgagcgg 180
ttctccggct cctcttccgg caccatggcc accctgacca tctctggcgc ccaggtggag 240
gacgaggcca actactactg ctactccacc gacagatccg gcaaccacag agtgtttggt 300
gggggtacta gactgaccgt gctg                                          324

SEQ ID NO: 7             moltype = AA  length = 108
FEATURE                  Location/Qualifiers
REGION                   1..108
                         note = Synthetic
source                   1..108
                         mol_type = protein
                         organism = synthetic construct
SEQUENCE: 7
SYELTQPPSV SVSPGQAARI TCSGDALPQK YVFWYQQKSG QAPVLVIYED SKRPSGIPER  60
FSGSSSGTMA TLTISGAQVE DEADYYCYST DRSGNHRVFG GGTRLTVL               108

SEQ ID NO: 8             moltype = AA  length = 11
FEATURE                  Location/Qualifiers
REGION                   1..11
                         note = Synthetic
source                   1..11
                         mol_type = protein
                         organism = synthetic construct
SEQUENCE: 8
SGDALPQKYV F                                                            11

SEQ ID NO: 9             moltype = AA  length = 7
FEATURE                  Location/Qualifiers
REGION                   1..7
                         note = Synthetic
source                   1..7
                         mol_type = protein
                         organism = synthetic construct
SEQUENCE: 9
EDSKRPS                                                                  7

SEQ ID NO: 10            moltype = AA  length = 11
FEATURE                  Location/Qualifiers
REGION                   1..11
                         note = Synthetic
source                   1..11
                         mol_type = protein
                         organism = synthetic construct
SEQUENCE: 10
YSTDRSGNHR V                                                            11

SEQ ID NO: 11            moltype = DNA  length = 360
FEATURE                  Location/Qualifiers
misc_feature             1..360
                         note = Synthetic
source                   1..360
                         mol_type = other DNA
                         organism = synthetic construct
SEQUENCE: 11
gaggtgcagc tggtcgagtc tggcggagga ctggtgcagc ctggcggctc cctgagactg  60
tcttgcgctc cttccggatt caccttctcc tcctactgga tgtcctgggt cgcgcaggct 120
cctggcaagg gactggaatg ggtggccaac atcaagcagg acggcggcga gcagtactac 180
```

-continued

```
gtggactccg tgaagggccg gttcaccatc tcccgggaca acgccaagaa ctccctgtac   240
ctgcagatga actccctgag ggccgaggac accgccgtgt actactgcgc cagagactgg   300
aactacggct actacgacat ggacgtgtgg ggccagggca ccaccgtgac agtgtcctct   360

SEQ ID NO: 12        moltype = AA  length = 120
FEATURE              Location/Qualifiers
REGION               1..120
                     note = Synthetic
source               1..120
                     mol_type = protein
                     organism = synthetic construct
SEQUENCE: 12
EVQLVESGGG LVQPGGSLRL SCAASGFTFS SYWMSWVRQA PGKGLEWVAN IKQDGGEQYY   60
VDSVKGRFTI SRDNAKNSLY LQMNSLRAED TAVYYCARDW NYGYYDMDVW GQGTTVTVSS  120

SEQ ID NO: 13        moltype = AA  length = 5
FEATURE              Location/Qualifiers
REGION               1..5
                     note = Synthetic
source               1..5
                     mol_type = protein
                     organism = synthetic construct
SEQUENCE: 13
SYWMS                                                                5

SEQ ID NO: 14        moltype = AA  length = 17
FEATURE              Location/Qualifiers
REGION               1..17
                     note = Synthetic
source               1..17
                     mol_type = protein
                     organism = synthetic construct
SEQUENCE: 14
NIKQDGGEQY YVDSVKG                                                  17

SEQ ID NO: 15        moltype = AA  length = 11
FEATURE              Location/Qualifiers
REGION               1..11
                     note = Synthetic
source               1..11
                     mol_type = protein
                     organism = synthetic construct
SEQUENCE: 15
DWNYGYYDMD V                                                        11

SEQ ID NO: 16        moltype = DNA  length = 324
FEATURE              Location/Qualifiers
misc_feature         1..324
                     note = Synthetic
source               1..324
                     mol_type = other DNA
                     organism = synthetic construct
SEQUENCE: 16
gagatcgtgc tgacccagtc ccctggcacc ctgtctctgt ctcccggcga gagagccacc   60
ctgtcttgcc gggcctccca gtccgtgtcc tccaactacc tcgcctggtt ccagcagaaa  120
cccggtcagg cccctagact gctgatcttc ggcacctcct ccagagccac cggcatccct  180
gaccggttct ccggctctgg ctccggcacc gacttcaccc tgaccatctc caggctggaa  240
cctgaggact tcgctgtgta ctattgccag cagtacggct cctccatctt caccttcgga  300
ccaggaacaa aggtcgacat caaa                                         324

SEQ ID NO: 17        moltype = AA  length = 108
FEATURE              Location/Qualifiers
REGION               1..108
                     note = Synthetic
source               1..108
                     mol_type = protein
                     organism = synthetic construct
SEQUENCE: 17
EIVLTQSPGT LSLSPGERAT LSCRASQSVS SNYLAWFQQK PGQAPRLLIF GTSSRATGIP   60
DRFSGSGSGT DFTLTISRLE PEDFAVYYCQ QYGSSIFTFG PGTKVDIK              108

SEQ ID NO: 18        moltype = AA  length = 12
FEATURE              Location/Qualifiers
REGION               1..12
                     note = Synthetic
source               1..12
                     mol_type = protein
                     organism = synthetic construct
SEQUENCE: 18
```

```
RASQSVSSNY LA                                                             12

SEQ ID NO: 19          moltype = AA   length = 7
FEATURE                Location/Qualifiers
REGION                 1..7
                       note = Synthetic
source                 1..7
                       mol_type = protein
                       organism = synthetic construct
SEQUENCE: 19
GTSSRAT                                                                   7

SEQ ID NO: 20          moltype = AA   length = 9
FEATURE                Location/Qualifiers
REGION                 1..9
                       note = Synthetic
source                 1..9
                       mol_type = protein
                       organism = synthetic construct
SEQUENCE: 20
QQYGSSIFT                                                                 9

SEQ ID NO: 21          moltype = DNA  length = 363
FEATURE                Location/Qualifiers
misc_feature           1..363
                       note = Synthetic
source                 1..363
                       mol_type = other DNA
                       organism = synthetic construct
SEQUENCE: 21
gaggtgcagc tggtcgagtc tggcggagga ctggtgcagc ctggcggctc cctgagactg        60
tcttgcgccg cctccggctt caccttctcc cggtactgga tgtcttgggt gcgccaggct       120
cctggcaagg gactggaatg ggtggccaac atcaaacagg atggctctga gaagtactac       180
gtggactccg tgaagggccg gttcaccatc tccaggggaca acgccaagaa ctccctgtac      240
ctgcagatga actccctgag ggccgaggac accgccgtgt actactgcgc ccgggagggc       300
ggatggttcg gcgagctggc cttcgattac tggggccagg gcaccctggt gacagtgtcc       360
tct                                                                      363

SEQ ID NO: 22          moltype = AA   length = 121
FEATURE                Location/Qualifiers
REGION                 1..121
                       note = Synthetic
source                 1..121
                       mol_type = protein
                       organism = synthetic construct
SEQUENCE: 22
EVQLVESGGG LVQPGGSLRL SCAASGFTFS RYWMSWVRQA PGKGLEWVAN IKQDGSEKYY         60
VDSVKGRFTI SRDNAKNSLY LQMNSLRAED TAVYYCAREG GWFGELAFDY WGQGTLVTVS        120
S                                                                        121

SEQ ID NO: 23          moltype = AA   length = 5
FEATURE                Location/Qualifiers
REGION                 1..5
                       note = Synthetic
source                 1..5
                       mol_type = protein
                       organism = synthetic construct
SEQUENCE: 23
RYWMS                                                                    5

SEQ ID NO: 24          moltype = AA   length = 17
FEATURE                Location/Qualifiers
REGION                 1..17
                       note = Synthetic
source                 1..17
                       mol_type = protein
                       organism = synthetic construct
SEQUENCE: 24
NIKQDGSEKY YVDSVKG                                                       17

SEQ ID NO: 25          moltype = AA   length = 12
FEATURE                Location/Qualifiers
REGION                 1..12
                       note = Synthetic
source                 1..12
                       mol_type = protein
                       organism = synthetic construct
SEQUENCE: 25
EGGWFGELAF DY                                                            12
```

```
SEQ ID NO: 26            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 26
gagatcgtgc tgacccagtc ccctggcacc ctgtctctgt ctcccggcga gagagccacc   60
ctgtcttgcc gggcctccca gcgggtgtcc tcctcctacc tggcctggta tcagcagaaa  120
cccggacagg cccctaggct gctgatctac gacgcctcct ccagagccac cggcatccct  180
gaccggttct ccggctctgg ctccggcacc gacttcaccc tgaccatctc ccggctggaa  240
cctgaggact ttgccgtgta ttactgccag cagtacggct ccctgccttg gaccttcggc  300
cagggaaccg aggtggagat caaa                                         324

SEQ ID NO: 27            moltype = AA  length = 108
FEATURE                  Location/Qualifiers
REGION                   1..108
                         note = Synthetic
source                   1..108
                         mol_type = protein
                         organism = synthetic construct
SEQUENCE: 27
EIVLTQSPGT LSLSPGERAT LSCRASQRVS SSYLAWYQQK PGQAPRLLIY DASSRATGIP   60
DRFSGSGSGT DFTLTISRLE PEDFAVYYCQ QYGSLPWTFG QGTEVEIK              108

SEQ ID NO: 28            moltype = AA  length = 12
FEATURE                  Location/Qualifiers
REGION                   1..12
                         note = Synthetic
source                   1..12
                         mol_type = protein
                         organism = synthetic construct
SEQUENCE: 28
RASQRVSSSY LA                                                       12

SEQ ID NO: 29            moltype = AA  length = 7
FEATURE                  Location/Qualifiers
REGION                   1..7
                         note = Synthetic
source                   1..7
                         mol_type = protein
                         organism = synthetic construct
SEQUENCE: 29
DASSRAT                                                              7

SEQ ID NO: 30            moltype = AA  length = 9
FEATURE                  Location/Qualifiers
REGION                   1..9
                         note = Synthetic
source                   1..9
                         mol_type = protein
                         organism = synthetic construct
SEQUENCE: 30
QQYGSLPWT                                                            9

SEQ ID NO: 31            moltype = DNA  length = 363
FEATURE                  Location/Qualifiers
misc_feature             1..363
                         note = Synthetic
source                   1..363
                         mol_type = other DNA
                         organism = synthetic construct
SEQUENCE: 31
gaggtgcagc tgttggagtc tgggggaggc ttggtacagc ctggggggtc cctgagactc   60
tcctgtgcag cctctggatt cacctttagc aactatgcca tgagttgggt ccgccaggct  120
ccagggaagg ggctggagtg ggtctcggct attcgtggta gtggtggtag cacatactac  180
gcagactccg tgaagggccg gttcaccatc tccagagaca attccaagaa cacgctgtat  240
ctgcaaatga acagcctgag agccgaggac acggccgtat attactgtgc gaaagatctt  300
cactatgata gtagtggtta tcttgactac tggggccagg gaaccctggt caccgtctcc  360
tca                                                                363

SEQ ID NO: 32            moltype = AA  length = 121
FEATURE                  Location/Qualifiers
REGION                   1..121
                         note = Synthetic
source                   1..121
                         mol_type = protein
```

```
                         organism = synthetic construct
SEQUENCE: 32
EVQLLESGGG LVQPGGSLRL SCAASGFTFS NYAMSWVRQA PGKGLEWVSA IRGSGGSTYY   60
ADSVKGRFTI SRDNSKNTLY LQMNSLRAED TAVYYCAKDL HYDSSGYLDY WGQGTLVTVS   120
S                                                                  121

SEQ ID NO: 33           moltype = AA  length = 5
FEATURE                 Location/Qualifiers
REGION                  1..5
                        note = Synthetic
source                  1..5
                        mol_type = protein
                        organism = synthetic construct
SEQUENCE: 33
NYAMS                                                              5

SEQ ID NO: 34           moltype = AA  length = 17
FEATURE                 Location/Qualifiers
REGION                  1..17
                        note = Synthetic
source                  1..17
                        mol_type = protein
                        organism = synthetic construct
SEQUENCE: 34
AIRGSGGSTY YADSVKG                                                 17

SEQ ID NO: 35           moltype = AA  length = 12
FEATURE                 Location/Qualifiers
REGION                  1..12
                        note = Synthetic
source                  1..12
                        mol_type = protein
                        organism = synthetic construct
SEQUENCE: 35
DLHYDSSGYL DY                                                      12

SEQ ID NO: 36           moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 36
gacatccaga tgacccagtc tccatcttcc gtgtctgcat ctgtaggaga cagagtcacc   60
atcacttgtc gggcgagtca gggtattcgc agctggttag cctggtatca gcagaaaccg   120
gggaaagccc ctaagctcct gatctatgct atatccaggt tgcaaagtgg ggtcccatca   180
aggtttagcg gcagtgggtc tgggacagat ttcactctca ccatcagcag cctgcagcct   240
gaagattttg caacttacta ttgtcaacag gctaacagtt tccctctcac tttcggcgga   300
gggaccaagg tggagatcaa a                                             321

SEQ ID NO: 37           moltype = AA  length = 107
FEATURE                 Location/Qualifiers
REGION                  1..107
                        note = Synthetic
source                  1..107
                        mol_type = protein
                        organism = synthetic construct
SEQUENCE: 37
DIQMTQSPSS VSASVGDRVT ITCRASQGIR SWLAWYQQKP GKAPKLLIYA ISRLQSGVPS   60
RFSGSGSGTD FTLTISSLQP EDFATYYCQQ ANSFPLTFGG GTKVEIK                  107

SEQ ID NO: 38           moltype = AA  length = 11
FEATURE                 Location/Qualifiers
REGION                  1..11
                        note = Synthetic
source                  1..11
                        mol_type = protein
                        organism = synthetic construct
SEQUENCE: 38
RASQGIRSWL A                                                       11

SEQ ID NO: 39           moltype = AA  length = 7
FEATURE                 Location/Qualifiers
REGION                  1..7
                        note = Synthetic
source                  1..7
                        mol_type = protein
                        organism = synthetic construct
```

-continued

```
SEQUENCE: 39
AISRLQS                                                                7

SEQ ID NO: 40            moltype = AA   length = 9
FEATURE                  Location/Qualifiers
REGION                   1..9
                         note = Synthetic
source                   1..9
                         mol_type = protein
                         organism = synthetic construct
SEQUENCE: 40
QQANSFPLT                                                              9

SEQ ID NO: 41            moltype = DNA   length = 357
FEATURE                  Location/Qualifiers
misc_feature             1..357
                         note = Synthetic
source                   1..357
                         mol_type = other DNA
                         organism = synthetic construct
SEQUENCE: 41
gaggtgcagc tggtggagtc tggggggaggc ttggtccagc ctggggggtc cctgagactc   60
tcctgtgcag cctctggatt caccttttagt agctattgga tgagctgggt ccgccaggct  120
ccagggaagg ggctgagtg ggtggccaac ataaagcaag atggaggtga gaaatactat  180
gtggactctg tgaagggccg attcaccatc tccagagaca acgccaagaa ctcactgttt  240
ctgcaaatga acagcctgag agccgaggac acggctgtct attactgtgc gagagttcag  300
ctctacagtg actactttga ctactggggc cagggaaccc tggtcaccgt ctcctct     357

SEQ ID NO: 42            moltype = AA   length = 119
FEATURE                  Location/Qualifiers
REGION                   1..119
                         note = Synthetic
source                   1..119
                         mol_type = protein
                         organism = synthetic construct
SEQUENCE: 42
EVQLVESGGG LVQPGGSLRL SCAASGFTFS SYWMSWVRQA PGKGLEWVAN IKQDGGEKYY   60
VDSVKGRFTI SRDNAKNSLF LQMNSLRAED TAVYYCARVQ LYSDYFDYWG QGTLVTVSS    119

SEQ ID NO: 43            moltype = AA   length = 5
FEATURE                  Location/Qualifiers
REGION                   1..5
                         note = Synthetic
source                   1..5
                         mol_type = protein
                         organism = synthetic construct
SEQUENCE: 43
SYWMS                                                                  5

SEQ ID NO: 44            moltype = AA   length = 17
FEATURE                  Location/Qualifiers
REGION                   1..17
                         note = Synthetic
source                   1..17
                         mol_type = protein
                         organism = synthetic construct
SEQUENCE: 44
NIKQDGGEKY YVDSVKG                                                    17

SEQ ID NO: 45            moltype = AA   length = 10
FEATURE                  Location/Qualifiers
REGION                   1..10
                         note = Synthetic
source                   1..10
                         mol_type = protein
                         organism = synthetic construct
SEQUENCE: 45
VQLYSDYFDY                                                            10

SEQ ID NO: 46            moltype = DNA   length = 321
FEATURE                  Location/Qualifiers
misc_feature             1..321
                         note = Synthetic
source                   1..321
                         mol_type = other DNA
                         organism = synthetic construct
SEQUENCE: 46
gacatccaga tgacccagtc tccatcttcc gtgtctgcat ctgtaggaga cagagtcacc   60
atcacttgtc gggcgagtca gggtattagc agctggttag cctggtatca gcagaaatca  120
```

```
gggaaagccc ctaagctcct gatctatgct gcatccggtt tgcaaagtgg ggtcccatca   180
aggttcagcg gcagtggatc tgggacagat ttcactctca ccatcagcag cctgcagcct   240
gaagatttag caacttacta ttgtcaacag agtcacagtc ccctccgac gttcggccaa   300
gggaccaagg tggaaatcaa a                                             321

SEQ ID NO: 47              moltype = AA  length = 107
FEATURE                    Location/Qualifiers
REGION                     1..107
                           note = Synthetic
source                     1..107
                           mol_type = protein
                           organism = synthetic construct
SEQUENCE: 47
DIQMTQSPSS VSASVGDRVT ITCRASQGIS SWLAWYQQKS GKAPKLLIYA ASGLQSGVPS   60
RFSGSGSGTD FTLTISSLQP EDLATYYCQQ SHSLPPTFGQ GTKVEIK                 107

SEQ ID NO: 48              moltype = AA  length = 11
FEATURE                    Location/Qualifiers
REGION                     1..11
                           note = Synthetic
source                     1..11
                           mol_type = protein
                           organism = synthetic construct
SEQUENCE: 48
RASQGISSWL A                                                        11

SEQ ID NO: 49              moltype = AA  length = 7
FEATURE                    Location/Qualifiers
REGION                     1..7
                           note = Synthetic
source                     1..7
                           mol_type = protein
                           organism = synthetic construct
SEQUENCE: 49
AASGLQS                                                             7

SEQ ID NO: 50              moltype = AA  length = 9
FEATURE                    Location/Qualifiers
REGION                     1..9
                           note = Synthetic
source                     1..9
                           mol_type = protein
                           organism = synthetic construct
SEQUENCE: 50
QQSHSLPPT                                                           9

SEQ ID NO: 51              moltype = DNA  length = 363
FEATURE                    Location/Qualifiers
misc_feature               1..363
                           note = Synthetic
source                     1..363
                           mol_type = other DNA
                           organism = synthetic construct
SEQUENCE: 51
gaggtgcagc tgttggagtc tggggggagac ttggtccagc ctgggggggtc cctgagactc   60
tcctgtgcag cctctggatt caccttaac agctatgcca tgagctgggt ccgccaggct   120
ccaggaaagg ggctggagtg ggtctcaact attagtggta gtggtggttt cacattctcc   180
gcagactccg tgaagggccg gttcaccatc tccagagaca attccaagaa cacgctgttt   240
ctgcagatga acagcctgag agtcgaggac tcggccgtat attcctgtgc gaaagtcctt   300
gttggatta caatggctg ctgggactac tggggccagg gaaccctggt caccgtctcc   360
tca                                                                363

SEQ ID NO: 52              moltype = AA  length = 121
FEATURE                    Location/Qualifiers
REGION                     1..121
                           note = Synthetic
source                     1..121
                           mol_type = protein
                           organism = synthetic construct
SEQUENCE: 52
EVQLLESGGD LVQPGGSLRL SCAASGFTFN SYAMSWVRQA PGKGLEWVST ISGSGGFTFS   60
ADSVKGRFTI SRDNSKNTLF LQMNSLRVED SAVYSCAKVL VGFNNGCWDY WGQGTLVTVS   120
S                                                                  121

SEQ ID NO: 53              moltype = AA  length = 5
FEATURE                    Location/Qualifiers
REGION                     1..5
                           note = Synthetic
source                     1..5
```

-continued

```
                           mol_type = protein
                           organism = synthetic construct
SEQUENCE: 53
SYAMS                                                           5

SEQ ID NO: 54             moltype = AA  length = 17
FEATURE                   Location/Qualifiers
REGION                    1..17
                           note = Synthetic
source                    1..17
                           mol_type = protein
                           organism = synthetic construct
SEQUENCE: 54
TISGSGGFTF SADSVKG                                              17

SEQ ID NO: 55             moltype = AA  length = 12
FEATURE                   Location/Qualifiers
REGION                    1..12
                           note = Synthetic
source                    1..12
                           mol_type = protein
                           organism = synthetic construct
SEQUENCE: 55
VLVGFNNGCW DY                                                   12

SEQ ID NO: 56             moltype = DNA  length = 324
FEATURE                   Location/Qualifiers
misc_feature              1..324
                           note = Synthetic
source                    1..324
                           mol_type = other DNA
                           organism = synthetic construct
SEQUENCE: 56
tcctatgtgc tgactcagcc accctcggtg tcagtggccc caggacagac ggccaggatt  60
acctgtgggg gaaacaacat tggaagtaaa agtgtgcact ggtaccagca gaagccaggc  120
caggcccctg tgctggtcgt ctatgatgat agcgaccggc cctcaggat ccctgagcga  180
ttctctggct ccaactctgg gaacacggcc accctgacca tcagcagggt cgaagccggg  240
gatgaggccg actattactg tcaggtgtgg gatagtagta atgatcatgt ggtattcggc  300
ggagggacca agctgaccgt ccta                                     324

SEQ ID NO: 57             moltype = AA  length = 108
FEATURE                   Location/Qualifiers
REGION                    1..108
                           note = Synthetic
source                    1..108
                           mol_type = protein
                           organism = synthetic construct
SEQUENCE: 57
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSNDHVVFG GGTKLTVL              108

SEQ ID NO: 58             moltype = AA  length = 11
FEATURE                   Location/Qualifiers
REGION                    1..11
                           note = Synthetic
source                    1..11
                           mol_type = protein
                           organism = synthetic construct
SEQUENCE: 58
GGNNIGSKSV H                                                    11

SEQ ID NO: 59             moltype = AA  length = 7
FEATURE                   Location/Qualifiers
REGION                    1..7
                           note = Synthetic
source                    1..7
                           mol_type = protein
                           organism = synthetic construct
SEQUENCE: 59
DDSDRPS                                                          7

SEQ ID NO: 60             moltype = AA  length = 11
FEATURE                   Location/Qualifiers
REGION                    1..11
                           note = Synthetic
source                    1..11
                           mol_type = protein
                           organism = synthetic construct
SEQUENCE: 60
```

```
QVWDSSNDHV V                                                         11

SEQ ID NO: 61            moltype = DNA   length = 360
FEATURE                  Location/Qualifiers
misc_feature             1..360
                         note = Synthetic
source                   1..360
                         mol_type = other DNA
                         organism = synthetic construct
SEQUENCE: 61
gaggtgcagc tggtcgagtc tggcggcgga ctggtgaagc ctggcggctc cctgagactg   60
tcttgcgccg ccagtggctt tacattcagt acctactcca tgaactgggt ccgccaggca  120
ccaggcaagg gcctggaatg ggtgtcctcc atctcatcca gtggcgacta catctactat  180
gccgactccg tgaagggccg gttcaccatc tcccgggaca acgccaagaa ctccctgtat  240
ctgcagatga actccctgag agccgaggac accgccgtgt actactgcgc cagggacctg  300
gtgacatcca tggtggcctt cgactactgg ggtcagggca ctctcgtcac agtgtcctct  360

SEQ ID NO: 62            moltype = AA   length = 120
FEATURE                  Location/Qualifiers
REGION                   1..120
                         note = Synthetic
source                   1..120
                         mol_type = protein
                         organism = synthetic construct
SEQUENCE: 62
EVQLVESGGG LVKPGGSLRL SCAASGFTFS TYSMNWVRQA PGKGLEWVSS ISSSGDYIYY    60
ADSVKGRFTI SRDNAKNSLY LQMNSLRAED TAVYYCARDL VTSMVAFDYW GQGTLVTVSS   120

SEQ ID NO: 63            moltype = AA   length = 5
FEATURE                  Location/Qualifiers
REGION                   1..5
                         note = Synthetic
source                   1..5
                         mol_type = protein
                         organism = synthetic construct
SEQUENCE: 63
TYSMN                                                                5

SEQ ID NO: 64            moltype = AA   length = 17
FEATURE                  Location/Qualifiers
REGION                   1..17
                         note = Synthetic
source                   1..17
                         mol_type = protein
                         organism = synthetic construct
SEQUENCE: 64
SISSSGDYIY YADSVKG                                                   17

SEQ ID NO: 65            moltype = AA   length = 11
FEATURE                  Location/Qualifiers
REGION                   1..11
                         note = Synthetic
source                   1..11
                         mol_type = protein
                         organism = synthetic construct
SEQUENCE: 65
DLVTSMVAFD Y                                                         11

SEQ ID NO: 66            moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 66
tcttacgagc tgacccagcc tccttccgtg tccgtgtctc caggacagac ggccagaatc   60
acctgttccg gcgacgccct gcctcagaaa tacgtgttct ggtatcagca gaagtccggc  120
caggcccctg tgctggtgat ctacgaggac tccaagcggc cttccggcat ccctgagcgg  180
ttctccggct cctcttccgg caccatggcc accctgacca tctctggcgc ccaggtggag  240
gacgaggccg actactactg ctactccacc gacagatccg gcaaccacag agtgtttggt  300
gggggtacta agctgaccgt gctg                                         324

SEQ ID NO: 67            moltype = AA   length = 108
FEATURE                  Location/Qualifiers
REGION                   1..108
                         note = Synthetic
source                   1..108
                         mol_type = protein
```

-continued

```
                        organism = synthetic construct
SEQUENCE: 67
SYELTQPPSV SVSPGQTARI TCSGDALPQK YVFWYQQKSG QAPVLVIYED SKRPSGIPER    60
FSGSSSGTMA TLTISGAQVE DEADYYCYST DRSGNHRVFG GGTKLTVL                 108

SEQ ID NO: 68           moltype = AA   length = 11
FEATURE                 Location/Qualifiers
REGION                  1..11
                        note = Synthetic
source                  1..11
                        mol_type = protein
                        organism = synthetic construct
SEQUENCE: 68
SGDALPQKYV F                                                         11

SEQ ID NO: 69           moltype = AA   length = 7
FEATURE                 Location/Qualifiers
REGION                  1..7
                        note = Synthetic
source                  1..7
                        mol_type = protein
                        organism = synthetic construct
SEQUENCE: 69
EDSKRPS                                                              7

SEQ ID NO: 70           moltype = AA   length = 11
FEATURE                 Location/Qualifiers
REGION                  1..11
                        note = Synthetic
source                  1..11
                        mol_type = protein
                        organism = synthetic construct
SEQUENCE: 70
YSTDRSGNHR V                                                         11

SEQ ID NO: 71           moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 71
gaggtgcagc tggtcgagtc tggcggagga ctggtgcagc ctggcggctc cctgagactg    60
tcttgcgccg cctccggctt caccttctcc cggtactgga tgtcttgggt gcgccaggct   120
cctggcaagg gactggaatg ggtggccaac atcaaacagg atggctctga gaagtactac   180
gtggactccg tgaagggccg gttcaccatc tccagggaca acgccaagaa ctccctgtac   240
ctgcagatga actccctgag ggccgaggac accgccgtgt actactgtgc ccgggagggc   300
ggatggttcg gcgagctggc cttcgattac tggggccagg gcaccctggt gacagtgtcc   360
tct                                                                 363

SEQ ID NO: 72           moltype = AA   length = 121
FEATURE                 Location/Qualifiers
REGION                  1..121
                        note = Synthetic
source                  1..121
                        mol_type = protein
                        organism = synthetic construct
SEQUENCE: 72
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
S                                                                   121

SEQ ID NO: 73           moltype = AA   length = 11
FEATURE                 Location/Qualifiers
REGION                  1..11
                        note = Synthetic
source                  1..11
                        mol_type = protein
                        organism = synthetic construct
SEQUENCE: 73
GFTFSRRYWM S                                                         11

SEQ ID NO: 74           moltype = AA   length = 17
FEATURE                 Location/Qualifiers
REGION                  1..17
                        note = Synthetic
source                  1..17
                        mol_type = protein
```

```
                         organism = synthetic construct
SEQUENCE: 74
NIKQDGSEKY YVDSVKG                                                    17

SEQ ID NO: 75            moltype = AA  length = 12
FEATURE                  Location/Qualifiers
REGION                   1..12
                         note = Synthetic
source                   1..12
                         mol_type = protein
                         organism = synthetic construct
SEQUENCE: 75
EGGWFGELAF DY                                                         12

SEQ ID NO: 76            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 76
gagatcgtgc tgacccagtc ccctggcacc ctgtctctgt ctcccggcga gagagccacc   60
ctgtcttgcc gggcctccca gcgggtgtcc tcctcctacc tggcctggta tcagcagaaa  120
cccgacagg ccctaggct gctgatctac gacgcctcct ccagagccac cggcatccct   180
gaccggttct ccggctctgg ctccggcacc gacttcaccc tgaccatctc ccggctggaa  240
cctgaggact ttgccgtgta ttactgccag cagtacggct ccctgccttg gaccttcggc  300
cagggaacca aggtggagat caaa                                          324

SEQ ID NO: 77            moltype = AA  length = 108
FEATURE                  Location/Qualifiers
REGION                   1..108
                         note = Synthetic
source                   1..108
                         mol_type = protein
                         organism = synthetic construct
SEQUENCE: 77
EIVLTQSPGT LSLSPGERAT LSCRASQRVS SSYLAWYQQK PGQAPRLLIY DASSRATGIP   60
DRFSGSGSGT DFTLTISRLE PEDFAVYYCQ QYGSLPWTFG QGTKVEIK              108

SEQ ID NO: 78            moltype = AA  length = 12
FEATURE                  Location/Qualifiers
REGION                   1..12
                         note = Synthetic
source                   1..12
                         mol_type = protein
                         organism = synthetic construct
SEQUENCE: 78
RASQRVSSSY LA                                                        12

SEQ ID NO: 79            moltype = AA  length = 7
FEATURE                  Location/Qualifiers
REGION                   1..7
                         note = Synthetic
source                   1..7
                         mol_type = protein
                         organism = synthetic construct
SEQUENCE: 79
DASSRAT                                                               7

SEQ ID NO: 80            moltype = AA  length = 9
FEATURE                  Location/Qualifiers
REGION                   1..9
                         note = Synthetic
source                   1..9
                         mol_type = protein
                         organism = synthetic construct
SEQUENCE: 80
QQYGSLPWT                                                             9
```

The invention claimed is:

1. A purified antibody or an antigen-binding fragment thereof, wherein the antibody or antigen-specific fragment thereof is specific for B7-H1 and comprises:

a) a heavy chain variable domain, wherein the heavy chain variable domain comprises an amino acid sequence having at least about 85% identity to the amino acid sequence of SEQ ID NO: 52; and b) a light chain variable domain, wherein the light chain variable domain comprises an amino acid sequence having at least about 90% identity to the amino acid sequence of SEQ ID NO: 57.

2. The purified antibody or antigen-binding fragment thereof of claim 1, wherein the heavy chain variable domain comprises an amino acid sequence having greater than 85% identity to the amino acid sequence of SEQ ID NO: 52.

3. The purified antibody or antigen-binding fragment thereof of claim 1, wherein the light chain variable domain comprises an amino acid sequence having greater than 90% identity to the amino acid sequence of SEQ ID NO: 57.

4. The purified antibody or antigen-binding fragment thereof of claim 3, wherein the light chain variable domain comprises an amino acid sequence having greater than 95% identity to the amino acid sequence of SEQ ID NO: 57.

5. The purified antibody or antigen-binding fragment thereof of claim 1, wherein the antibody or antigen-binding fragment thereof cross-reacts with cynomolgus monkey B7-H1.

6. The purified antibody or antigen-binding fragment thereof of claim 1, wherein the antibody or antigen-binding fragment thereof inhibits binding of human B7-H1 to PD-1 expressed on ES-2 cells with an IC50 of less than 0.2 nM.

7. The purified antibody or antigen-binding fragment thereof of claim 1, wherein the antibody or antigen-binding fragment thereof activates CD4+ T cells in dendritic cell-T-cell mixed lymphocyte assay.

8. The purified antibody or antigen-binding fragment thereof of claim 1, wherein the antibody or antigen-binding fragment thereof enhances T-cell proliferation in DCMLR assay.

9. The purified antibody or antigen-binding fragment thereof of claim 1, wherein the antibody or antigen-binding fragment thereof enhances IFN-γ release in DCMLR assay.

10. A purified antibody or an antigen-binding fragment thereof, wherein the antibody or antigen-specific fragment thereof is specific for B7-H1 and comprises:

a) a heavy chain variable domain, wherein the heavy chain variable domain comprises an amino acid sequence having at least about 85% identity to the amino acid sequence of SEQ ID NO: 52 and comprises a CDR1 having the amino acid sequence of SEQ ID NO: 101; and b) a light chain variable domain, wherein the light chain variable domain comprises an amino acid sequence having at least about 99% identity to the amino acid sequence of SEQ ID NO: 57.

* * * * *